(12) United States Patent
Ward et al.

(10) Patent No.: US 8,658,133 B2
(45) Date of Patent: Feb. 25, 2014

(54) METHODS AND COMPOSITIONS RELATING TO ALZHEIMER'S DISEASE

(75) Inventors: Malcolm Ward, Cobham (GB); Vaksha Patel, Cobham (GB); Emma McGregor, London (GB); Nicola Leeds, Tonbridge (GB); Helen Byers, Cobham (GB); James Campbell, Cobham (GB); Kit-Yi Leung, Berkhamsted (GB); Jules Westbrook, Dublin (IE)

(73) Assignee: Proteome Sciences plc, Cobham, Surrey (GB)

( * ) Notice: Subject to any disclaimer, the term of this patent is extended or adjusted under 35 U.S.C. 154(b) by 1216 days.

(21) Appl. No.: 11/574,367

(22) PCT Filed: Aug. 26, 2005

(86) PCT No.: PCT/GB2005/003366
§ 371 (c)(1),
(2), (4) Date: Mar. 19, 2008

(87) PCT Pub. No.: WO2006/021810
PCT Pub. Date: Mar. 2, 2006

(65) Prior Publication Data
US 2009/0275495 A1 Nov. 5, 2009

(30) Foreign Application Priority Data
Aug. 27, 2004 (GB) .................................. 0419124.3

(51) Int. Cl.
*A61K 49/00* (2006.01)
*G01N 33/15* (2006.01)

(52) U.S. Cl.
USPC .................. 424/9.1; 424/9.2; 506/10; 800/3; 800/12; 800/13; 800/14

(58) Field of Classification Search
None
See application file for complete search history.

(56) References Cited

U.S. PATENT DOCUMENTS

| | | | |
|---|---|---|---|
| 6,717,031 B2 * | 4/2004 | Games et al. .................... | 800/12 |
| 2002/0009713 A1 | 1/2002 | Miller et al. | |
| 2002/0104104 A1 * | 8/2002 | Games et al. ..................... | 800/3 |
| 2003/0032070 A1 | 2/2003 | Good et al. | |
| 2003/0066097 A1 | 4/2003 | Monte et al. | |
| 2004/0022794 A1 | 2/2004 | Durham et al. | |
| 2004/0076958 A1 | 4/2004 | Ikezu | |

FOREIGN PATENT DOCUMENTS

| | | |
|---|---|---|
| EP | 0653154 A2 | 5/1995 |
| JP | 2001-506226 | 5/2001 |
| JP | 2003-284574 | 10/2003 |
| WO | 96/35446 | 11/1996 |
| WO | 02096415 A2 | 12/2002 |
| WO | 03/028543 A2 | 4/2003 |
| WO | 2004007673 A2 | 1/2004 |

OTHER PUBLICATIONS

Lahiri D., Journal of Molecular Neuroscience, 23(3):225-233, Jul. 2004.*
Profenno et al., Society for Neuroscience Abstracts, 2001; 27: 2567.*
Shibata et al., Journal of Clinical Investigation, 2000; 106: 1489-1499.*
Lahiri abstract from the publisher downloaded Jul. 20, 2010 from springerlink.com/content/e0465r41302gg592/ (5 pages total).*
Hatanpää et al., Journal of Neuropathology and Experimental Neurology, 1999; 58: 637-643.*
Website downloaded Nov. 1, 2011: graphpad.com/articles/interpret/principles/stat_sig.htm; 2 pages total.*
Daniel, "Biostatistics: A Foundation for Analysis in the Health Sciences", 7th edition, 1999, John Wiley & Sons, Inc. pp. 7-8.*
A. Bizzi et al., "Axonal transport of two major components of the ubiquitin system: free ubiquitin and ubiquitin carboxyl-terminal hydrolase PGP 9.5", Brain Research, 548: 292-299 (1991).
P. Davies et al., "Consensus Report of the Working Group on: Molecular and Biochemical Markers of Alzheimer's Disease", Neurobiology of Aging, 19(2): 109-116 (1998).
L. Ho et al., "Altered expression of a-type but not b-type synapsin isoform in the brain of patients at high risk for Alzheimer's disease assessed by DNA microarray technique", Neuroscience Letters, 298(3): 191-194 (2001).
J. Loring et al., "A Gene Expression Profile of Alzheimer's Disease", DNA and Cell Biology, 20(11): 683-695 (2001).
A. Hye et al., "Proteomics in the early diagnosis of Alzheimer's disease", Society for Neuroscience Abstract Viewer and Itinerary Planner, 2003, pp. Abstract No. 202..24.
J. Choi et al., "Oxidative Modifications and Down-regulation of Ubiquitin Carboxyl-terminal Hydrolase L1 Associated with Idiopathic Parkinson's and Alzheimer's Diseases", Journal of Biological Chemistry, 279(13): 13256-13264 (2004).

(Continued)

*Primary Examiner* — Bridget E Bunner
*Assistant Examiner* — Christina Borgeest
(74) *Attorney, Agent, or Firm* — Patrick J. Hagan; Dann, Dorfman, Herrell and Skillman, PC

(57) ABSTRACT

Methods and compositions relating to Alzheimer's disease are provided, including proteins that are differentially expressed in Alzheimer's disease as compared to the normal state. Further provided are methods, particularly experimental paradigms, for the identification of differential expressed proteins that are potential molecular targets for compounds to treat or prevent Alzheimer's disease. Also provided are methods for the identification and therapeutic use of compounds for the prevention and treatment of Alzheimer's disease.

17 Claims, 31 Drawing Sheets

(56) References Cited

OTHER PUBLICATIONS

Choi, Joungil et al., "Oxidative Modifications and Down-regulation of Ubiquitin Carboxy-terminal Hydrolase L1 Associated with Idiopathic Parkinson's and Alzheimer's Disease", The Journal of biological Chemistry, 279(13): 13256-13264 (2004).

Japanese Official Action, issued Jul. 16, 2013, in corresponding JP 2011-285674.

* cited by examiner

Horizontal axis: within group variation
Vertical axis: between group variation

Qualitative changes

| Qualitative | Spot Number | IPG | Identification | Species | Accession No | Mr (Da) | pI | Peptides matched | |
|---|---|---|---|---|---|---|---|---|---|
| ww only | 2937 | 6-9 | Glutathione S-transferase Mu 1 | mouse | P10649 | 25822 | 8.13 | 1 | YIATPIFSK |
| | Mr 29000 pI 8 | | DNA segment, Chr 10, Johns Hopkins University 81 expressed | mouse | gi\|20070420 | 28073 | 9 | 1 | NLSTFAVDGK |
| absent in tt | 1057 | 4-7 | Tubulin beta-4 chain | mouse | Q9D6F9 | 49520 | 4.78 | 17 | |
| | | | Tubulin beta-2 chain | mouse | gi\|13542680 | 49783 | 4.79 | 4 | unique |
| | Mr 44000 pI 5.9 | | tubulin beta chain 15 | rat | gi\|92930 | 49905 | 4.79 | 3 | unique |
| | | | Tubulin beta-2 chain | mouse | gi\|7106439 | 49639 | 4.78 | 1 | unique |
| ww only | 1301 | 4.7 | drebrin-like | mouse | gi\|7304993 | 46398 | 4.9 | 1 | |
| | | | Tubulin beta-3 | mouse | Q9ERD7 | 50386 | 4.82 | 1 | |
| | Mr 32000 pI 6.26 | | WW domain binding protein 2 (WBP-2) | mouse | P97765 | 28013 | 5.94 | 2 | |
| | | | Tubulin alpha-1 chain | mouse | P02551 | 50104 | 4.94 | 1 | |

| present in B |  |  |  |  |  |  |
|---|---|---|---|---|---|---|
| 540 | Ubiquitin-activating enzyme E1 | Mouse | Q02053 | 117734 | 6.43 | 3 | HYSDDFFQNLDGVAKALDMKDAR LACTCPHLEVLEAVQR |
|  |  |  |  |  |  |  | AAVASLLSSVGVPEFTMK TTFSVVAFTADGER |
| 468 | BIP-type molecular chaperone precursor | Mouse | P38547 | 73446 | 6.61 | 2 | DAVTNPNHTFYATK |
| 542 | Vault-type, H+ transporting, lysosomal | Rat |  | 70866 | 6.43 | 27 | ELDEEEDLAEVDLVSK |
| 544 | heat shock 070a protein 1 | Mouse | P24782 | 58293 | 4.43 | 1 | VSLDVNHFAPDELTVK |
|  | Junction plakoglobin (Desmoplakin III) | Human | Q02257 | 52790 | 6.59 | 1 | MLVTGMSGVEAJMALR |
|  |  | Mouse |  | 65968 | 6.95 | 1 | GVDSDDLPLNVSR |
| 666 | dehydropalmitinose-like 2 | Mouse |  | 62239 | 6.95 | 22 | GKDNQVGTYEK |
| 766 | ATPase, H+ transporting, lysosomal | Rat |  | 65516 | 6.57 | 23 | ILQDASGR |
|  | NADH dehydrogenase (ubiquinone) Fe-S protein 1 | Mouse | P38916 | 79698 | 6.61 | 2 |  |
| 763 | Dihydropyrimidinase, lysosomal | Mouse |  | 62239 | 6.96 | 16 | GVNVSALR |
|  | ATPase, H+ transporting, lysosomal | Mouse |  | 65283 | 6.42 | 5 | TVSGGLSK |
|  |  |  |  |  |  |  | MALVAHTSNHPVAAR |
|  |  |  |  |  |  |  | LDEMPADSGYPRAYLGAR |
|  |  |  |  |  |  |  | LASFYGR |
| 002 | tubulin beta chain 15 | Rat | QU7976 | 49904 | 4.73 | 15 | EFSGYVESGLK |
|  | senexin VI | Mouse |  | 49877 | 6.91 | 2 | SEGLVOH |
| 928 | ATP synthase, H+ transporting | Mouse | P56480 | 56286 | 4.49 | 8 | TASLTSAASIDGSR |
|  | N-myc downstream regulated 2 | Mouse | Q9QYG0 | 40763 | 5.23 | 1 |  |
| 1021 | enolase 2 | Human |  | 47367 | 4.58 | 14 |  |
| 1052 | gelatinase | Mouse |  | 80582 | 6.68 | 7 |  |
| 1055 | tubulin beta chain 15 | Rat |  | 49906 | 4.78 | 22 |  |
|  | gamma-actin | Mouse |  | 40582 | 6.86 | 4 |  |
|  |  |  |  |  |  |  | VAPEEHPVLLTEAPLKPK |
| 1120 | Tubulin alpha chain | Mouse | P02551 | 50154 | 4.94 | 8 | GYSFTTTAER |
|  | Tubulin beta chain | Mouse | GI13642580 | 49783 | 4.79 | 12 | SYELPDGQVITIGNER |
|  | ATP synthase beta chain | Mouse | P56480 | 56365 | 5.19 | 1 | EITALAPSTMK |
|  | Ubiquitin carboxyl-terminal hydrolase | Mouse | P56399 | 95772 | 4.89 | 1 |  |
| 1153 | similar to interferon-inducible protein 10 (IP-10) receptor | Mouse |  | 66796 | 6.14 | 10 |  |
| 1234 | shark-type molecular chaperone hsp72-ps1 | Rat |  | 70484 | 6.43 | 6 |  |
|  | tropomyosin beta | Mouse | P58771 | 32226 | 4.61 | 11 |  |
| 1401 | ATP synthase, beta chain | Mouse | P56480 | 56268 | 6.19 | 7 |  |
| 1614 | ATP synthase, beta chain | Human | P36214 | 64286 | 6.19 | 2 |  |
|  | Protein kinase C inhibitor | Mouse | P07437 | 28104 | 4.80 | 2 |  |
| 1818 | tubulin, beta polypeptide | Human | Q02338 | 49878 | 4.78 | 6 |  |
| 1671 | ATP synthase alpha chain | Mouse | P68071 | 59714 | 9.22 | 5 |  |
|  | Superoxide dismutase | Mouse | GI17983569 | 24683 | 6.9 | 2 |  |
|  | protein proteasome-1 regulatory subunit 7 | Mouse | GI28843893 | 45365 | 4.86 | 5 | ATDAEADVASLNR |
|  | CGI-121 protein | Mouse | Q8RDP6 | 15645 | 5.84 | 2 | C-terminal peptides |
| 1683 | Ubiquitin carboxyl-terminal hydrolase isozyme L1 | Mouse | P26528 | 24822 | 6.14 | 10 |  |
|  | ferritin heavy chain | Mouse |  | 21483 | 6.53 | 2 | YFLHQSMEER |
|  |  |  |  |  |  |  | IFLODK |
| 1692 | Gamma-soluble NSF attachment protein | Mouse | Q9CWZ7 | 34719 | 6.80 | 5 | N-terminal peptides matched |
| 1848 | Proteasin subunit 5 | Mouse | Q9WU25 | 17345 | 6.33 | 13 |  |
|  | cAMP-dependent protein kinase type I-alpha regulatory chain | Rat | P08455 | 43736 | 6.27 | 12 |  |
|  | guanylate kinase 1 | Mouse | Q54520 | 21394 | 6.12 | 1 | ICVLCVDQGVR |

| | | | | | |
|---|---|---|---|---|---|
| Short chain 3-hydroxyacyl-CoA dehydrogenase, mitochondrial precursor | mouse | Q61425 | 34442 | 8.76 | 2 | TFESLVDFCK LLVPPLIEAVR |
| ATP synthase alpha chain, mitochondrial precursor | mouse | Q03265 | 59716 | 9.22 | 3 | TGAVVGPVGEELLGR EAYPGDVFYLHSR QQGGYSPNAIEEQVANVYAGVR |
| Voltage-dependent anion-selective channel protein 2 | mouse | Q60930 | 31743 | 7.44 | 2 | YQLDPTASISAK LTLSALVDGK |
| Carbonyl reductase [NADPH] 1 (EC 1.1.1.184) (NADPH-dependent carbonyl reductase 1) | mouse | P48758 | 30578 | 7.6 | 1 | HGVTVLSR |
| Microtubule-associated protein 1 B | mouse | gi|6678644 | 270345 | 4.78 | 1 | AVLDALEGK |
| IncoA 2 protease precursor | mouse | P58252 | 47124 | 9.13 | 1 | |
| Phosphoglycerate mutase 1 | mouse | Q9DBJ1 | 28685 | 6.75 | 1 | ALPFWNEETVPQIK |
| CCPG (constitutive photomorphogenic) homolog, subunit 7a | mouse | gi|7242142 | 30208 | 7.68 | 1 | |
| Acetyl-CoA acetyltransferase, mitochondrial precursor | mouse | gi|21450129 | 44787 | 8.71 | 12 | |
| Fructose-bisphosphate aldolase A | mouse | P05064 | 39360 | 8.33 | 6 | |
| Ubiquinol-cytochrome C reductase complex core protein 2 | mouse | Q9DB77 | 48205 | 9.24 | 4 | |
| Phosphoglycerate kinase 1 | mouse | P09411 | 44377 | 7.52 | 3 | |
| Aspartate aminotransferase, cytoplasmic | mouse | P05201 | 46071 | 6.75 | 2 | |

Fig. 5B

Rest of Hemisphere 4-7L

| Comparison | Spot number | Identification | Species | Accession No | Mr (Da) | pI | Peptides matched | Peptide Sequence |
|---|---|---|---|---|---|---|---|---|
| tw and wt vs ww | 1823 | Proteasome subunit alpha type 6 | mouse | Q9QUM9 | 27355 | 6.34 | 10 | LSGPGGSGSFR ALEAELAALR |
| | | Alpha-internexin (Alpha-Inx) | mouse | P46660 | 55836 | 5.16 | 2 | |
| | Mr 29000 | Phosphoglycerate mutase 1 | mouse | Q9DBJ1 | 28683 | 6.75 | 1 | |
| | pI 6.85 | HSCO protein | mouse | gi\|12963539 | 27721 | 6.78 | 6 | |
| | 7427 | Tubulin beta-4 chain | mouse | Q9D6F9 | 49520 | 4.78 | 6 | |
| | | Tubulin beta-1 chain | mouse | P02551 | 50104 | 4.94 | 1 | |
| | Mr 37000 | Ubiquinol-cytochrome C reductase complex core protein I, mitochondrial precursor | mouse | Q9CZ13 | 52735 | 5.75 | 3 | |
| | pI 5.5 | Neurofilament triplet M protein | mouse | P08553 | 95646 | 4.76 | 1 | |
| | | Mu-crystallin homolog | mouse | O54983 | 33502 | 5.44 | 1 | |
| tw and tt vs ww | 372 Mr 70000 pI 6.5 | Dihydropyrimidinase related protein-2 (DRP-2) | rat | P47942 | 62239 | 5.95 | 10 | |
| tw,wt and tt vs ww | 1566 | Apolipoprotein E precursor (Apo-E) | mouse | P08226 | 35844 | 5.56 | 10 | VLEAELLVLR IDSLMDEIAFLK |
| | | Neurofilament triplet L protein | mouse | P08551 | 61411 | 4.63 | 2 | EILDEEDLAEIVQLVGK |
| | Mr 32000 | ATPase, H+ transporting, lysosomal | mouse | gi\|20892559 | 68283 | 5.42 | 1 | AAVPSGASTGIYEALELR |
| | pI 5.7 | Alpha enolase | reptile | Q9W7L1 | 47172 | 6.08 | 1 | |
| | | Creatine kinase, B chain | mouse | Q04447 | 42686 | 5.4 | 2 | |
| | | Neurofilament triplet M protein | mouse | P08553 | 95553 | 4.76 | 1 | VQSLQDEVAFLR |
| | | Voltage-dependent anion-selective channel protein 2 | mouse | Q60930 | 31713 | 7.44 | 1 | LTLSALVDGK |
| | | RIKEN cDNA 4732495G21 gene | mouse | gi\|30425250 | 41977 | 5.3 | 1 | |
| | 696 | Glycerol-3-phosphate dehydrogenase | mouse | Q64521 | 80848 | 6.17 | 4 | |
| | | Lamin B2 | mouse | P21619 | 66989 | 5.44 | 2 | |
| | Mr 50000 | Dihydropyrimidinase related protein-2 (DRP-2) | mouse | O08553 | 62132 | 5.95 | 1 | |
| | pI 6.1 | Lamin B3 | mouse | P48680 | 53236 | 5.74 | 1 | |

Fig 6

| Genotype | Hippocampus pH 4-7L Spot No. | | | | | |
|---|---|---|---|---|---|---|
| | 1341 | 1498 | 1554 | 614 | 1976 | 1585 |
| TW | ↓ | ↓ | ↑ | | ↓ | ↓ |
| WT | ↓ | ↓ | ↑ | ↑ | | |
| TT | | | | ↑ | ↓ | ↓ |

| Genotype | Hippocampus pH 6-9L Spot No. | | | |
|---|---|---|---|---|
| | 1017 | 884 | 980 | 1023 |
| TW | ↓ | ↓ | ↓ | ↓ |
| WT | ↓ | ↓ | ↓ | ↓ |
| TT | | | | ↓ |

| Genotype | ROH pH 4-7L Spot No. | | | | |
|---|---|---|---|---|---|
| | 696 | 1566 | 1823 | 7427 | 372 |
| TW | ↑ | ↑ | | | ↑ |
| WT | ↑ | ↑ | ↓ | ↑ | |
| TT | | ↑ | ↓ | ↑ | ↑ |

| Genotype | ROH pH 6-9L Spot No. | | | |
|---|---|---|---|---|
| | 1023 | 1661 | 1758 | 1892 |
| TW | ↑ | ↑ | ↑ | ↑ |
| WT | | | | |
| TT | ↑ | ↑ | ↑ | ↑ |

Fig 7

| Protein Name | Mouse | Human | Function |
|---|---|---|---|
| Glutathione S-transferase Mu 1 | P10649 | P09488 | Conjugation of reduced glutathione to many substrates |
| Tubulin beta-4 chain | Q9D6F9 | Q13509 | Tubulin is the major constituent of microtubules. It binds two moles of GTP |
| WW domain binding protein 2 (WBP-2) | P97765 | Q969T9 | Protein binding |
| Eukaryotic translation initiation factor 4H (eIF-4H) | Q9WUK2 | Q15056 | Stimulates protein translation |
| Ubiquitin carboxyl-terminal hydrolase isozyme L1 | Q9R0P9 | P09936 | Ubiquitin-protein hydrolase is involved both in the processing of ubiquitin precursors and of ubiquinated proteins. This enzyme is a thiol protease that recognizes and hydrolyzes a peptide bond at the C-terminal glycine of ubiquitin |
| Tubulin beta-3 | Q9ERD7 | ? | Major constituent of microtubules. |
| Neuronal protein Np25 (Transgelin 3) | Q9R1Q8 | ? | Actin binding |
| guanosine diphosphate (GDP) dissociation inhibitor 1 | P50396 | P31150 | Regulates the GDP/GTP exchange reaction of most Rab proteins by inhibiting the dissociation of GDP from them, and the subsequent binding of GTP to them. Highly expressed in the brain |
| dihydropyrimidinase-like 2 (DRP-2) | P47942 | Q16555 | Involved in the formation of neurons |
| Aspartate aminotransferase cytoplasmic | P05201 | P17174 | Catalytic activity: L-aspartate + 2-oxoglutarate = oxaloacetate + L-glutamate |
| Fructose-bisphosphate aldolase A | P05064 | P04075 | Muscle form (as below) |

Fig. 8A

| Protein Name | Mouse | Human | Function |
|---|---|---|---|
| Fructose-bisphosphate aldolase C | P05063 | P09972 | Brain-type aldolase Catalytic activity: D-fructose 1,6-bisphosphate = glycerone phosphate + D-glyceraldehyde 3-phosphate Glycolysis; sixth step |
| Synapsin II | Q8CE19 | Q92777 | Neuronal phosphoprotein that coats synaptic vesicles, binds to the cytoskeleton, and is believed to function in the regulation of neurotransmitter release |
| Nucleolysin TIA related protein | P70318 | P31483 (Human TIA) | Induction of apoptosis |
| Peptidylprolyl isomerase D (Cyclophilin like protein) | Q9CR16 | Q7Z6P2 (fragment) | PPIases accelerate the folding of proteins |
| Voltage-dependent anion-selective channel protein 1 (POR1) | Q60932 | P21796 | Forms a channel through the mitochondrial outer membrane and also the plasma membrane |
| Acetyl-CoA acetyltransferase, mitochondrial precursor | gi 21450129 | P24752 | Plays a major role in ketone body metabolism |
| Apolipoprotein E | P08553 | P02649 | Involved in the processing of lipoprotein particles and is secreted in plasma |
| Proteasome subunit alpha type 6 | Q9QUM9 | P60900 | Protease involved in non-lysosomal proteolytic pathway |

Fig. 8B

Hippocampus pH 6-9

| Comparison | Spot number | Identification | Species | Accession No | Human Accession No |
|---|---|---|---|---|---|
| rw and wt versus ww | 1017 | Aspartate aminotransferase, cytoplasmic | Mouse | P05201 | P17174 |
| | Mr 45000 pI 6.9 | Fructose-bisphosphate aldolase C | Mouse | P05063 | P09972 |
| | | Fructose-bisphosphate aldolase A | Mouse | P05064 | P04075 |
| | | Isocitrate dehydrogenase 3, beta subunit | Mouse | gi|18700024 | O43837 |
| | | synapsin II | Mouse | gi|8567410 | Q92777 |
| | | 40 kDa peptidyl-prolyl cis-trans isomerase | Mouse | Q8CR16 | Q08752 |
| | | 2',3'-cyclic nucleotide 3'-phosphodiesterase | Mouse | P16330 | P09543 |
| | | Acetyl-CoA acetyltransferase 1 precursor | Mouse | gi|21450129 | P24752 |
| | | Cytosolic acyl coenzyme A thioester hydrolase | Mouse | Q91V12 | O00154 |
| | | Pyruvate dehydrogenase E1 component, alpha subunit | Mouse | P35486 | P08559 |
| | 884 | Creatine kinase, ubiquitous mitochondrial precursor | Mouse | P30275 | P12532 |
| | Mr 45000 pI 7.2 | Heterogeneous nuclear ribonucleoprotein D0 | Mouse | Q60668 | Q14103 |
| | | Phosphoglycerate kinase 1 | Mouse | P09411 | P00558 |
| | | Neuronal tropomodulin | Mouse | Q8JKK7 | Q9NZR1 |
| | 980 | Aspartate aminotransferase, cytoplasmic | Mouse | P05201 | P17174 |
| | Mr 40000 pI 6.7 | Fructose-bisphosphate aldolase C | Mouse | P05063 | P09972 |
| | | Fructose-bisphosphate aldolase A | Mouse | P05064 | P04075 |

Fig. 9A

| | | | | |
|---|---|---|---|---|
| | | 2',3'-cyclic nucleotide 3'-phosphodiesterase | Mouse | P16330 | P09543 |
| | | Synapsin II | Mouse | gi\|8567410 | Q92777 |
| | | Nucleolysin TIAR | Mouse | P70318 | Q01085 |
| | | Acetyl-CoA acetyltransferase 1 precursor | Mouse | gi\|21450129 | P24752 |
| | | Isocitrate dehydrogenase 3, beta subunit | Mouse | gi\|18700024 | O43837 |
| | | Neuronal tropomodulin | Mouse | gi\|23396882 | Q9NZR1 |
| tw, wt and tt versus tt | 1023 | peptidylprolyl isomerase D | Mouse | Q9CR16 | Q08752 |
| | Mr 44000 pI 7.0 | aspartate transaminase | Mouse | P05201 | P17174 |
| | | aldolase A | Mouse | P05064 | P04075 |
| | | isocitrate dehydrogenase 3 | Rat | P50554 | P80404 |
| Unique to tw only | 1191 | Voltage-dependent anion-selective channel protein 1 | Mouse | Q60932 | P21796 |
| | Mr 32000 pI 8.4 | Short chain 3-hydroxyacyl-CoA dehydrogenase, mitochondrial precursor | Mouse | Q61425 | Q16836 |
| | | ATP synthase alpha chain, mitochondrial precursor | Mouse | Q03265 | P25705 |
| | | Voltage-dependent anion-selective channel protein 2 | Mouse | Q60930 | P45880 |
| | | Carbonyl reductase [NADPH] 1 (EC 1.1.1.184) (NADPH-dependent carbonyl reductase 1) | Mouse | P48758 | P16152 |
| | | microtubule-associated protein 1 B | Mouse | gi\|6678946 | P46821 |
| | 1303 | Hydroxyacylglutathione hydrolase | Mouse | Q99KB8 | Q16775 |
| | Mr 30000 pI 6.6 | 14-3-3 protein zeta/delta | Mouse | P35215 | P29312 |
| | | Phosphoglycerate mutase 1 | Mouse | Q9DBJ1 | P18669 |
| | | COP9 (constitutive photomorphogenic) homolog, subunit 7a | Mouse | gi\|7242142 | Q9UJW4 |

Fig. 9B

| | | | |
|---|---|---|---|
| 971 | Acetyl-CoA acetyltransferase, mitochondrial precursor | Mouse | P24752 |
| Mr 44000 pI 8.3 | Fructose-bisphosphate aldolase A | Mouse | Q8R4S0129 | P04075 |
| | Ubiquinol-cytochrome C reductase complex core protein 2 | Mouse | P060084 | P22695 |
| | Phosphoglycerate kinase 1 | Mouse | Q9C0377 | P09411 | P00568 |
| | Aspartate aminotransferase, cytoplasmic | Mouse | P05201 | P17174 |

Fig. 9C

Qualitative changes

| Qualitative | Spot Number | IPG | Identification | Species | Accession No | Human Accession No |
|---|---|---|---|---|---|---|
| ww only | 2937 Mr 29000 pl 8 | 6-9 | Glutathione S-transferase Mu 1 | Mouse | P10649 | P09488 |
| | | | DNA segment, Chr 10, Johns Hopkins University 81 expressed | Mouse | gi|20070420 | ? |
| absent in tt | 1057 Mr 44000 pl 5.9 | 4-7 | Tubulin beta-4 chain | Mouse | Q9D6F9 | Q13509 |
| | | | Tubulin beta-2 chain | Mouse | gi|13542680 | P05217 |
| | | | tubulin beta chain 15 | Rat | gi|92930 | ? |
| | | | Tubulin beta-2 chain | Mouse | gi|7106439 | P05217 |
| ww only | 1301 Mr 32000 pl 6.26 | 4.7 | drebrin-like | Mouse | gi|7304993 | Q9UJU6 |
| | | | Tubulin beta-3 | Mouse | Q9ERD7 | ? |
| | | | WW domain binding protein 2 (WBP-2) | Mouse | P97765 | Q969T9 |
| | | | Tubulin alpha-1 chain | Mouse | P02551 | P05209 |

Fig. 9D

Hippocampus 4-7

| Comparison | Spot number | Identification | Species | Accession No | Human Accession No |
|---|---|---|---|---|---|
| tw, wt versus ww | 1341 | Eukaryotic translation initiation factor 4H (eIF-4H) | Mouse | Q9WUK2 | Q15056 |
| | Mr 30000 pI 6.8 | Nit protein 2 | Mouse | gi|12963555 | ? |
| | | Transcriptional activator protein PUR-alpha | Mouse | P42669 | Q00577 |
| | | Carbonic anhydrase 2 | Mouse | gi|33243954 | P00918 |
| | | Tuba2 protein | Mouse | P36220 | Q13748 |
| | | pyruvate dehydrogenase (lipoamide) beta | Mouse | gi|18152793 | ? |
| | 1554 | beta-actin | Mouse | gi|49868 | ? |
| | Mr 25000 pI 5.9 | Transitional endoplasmic reticulum ATPase | Mouse | Q01853 | P55072 |
| | | SH3-containing GRB2-like protein 2 | Rat | O35179 | Q99962 |
| | | Hspd1 protein | Mouse | gi|17391295 | P10809 |
| | 1498 | Ubiquitin carboxyl-terminal hydrolase isozyme L1 | Mouse | Q9R0P9 | P09936 |
| | Mr 45000 pI 6.9 | Transitional endoplasmic reticulum ATPase | Mouse | Q01853 | P55072 |
| | | Actin 1 | Schistosoma | P53470 | ? |
| | | ATP synthase beta chain, mitochondrial precursor | Mouse | P56480 | P06576 |
| tw, tt versus ww | 1976 Mr 28000 pI 5.4 | Tubulin beta-3 | Mouse | Q9ERD7 | ? |
| | 1585 | neuronal protein Np25 | Mouse | Q9R1Q8 | Q9UH15 |
| | | ATP synthase, H+ transporting | Mouse | Q03265 | ? |
| | | guanylate kinase 1 | Mouse | Q64520 | Q16774 |

Fig. 9E

| | | | | | |
|---|---|---|---|---|---|
| wt, tt versus ww | glutathione S-transferase | | Mouse | P46425 | ? |
| | guanosine diphosphate (GDP) dissociation inhibitor 1 | 514 | Mouse | P50396 | P31150 |
| | tumor rejection antigen gp96 | | Mouse | P08113 | P14625 |
| present in tt | ubiquitin-activating enzyme E1 | 240 | Mouse | Q02053 | P22314 |
| | dnaK-type molecular chaperone precursor | 458 | Mouse | P38647 | P38646 |
| | Heat Shock cognate 71kDa | 542 | Mouse | P08108 | P11142 |
| | ATPase, H+ transporting, lysosomal | 546 | Mouse | Q03265 | ? |
| | heat shock 27kDa protein 1 | | Human | P04792 | P04792 |
| | Junction plakoglobin (Desmoplakin III) | | Mouse | Q02257 | P14923 |
| | dihydropyrimidinase-like 2 | 669 | Mouse | P47942 | Q16555 |
| | Vacuolar ATP synthase subunit B | 756 | Mouse | P50517 | ? |
| | NADH dehydrogenases (ubiquinone) Fe-S protein 1 | | Mouse | gi(21704020 | ? |
| | dihydropyrimidinase-like 2 | 763 | Mouse | P47942 | Q16555 |
| | ATPase, H+ transporting, lysosomal | | Mouse | P50516 | P38606 |
| | tubulin beta chain 15 | 903 | Rat | gi|92930 | ? |
| | annexin VII | | Mouse | Q07076 | P20073 |

Fig. 9F

| | | | |
|---|---|---|---|
| 908 | ATP synthase, H+ transporting | Mouse | P56480 | P06576 |
| 1021 | N-myc downstream regulated 2 | Mouse | Q8QYG0 | Q8UN36 |
| 1052 | enolase 2 | Mouse | gi|7305027 | ? |
| 1056 | gamma-actin | Mouse | gi|809561 | ? |
| 1189 | tubulin beta chain 15 | Rat | gi|92930 | ? |
| | gamma-actin | Mouse | gi|809561 | ? |
| | Tubulin alpha chain | Mouse | P02551 | P05209 |
| | Tubulin beta chain | Mouse | gi|135422680 | ? |
| | ATP synthase, H+ transporting, beta chain | Mouse | P56480 | P06576 |
| | Ubiquitin carboxyl-terminal hydrolase | Mouse | P56399 | P45974 |
| 1199 | similar to interferon-inducible protein 10 (IP-10) receptor | Mouse | gi|20988919 | ? |
| 1224 | Heat Shock cognate 71kDa | Mouse | P08109 | P11142 |
| | tropomyosin alpha 1 chain | Mouse | P58771 | P09493 |
| 1401 | ATP synthase, H+ transporting, beta chain | Mouse | P56480 | P06576 |
| 1514 | ATP synthase, H+ transporting, beta chain | Mouse | P56480 | P06576 |
| 1818 | tubulin, beta polypeptide | Human | P07437 | P07437 |

Fig. 9G

| | | | | |
|---|---|---|---|---|
| 1871 | ATP synthase alpha chain | Mouse | Q03265 | P25705 |
| 1863 | Ubiquitin carboxyl-terminal hydrolase isozyme L1 | Mouse | Q8R0P6 | P09936 |
| | ferritin heavy chain | Mouse | P09528 | P02794 |
| 1853 | Gamma-soluble NSF attachment protein | Mouse | Q9CWZ7 | Q99747 |
| 1848 | Prefoldin subunit 5 | Mouse | Q9WU28 | Q99471 |
| | cAMP-dependent protein kinase type I-alpha regulatory chain | Rat | P09456 | P10644 |

Fig. 9H

Rest of Hemisphere 4-7L

| Comparison | Spot number | Identification | Species | Accession No | Human Accession No |
|---|---|---|---|---|---|
| tw and wt vs ww | 1823 | Proteasoma subunit alpha type 6 | Mouse | Q9QUM9 | P60900 |
| | Mr 29000 pl 6.65 | Alpha-internexin (Alpha-inx) | Mouse | P46660 | Q16352 |
| | | Phosphoglycerate mutase 1 | Mouse | Q9D8J1 | P18669 |
| | | HSCO protein | Mouse | gi\|12963539 | Q96571 |
| | 7427 | Tubulin beta-4 chain | Mouse | Q8D6F8 | Q13509 |
| | Mr 37000 pl 5.5 | Tubulin alpha-1 chain | Mouse | P02551 | P05209 |
| | | Ubiquinol-cytochrome C reductase complex core protein I, mitochondrial precursor | Mouse | Q9CZ13 | P31930 |
| | | Neurofilament triplet M protein | Mouse | P08553 | P07197 |
| | | Mu-crystallin homolog | Mouse | O54983 | Q14894 |
| tw,wt and tt vs ww | 372 | Dihydropyrimidinase related protein-2 (DRP-2) | Rat | P47942 | Q16555 |
| | 1566 Mr 32000 pl 5.7 | Apolipoprotein E precursor (Apo-E) | Mouse | P08226 | P02649 |
| | | Neurofilament triplet L protein | Mouse | P08551 | P07196 |
| | | ATPase, H+ transporting, lysosomal | Mouse | gi\|20882559 | ? |
| | | Alpha enolase | Rat | Q9W7L1 | ? |

Fig. 9I

| | | | |
|---|---|---|---|
| | Creatine kinase, B chain | Mouse | Q04447 | P12277 |
| | Neurofilament triplet M protein | Mouse | P08553 | P07197 |
| | Voltage-dependent anion-selective channel protein 2 | Mouse | Q60930 | P45880 |
| | RIKEN cDNA 4732495G21 gene | Mouse | gi\|30425250 | ? |
| 696 | Glycerol-3-phosphate dehydrogenase | Mouse | Q64521 | P43304 |
| Mr 50000 pI 6.1 | Lamin B2 | Mouse | P21619 | Q03252 |
| | Dihydropyrimidinase related protein-2 (DRP-2) | Mouse | O08553 | Q16555 |
| | Lamin B3 | Mouse | P48680 | ? |

Fig. 9J

| Peak | Av. Mass | Corresponding LC/MS/MS Analysis |
|---|---|---|
| P5 | 8833 | TT28 |

| Proteins Identified in TT28 | Tolerance (± Da) on BioLynx peptide searches | Mascot Peptide Residue No's | Predicted BioLynx Equivalent Swiss-Prot Residue No's |
|---|---|---|---|
| Full-length haemoglobin alpha chain | 2 & 3 | 1-11 | No match |
| | | 17-31 | 14-97 |
| | | 32-40 | 14-97; 25-107 |
| | | 41-56 | 35-117; 25-107; 14-97 |
| | | 93-99 | 35-117; 45-128; 25-107 |
| | | 128-139 | No match |
| Full-length haemoglobin beta 1 chain | All 2 Da except + (= 3 Da tolerance) | 31-40 | 5-87; 9-91; 6-88; 12-93; 28-107; 29-108; 16-97 |
| | | 41-59 | 5-87; 9-91; 6-88; 12-93; 28-107; 29-108; 16-97+ |
| | | 66-82 | 5-87; 9-91; 6-88; 12-93; 28-107; 29-108; 16-97+ |
| | | 96-104 | 28-107; 29-108 |
| Full-Length Major urinary proteins 11 and 8 (Fragment) | 2 | 29-44 | 20-95; 23-98; 24-99; 2-77; 22-97 |
| | | 135-145 | No match |
| | 3 | 29-44 | 20-95; 23-98; 24-99; 2-77; 22-97; 27-102; 28-103 |
| | | 135-145 | No match |
| Mature Major urinary protein 1 | 2 | 58-73 | 49-124; 3-79; 52-127; 53-128; 31-106; 51-126; 4-80 |
| | | 164-174 | No match |
| | 3 | 58-73 | 49-124; 3-79; 52-127; 53-128; 31-106; 51-126; 4-80; 56-131; 57-132 |
| | | 164-174 | No match |

Fig. 10e-A

| Proteins Identified in TT28 | Tolerance (± Da) on BioLynx peptide searches | Mascot Peptide Residue No's | Predicted BioLynx Equivalent Swiss-Prot Residue No's |
|---|---|---|---|
| Proline-rich protein 4 (HUMAN) | 2 | 107-120 | 58-134 |
|  | 3 | 107-120 | 58-134 |
| Mature albumin | 2 & 3 | 45-57 | No match |
|  | 2 | 58-73 | 49-124; 3-79; 52-127; 53-128; 31-106; 51-126; 4-80 |
|  |  | 164-174 | No match |
| Mature Major urinary protein 6 | 3 | 58-73 | 49-124; 3-79; 52-127; 53-128; 31-106; 51-126; 4-80; 56-131; 57-132; |
|  |  | 164-174 | No match |
| Full-Length Heat shock protein HSP 90-beta | 2 & 3 | 652-678 | No match |
| Full Length Mitochondrial inner membrane protein | 2 & 3 | 46-66 | 15-97; 41-124 |

Fig. 10e-B

| Peak | Av. Mass | Corresponding LC/MS/MS Analysis |
|---|---|---|
| P6 | 9171 | TT28 |

| Proteins Identified in TT28 | Tolerance (± Da) on BioLynx peptide searches | Mascot Peptide Residue No's | Predicted BioLynx Equivalent Swiss-Prot Residue No's |
|---|---|---|---|
| Full-length haemoglobin alpha chain | 2 | 1-11 | No match |
| | | 17-31 | No match |
| | | 32-40 | No match |
| | | 41-56 | No match |
| | | 93-99 | 55-141 |
| | | 128-139 | 55-141 |
| | 3 | 1-11 | No match |
| | | 17-31 | 4-91 |
| | | 32-40 | 4-91 |
| | | 41-56 | 4-91 |
| | | 93-99 | 55-141 |
| | | 128-139 | 55-141 |
| Full-length haemoglobin beta 1 chain | 2 | 31-40 | No match |
| | | 41-59 | No match |
| | | 66-82 | 45-130 |
| | | 96-104 | 45-130 |
| | 3 | 31-40 | 11-95 |
| | | 41-59 | 11-95 |
| | | 66-82 | 45-130 |
| | | 96-104 | 45-130 |

Fig. 10f-A

| Proteins Identified in TT28 | Tolerance (± Da) on BioLynx peptide searches | Mascot Peptide Residue No's | Predicted BioLynx Equivalent Swiss-Prot Residue No's |
|---|---|---|---|
| Full-Length Major urinary proteins 11 and 8 (Fragment) | 2 & 3 | 29-44 | No match |
| | 3 only | 135-145 | 68-146⁺ |
| Mature Major urinary protein 1 | 2 & 3 Da except⁺ (= 3 Da tolerance only) | 58-73 | 11-90; 21-100⁺ |
| | 2 & 3 | 164-174 | No match |
| Mature Major urinary protein 6 | 2 & 3 Da except⁺ (= 3 Da tolerance only) | 58-73 | 11-90; 21-100⁺ |
| | 3 only | 164-174 | 97-175⁺ |
| Proline-rich protein 4 (HUMAN) | 2 | 107-120 | 39-120 |
| | 3 | 107-120 | 39-120 |
| Mature albumin | 3 only | 45-57 | 23-103; 27-107 |
| Full-Length Heat shock protein HSP 90-beta* | 2 & 3 | 652-678 | 620-701; 615-695; 613-693; 603-682; 602-681 |
| Full Length Mitochondrial inner membrane protein | 2 | 46-66 | 12-98 |
| | 3 | 46-66 | 12-98; 7-94; 26-112 |
| Full-length haemoglobin beta 1 chain | 3 only | 31-40 | 11-95 |
| | 3 only | 41-59 | 11-95 |
| | 2 & 3 Da except⁺ (= 3 Da tolerance only) | 66-82 | 11-95⁺; 45-130 |
| | 2 & 3 | 96-104 | 45-130 |
| Full Length Mitochondrial inner membrane protein | 3 only | 46-66 | 7-94; 26-112 |

Fig. 10f-B

| Peak | Av. Mass | Corresponding LC/MS/MS Analysis |
|---|---|---|
| P1 | 3770 | TT32; TT43 |

| Proteins Identified in TT32 & TT43 | Tolerance (± Da) on BioLynx peptide searches | Mascot Peptide Residue No's | Predicted BioLynx Equivalent Swiss-Prot Residue No's |
|---|---|---|---|
| Mature albumin | 2 | 45-57 | No match |
| | | 45-57 | No match |
| | | 550-558 | No match |
| | 3 | 45-57 | No match |
| | | 45-57 | No match |
| | | 550-558 | No match |
| Mature Alpha-1-antitrypsin 1-2 | 2 | 385-406 | 375-406; 376-407 |
| | | 385-406 | 375-406; 376-407 |
| | 3 | 385-406 | 375-406; 376-407; 379-410 |
| | | 385-406 | 375-406; 376-407; 379-410 |
| Mature Alpha-1-antitrypsin 1-6 | 2 | 385-406 | No match |
| | | 385-406 | No match |
| | 3 | 385-406 | 379-410 |
| | | 385-406 | 379-410 |
| Mature Alpha-1-antitrypsin 1-4 | 2 | 385-406 | No match |
| | | 385-406 | No match |
| | 3 | 385-406 | No match |
| | | 385-406 | No match |
| Mature Alpha-1-antitrypsin 1-3 | 3 | 385-406 | No match |
| | | 385-406 | No match |

Fig. 10g-A

| Peak | Av. Mass | Corresponding LC/MS/MS Analysis |
|---|---|---|
| P4 | 8618 | TT28; TT41 |

| Proteins Identified in TT28 & TT41 | Tolerance (± Da) on BioLynx peptide searches | Mascot Peptide Residue No's | Predicted BioLynx Equivalent Swiss-Prot Residue No's |
|---|---|---|---|
| Mature Major urinary protein 1 | 2 | 58-73 | 22-96 |
| | | 164-174 | No match |
| | | 164-174 | No match |
| | 3 | 58-73 | 22-96; 7-81 |
| | | 164-174 | No match |
| | | 164-174 | No match |
| Full-Length Major urinary proteins 11 and 8 (Fragment) | 2 | 29-44 | No match |
| | | 135-145 | 70-144 |
| | | 135-145 | 70-144 |
| | 3 | 29-44 | No match |
| | | 135-145 | 70-144 |
| | | 135-145 | 70-144 |
| Mature Major urinary protein 6 | 2 | 58-73 | 22-96 |
| | | 164-174 | No match |
| | | 164-174 | No match |
| | 3 | 58-73 | 22-96; 7-81 |
| | | 164-174 | No match |
| | | 164-174 | No match |
| Mature albumin | 2 | 45-57 | No match |
| | | 550-558 | No match |
| | 3 | 45-57 | No match |
| | | 550-558 | No match |

Fig. 10g-B

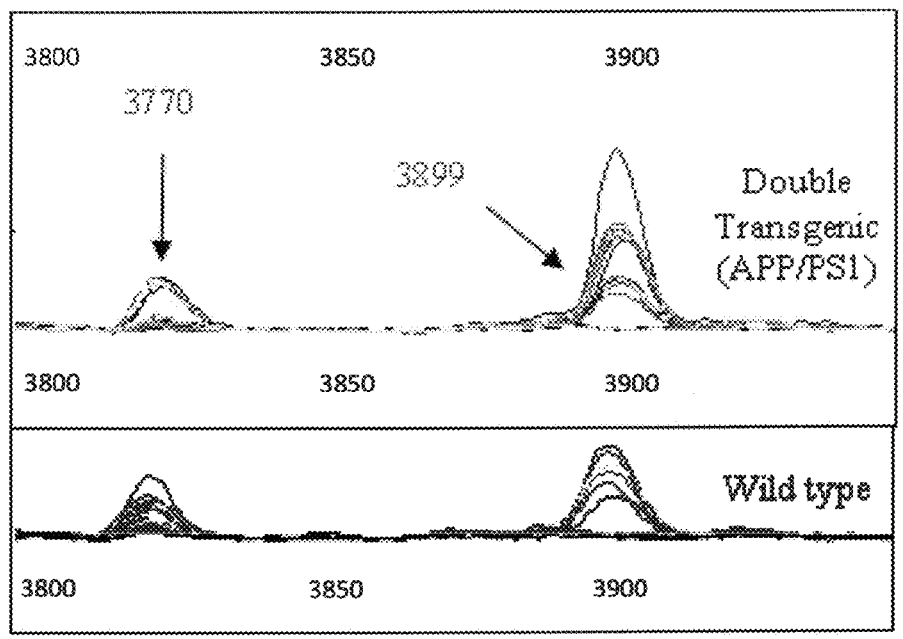
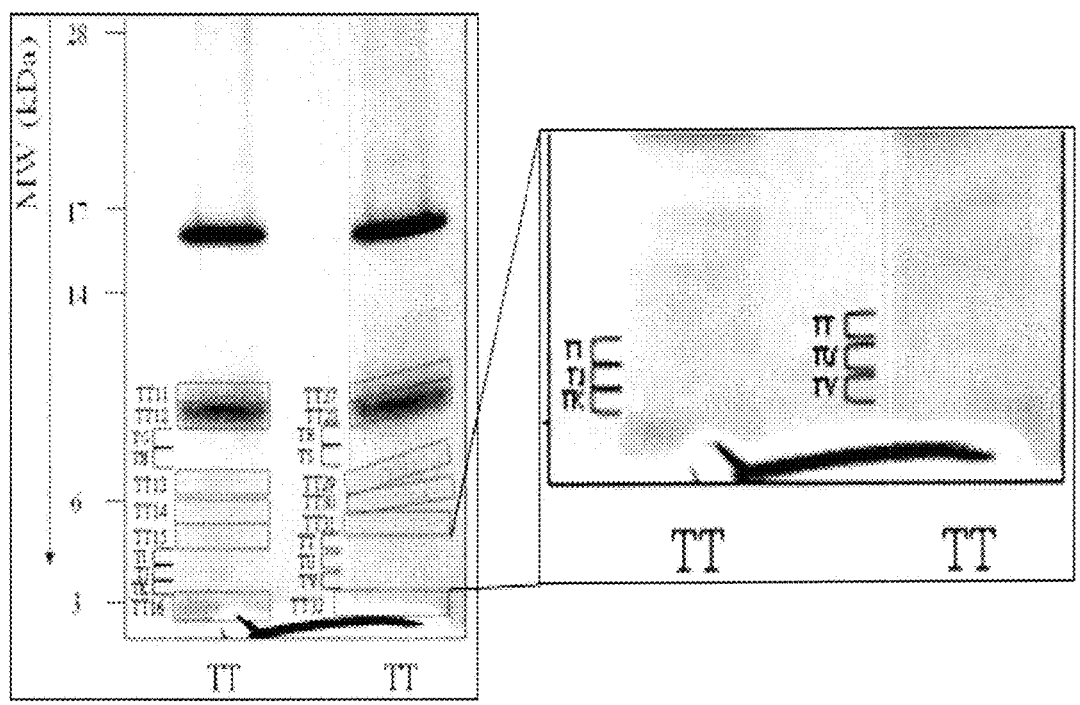
Fig. 11a-A

P1 3770: 149-180 ; TT43 (TK, TV)

Major urinary protein 1 precursor (MUP 1) MOUSE
Average Mass = 20648.5258, Monoisotopic Mass = 20635.2697
N-Terminus = H, C-Terminus = OH 1   MKMLL LLCLG LTLVC VHAEE ASSTG RNFNV EKING EWHTI ILASD KREKI EDNGN FRLFL EQIHV LENSL VLKFH TVRDE ECSEL SMVAD KTEDA GRYSV TYDGF NTFTI
111 PKTDY DNFLM AHLIN EKDGE TFQLM GLYGR EPDLS SDI

P2 3899: 142-175 ; TT43 (TJ, TU, TI, TT)

Major urinary protein 1 precursor (MUP 1) MOUSE
Average Mass = 20648.5258, Monoisotopic Mass = 20635.2697
N-Terminus = H, C-Terminus = OH 1   MKMLL LLCLG LTLVC VHAEE ASSTG RNFNV EKING EWHTI ILASD KREKI EDNGN FRLFL EQIHV LENSL VLKFH TVRDE ECSEL SMVAD KTEDA GRYSV TYDGF NTFTI
111 PKTDY DNFLM AHLIN EKDGE TFQLM GLYGR E         LQMRL

Fig. 11a-B

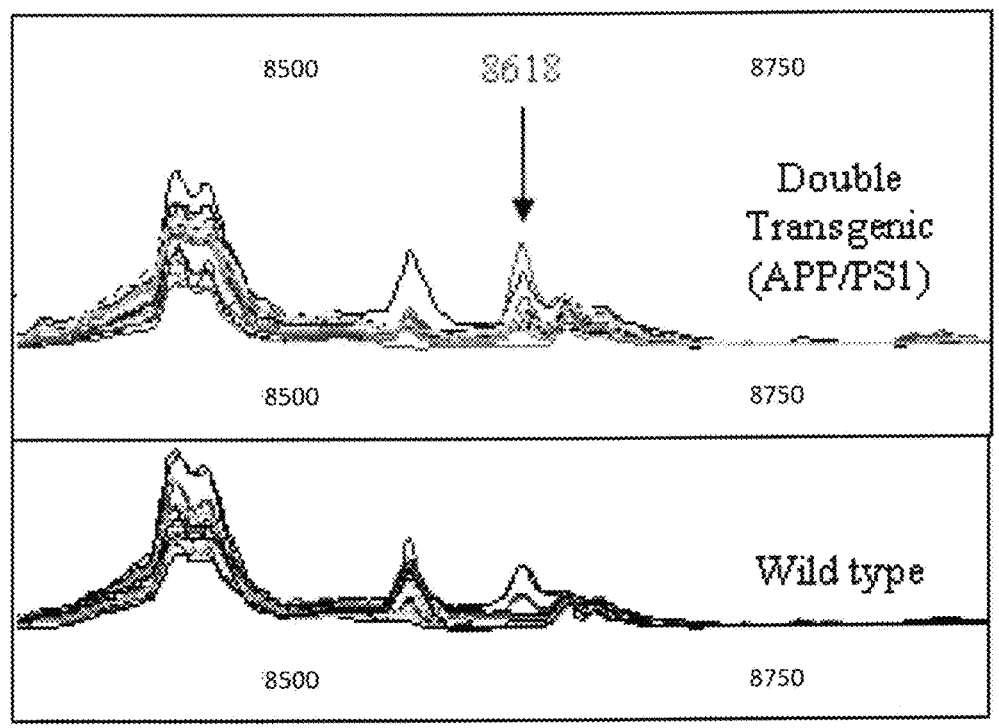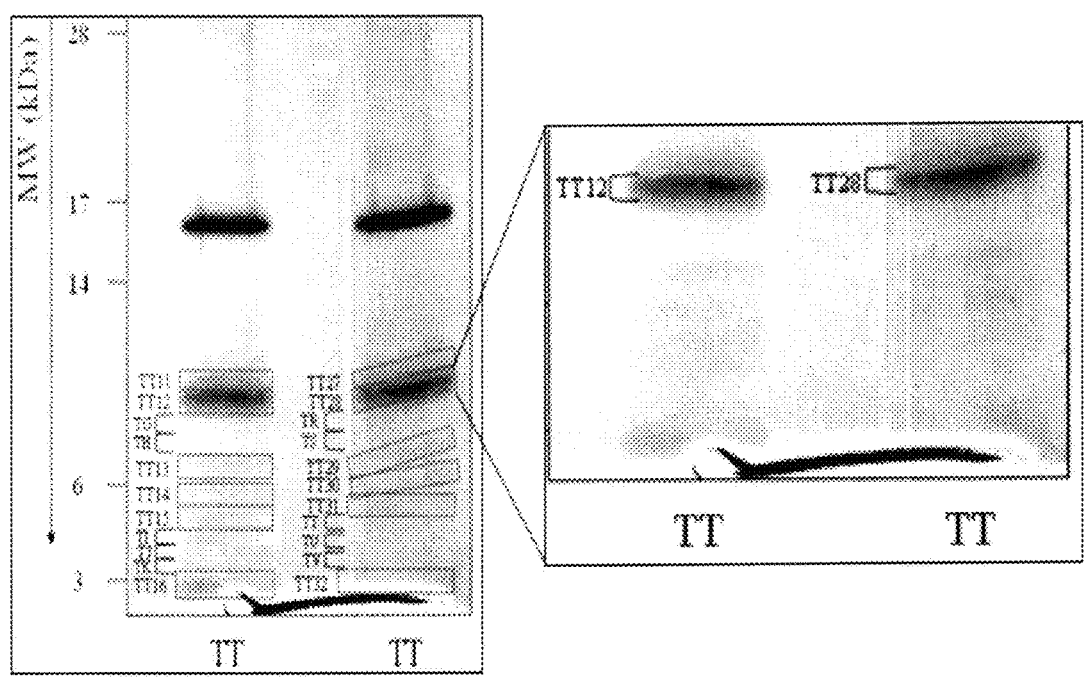
Fig. 11b-A

P4 8618: 22-96 ; TT28 (TT12, TT28)

Major urinary protein 1 precursor (MUP 1) MOUSE
Average Mass = 20848.5258, Monoisotopic Mass = 20835.2697
N-Terminus = H, C-Terminus = OH

*1   MKMLL LLCLG LTLVC VHAEE ▓▓▓▓▓ ▓▓▓▓▓ ▓▓▓▓▓ ▓▓▓▓▓ ▓▓▓▓▓ ▓▓▓▓▓
111  PKTDY DNFLM RHLIN EKDGE TFQLM GLYGR EPDLS SDIKE RFAQL CEKHG ILREN IIDLS NANRC LQARE ▓▓▓▓▓ ▓▓▓▓▓ ▓▓▓▓▓ RYSV TYDGF NTFTI

SEQUENCE LISTING

```
<160> NUMBER OF SEQ ID NOS: 110

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Tyr Ile Ala Thr Pro Ile Phe Ser Lys
 1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 2

Asn Leu Ser Thr Phe Ala Val Asp Gly Lys
 1               5                  10
```

```
<210> SEQ ID NO 3
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 3

Asp Tyr Leu Gly Asp Phe Ile Glu His Tyr Ala Gln Leu Gly Pro Ser
 1               5                  10                  15

Gln Pro Pro Asp Leu Ala Gln Ala Gln Asp Glu Pro Arg
             20                  25

<210> SEQ ID NO 4
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 4

Gly Pro Gly Leu Gly Ser Thr Gln Gly Gln Thr Ile Ala Leu Pro Ala
 1               5                  10                  15

Gln Gly Leu Ile Glu Phe Arg
             20

<210> SEQ ID NO 5
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 5

Leu Ile Asp Asp Tyr Gly Val Glu Glu Glu Pro Ala Glu Leu Pro Glu
 1               5                  10                  15

Gly Thr Ser Leu Thr Val Asp Asn Lys Arg
             20                  25

<210> SEQ ID NO 6
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 6

Gly Gly Pro Leu Ser Asp Ser Tyr Arg
 1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 7

Ile Gly Pro Ala Ser Gln Gly Leu Gln Lys
 1               5                  10

<210> SEQ ID NO 8
<211> LENGTH: 16
<212> TYPE: PRT
<213> ORGANISM: Artificial Sequence
<220> FEATURE:
```

-continued

<223> OTHER INFORMATION: Synthetic Sequence

<400> SEQUENCE: 8

Ala Val Gln Gln Pro Asp Gly Leu Ala Val Leu Gly Ile Phe Leu Lys
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 9

Asn Leu Asp Ile Glu Arg Pro Thr Tyr Thr Asn Leu Asn Arg
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 10

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 11
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 11

Ser Ile Gln Phe Val Asp Trp Cys Pro Thr Gly Phe Lys
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 12

Val Gly Ile Asn Tyr Gln Pro Pro Thr Val Val Pro Gly Gly Asp Leu
1               5                   10                  15

Ala Lys

<210> SEQ ID NO 13
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 13

Val Val Ser Pro Trp Asn Ser Glu Asp Ala Lys
1               5                   10

<210> SEQ ID NO 14
<211> LENGTH: 16

```
<212> TYPE: PRT
<213> ORGANISM: Artificial Sequence
<220> FEATURE:
<223> OTHER INFORMATION: Synthetic Sequence

<400> SEQUENCE: 14

Ile Met Glu Gly Pro Ala Phe Asn Phe Leu Asp Ala Pro Ala Val Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 15

Ser Tyr Glu Leu Pro Asp Gly Gln Val Ile Thr Ile Gly Asn Glu Arg
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 16

Trp Ala Leu Ser Gln Ser Asn Pro Ser Ala Leu Arg
1               5                   10

<210> SEQ ID NO 17
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 17

Glu Thr Val Val Glu Val Pro Gln Val Thr Trp Glu Asp Ile Gly Gly
1               5                   10                  15

Leu Glu Asp Val Lys Arg
            20

<210> SEQ ID NO 18
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 18

Ala Leu Tyr Asp Phe Glu Pro Glu Asn Glu Gly Glu Leu Gly Phe Lys
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 19

Ala Ala Val Glu Glu Gly Ile Val Leu Gly Gly Gly Cys Ala Leu Leu
1               5                   10                  15

Arg
```

```
<210> SEQ ID NO 20
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 20

Asp Val Asp Leu Glu Phe Leu Ala Lys
 1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 21

Leu Asp Gln Leu Ile Tyr Ile Pro Leu Pro Asp Glu Lys
 1               5                  10

<210> SEQ ID NO 22
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 22

Gln Ala Ala Pro Cys Val Leu Phe Phe Asp Glu Leu Asp Ser Ile Ala
 1               5                  10                  15

Lys

<210> SEQ ID NO 23
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 23

Ala Glu Glu Asp Val Ala Ala Leu Val Ile Asp Asn Gly Ser Gly Met
 1               5                  10                  15

Cys Lys

<210> SEQ ID NO 24
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 24

Val Ala Pro Glu Glu His Pro Val Leu Leu Thr Glu Ala Pro Leu Asn
 1               5                  10                  15

Pro Lys

<210> SEQ ID NO 25
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 25
```

```
Val Ala Leu Thr Gly Leu Thr Val Ala Glu Tyr Phe Arg Asp Gln Glu
1               5                   10                  15

Gly Gln Asp Val Leu Leu Phe Ile Asp Asn Ile Phe Arg
            20                  25
```

<210> SEQ ID NO 26
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 26

```
Ile Leu Gly Ala Asp Thr Ser Val Asp Leu Glu Glu Thr Gly Arg
1               5                   10                  15
```

<210> SEQ ID NO 27
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 27

```
Val Leu Ser Ile Gly Asp Gly Ile Ala Arg
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 28

```
Val Val Asp Ala Leu Gly Asn Ala Ile Asp Gly Lys
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 29

```
Ile Cys Val Leu Asp Val Asp Leu Gln Gly Val Arg
1               5                   10
```

<210> SEQ ID NO 30
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 30

```
Phe Glu Asp Gly Asp Leu Thr Leu Tyr Gln Ser Asn Ala Ile Leu Arg
1               5                   10                  15
```

<210> SEQ ID NO 31
<211> LENGTH: 24
<212> TYPE: PRT
<213> ORGANISM: Artificial Sequence
<220> FEATURE:
<223> OTHER INFORMATION: Synthetic Sequence

```
<400> SEQUENCE: 31

Thr Asp Asp Glu Val Val Gln Arg Glu Glu Ala Ile Gln Leu Asp
 1               5                  10                  15

Gly Leu Asn Ala Ser Gln Ile Arg
            20

<210> SEQ ID NO 32
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 32

Gly Val Val Asp Ser Asp Asp Leu Pro Leu Asn Val Ser Arg
 1               5                  10

<210> SEQ ID NO 33
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 33

Ile Tyr Asp Asp Asp Phe Phe Gln Asn Leu Asp Gly Val Ala Asn Ala
 1               5                  10                  15

Leu Asp Asn Ile Asp Ala Arg
            20

<210> SEQ ID NO 34
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 34

Leu Ala Gly Thr Gln Pro Leu Glu Val Leu Glu Ala Val Gln Arg
 1               5                  10                  15

<210> SEQ ID NO 35
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 35

Ala Ala Val Ala Ser Leu Leu Gln Ser Val Gln Val Pro Glu Phe Thr
 1               5                  10                  15

Pro Lys

<210> SEQ ID NO 36
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 36

Thr Thr Pro Ser Val Val Ala Phe Thr Ala Asp Gly Glu Arg
 1               5                  10

<210> SEQ ID NO 37
```

```
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 37

Gln Ala Val Thr Asn Pro Asn Asn Thr Phe Tyr Ala Thr Lys
 1               5                  10

<210> SEQ ID NO 38
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 38

Glu Ile Leu Gln Glu Glu Glu Asp Leu Ala Glu Ile Val Gln Leu Val
 1               5                  10                  15

Gly Lys

<210> SEQ ID NO 39
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 39

Val Ser Leu Asp Val Asn His Phe Ala Pro Asp Glu Leu Thr Val Lys
 1               5                  10                  15

<210> SEQ ID NO 40
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 40

Thr Leu Val Thr Gln Asn Ser Gly Val Glu Ala Leu Ile His Ala Ile
 1               5                  10                  15

Leu Arg

<210> SEQ ID NO 41
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 41

Gly Val Val Asp Ser Asp Asp Leu Pro Leu Asn Val Ser Arg
 1               5                  10

<210> SEQ ID NO 42
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 42

Gly Asn Asp Met Gln Val Gly Thr Tyr Ile Glu Lys
 1               5                  10
```

```
<210> SEQ ID NO 43
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 43

Ile Leu Gln Asp Ile Ala Ser Gly Arg
 1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 44

Gly Val Asn Val Ser Ala Leu Ser Arg
 1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 45

Thr Val Ile Ser Gln Ser Leu Ser Lys
 1               5

<210> SEQ ID NO 46
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 46

Thr Ala Leu Val Ala Asn Thr Ser Asn Met Pro Val Ala Ala Arg
 1               5                  10                  15

<210> SEQ ID NO 47
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 47

Leu Ala Glu Met Pro Ala Asp Ser Gly Tyr Pro Ala Tyr Leu Gly Ala
 1               5                  10                  15

Arg

<210> SEQ ID NO 48
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 48

Leu Ala Ser Phe Tyr Glu Arg
 1               5
```

```
<210> SEQ ID NO 49
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 49

Glu Phe Ser Gly Tyr Val Glu Ser Gly Leu Lys
 1               5                  10

<210> SEQ ID NO 50
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 50

Ser Glu Ile Asp Leu Val Gln Ile Lys
 1               5

<210> SEQ ID NO 51
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 51

Thr Ala Ser Leu Thr Ser Ala Ala Ser Ile Asp Gly Ser Arg
 1               5                  10

<210> SEQ ID NO 52
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 52

Val Ala Pro Glu Glu His Pro Val Leu Leu Thr Glu Ala Pro Leu Asn
 1               5                  10                  15

Pro Lys

<210> SEQ ID NO 53
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 53

Gly Tyr Ser Phe Thr Thr Thr Ala Glu Arg
 1               5                  10

<210> SEQ ID NO 54
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 54

Ser Tyr Glu Leu Pro Asp Gly Gln Val Ile Thr Ile Gly Asn Glu Arg
 1               5                  10                  15
```

```
<210> SEQ ID NO 55
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 55

Glu Ile Thr Ala Leu Ala Pro Ser Thr Met Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 56

Ala Thr Asp Ala Glu Ala Asp Val Ala Ser Leu Asn Arg
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 57

Tyr Phe Leu His Gln Ser His Glu Glu Arg
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 58

Ile Phe Leu Gln Asp Ile Lys
1               5

<210> SEQ ID NO 59
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 59

Ile Cys Val Leu Asp Val Asp Leu Gln Gly Val Arg
1               5                   10

<210> SEQ ID NO 60
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 60

Glu Lys Pro Glu Leu Gln Phe Pro Phe Leu Gln Asp Glu Asp Thr Val
1               5                   10                  15

Ala Thr Leu His Glu Cys Lys
            20
```

```
<210> SEQ ID NO 61
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 61

Ala His Val Thr Leu Gly Cys Ala Ala Asp Val Gln Pro Val Gln Thr
1               5                   10                  15

Gly Leu Asp Leu Leu Asp Ile Leu Gln Gln Val Lys
            20                  25

<210> SEQ ID NO 62
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 62

Gly Gly Ser Gln Gly Glu Ala Val Gly Glu Leu Pro Arg
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 63

Thr Pro Ile Gly Ser Phe Leu Gly Ser Leu Ala Ser Gln Pro Ala Thr
1               5                   10                  15

Lys

<210> SEQ ID NO 64
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 64

Ile Ala Ala Phe Ala Asp Ala Ala Val Asp Pro Ile Asp Phe Pro Leu
1               5                   10                  15

Ala Pro Ala Tyr Ala Val Pro Lys
            20

<210> SEQ ID NO 65
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 65

Met Ile Glu Glu Ala Gly Ala Ile Ile Ser Thr Arg
1               5                   10

<210> SEQ ID NO 66
<211> LENGTH: 11
<212> TYPE: PRT
<213> ORGANISM: Artificial Sequence
<220> FEATURE:
```

```
<223> OTHER INFORMATION: Synthetic Sequence

<400> SEQUENCE: 66

Ala Thr Leu Trp Tyr Val Pro Leu Ser Leu Lys
 1               5                  10

<210> SEQ ID NO 67
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 67

Val Leu Glu Val Pro Pro Ile Val Tyr Leu Arg
 1               5                  10

<210> SEQ ID NO 68
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 68

Ala Ile Leu Ala Glu Leu Thr Gly Arg
 1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 69

Val Asp Gly Met Asp Ile Leu Cys Val Arg
 1               5                  10

<210> SEQ ID NO 70
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 70

His Thr Glu Ala Ala Ala Ala Gln Arg Glu Glu Trp Lys
 1               5                  10

<210> SEQ ID NO 71
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 71

Phe Gly Glu Val Val Asp Cys Thr Leu Lys
 1               5                  10

<210> SEQ ID NO 72
<211> LENGTH: 8
<212> TYPE: PRT
<213> ORGANISM: Artificial Sequence
<220> FEATURE:
<223> OTHER INFORMATION: Synthetic Sequence
```

```
<400> SEQUENCE: 72

Gly Phe Gly Phe Val Leu Phe Lys
 1               5

<210> SEQ ID NO 73
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 73

Glu Tyr Phe Gly Gly Phe Gly Glu Val Glu Ser Ile Glu Leu Pro Met
 1               5                  10                  15

Asp Asn Lys

<210> SEQ ID NO 74
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 74

Ser Asn Asp Pro Val Ala Leu Ala Phe Ala Glu Met Leu Lys
 1               5                  10

<210> SEQ ID NO 75
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 75

Gln Gln Leu Gly Thr Ala Val Glu Met Glu Ile Ala Gln Met Leu Glu
 1               5                  10                  15

Glu Asn Ser Arg
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 76

Ile Gly Glu His Thr Pro Ser Ala Leu Ala Ile Met Glu Asn Ala Asn
 1               5                  10                  15

Val Leu Ala Arg
            20

<210> SEQ ID NO 77
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 77

Tyr Ala Ser Ile Cys Gln Gln Asn Gly Ile Val Pro Ile Val Glu Pro
 1               5                  10                  15

Glu Ile Leu Pro Asp Gly Asp His Asp Leu Lys Arg
            20                  25
```

```
<210> SEQ ID NO 78
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 78

Phe Ser Asn Glu Glu Ile Ala Met Ala Thr Val Thr Ala Leu Arg Arg
 1               5                  10                  15

<210> SEQ ID NO 79
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 79

Ala Leu Ala Asn Ser Leu Ala Cys Gln Gly Lys
 1               5                  10

<210> SEQ ID NO 80
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 80

Leu Ser Ile Ser Ala Leu Phe Val Thr Pro Lys
 1               5                  10

<210> SEQ ID NO 81
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 81

Ala His Val Thr Leu Gly Cys Ala Ala Asp Val Gln Pro Val Gln Thr
 1               5                  10                  15

Gly Leu Asp Leu Leu Asp Ile Leu Gln Gln Val Lys
             20                  25

<210> SEQ ID NO 82
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 82

Gly Gly Ser Gln Gly Glu Ala Val Gly Glu Leu Pro Arg
 1               5                  10

<210> SEQ ID NO 83
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 83

Gln Leu Ile Thr Asp Leu Val Ile Ser Lys
```

-continued

<210> SEQ ID NO 84
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 84

Glu Met Leu Thr Leu Pro Thr Phe Pro Val Val Val Lys
1               5                   10

<210> SEQ ID NO 85
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 85

Val Glu Asn His Tyr Asp Phe Gln Asp Ile Ala Ser Val Val Ala Leu
1               5                   10                  15

Thr Gln Thr Tyr Ala Thr Ala Glu Pro Phe Ile Asp Ala Lys
            20                  25                  30

<210> SEQ ID NO 86
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 86

Asp Val Thr Glu Val Leu Ile Leu Gln Leu Phe Ser Gln Ile Gly Pro
1               5                   10                  15

Cys Lys

<210> SEQ ID NO 87
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 87

Gln Leu Arg Phe Glu Asp Val Val Asn Gln Ser Ser Pro Lys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 88

Gln Thr Phe Ser Pro Phe Gly Gln Ile Met Glu Ile Arg
1               5                   10

<210> SEQ ID NO 89
<211> LENGTH: 17
<212> TYPE: PRT
<213> ORGANISM: Artificial Sequence
<220> FEATURE:
<223> OTHER INFORMATION: Synthetic Sequence -continued

```
<400> SEQUENCE: 89

Thr Pro Ile Gly Ser Phe Leu Gly Ser Leu Ala Ser Gln Pro Ala Thr
1               5                   10                  15

Lys

<210> SEQ ID NO 90
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 90

Ile Ala Ala Phe Ala Asp Ala Ala Val Asp Pro Ile Asp Phe Pro Leu
1               5                   10                  15

Ala Pro Ala Tyr Ala Val Pro Lys
            20

<210> SEQ ID NO 91
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 91

Phe Ala Ser Glu Ile Thr Pro Ile Thr Ile Ser Val Lys
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 92

Gln Glu Gln Asp Thr Tyr Ala Leu Ser Ser Tyr Thr Arg
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 93

Asn Ile Ala Asn Pro Thr Ala Met Leu Leu Ser Ala Thr Asn Met Leu
1               5                   10                  15

Arg

<210> SEQ ID NO 94
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 94

Ser Asn Asp Pro Val Ala Leu Ala Phe Ala Glu Met Leu Lys
1               5                   10

<210> SEQ ID NO 95
<211> LENGTH: 21
```

```
<212> TYPE: PRT
<213> ORGANISM: Artificial Sequence
<220> FEATURE:
<223> OTHER INFORMATION: Synthetic Sequence

<400> SEQUENCE: 95

Thr Phe Glu Ser Leu Val Asp Phe Cys Lys Leu Leu Val Pro Tyr Leu
1               5                   10                  15

Ile Glu Ala Val Arg
            20

<210> SEQ ID NO 96
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 96

Thr Gly Ala Ile Val Asp Val Pro Val Gly Glu Glu Leu Leu Gly Arg
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 97

Glu Ala Tyr Pro Gly Asp Val Phe Tyr Leu His Ser Arg
1               5                   10

<210> SEQ ID NO 98
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 98

Gln Gly Gln Tyr Ser Pro Met Ala Ile Glu Glu Gln Val Ala Val Ile
1               5                   10                  15

Tyr Ala Gly Val Arg
            20

<210> SEQ ID NO 99
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 99

Tyr Gln Leu Asp Pro Thr Ala Ser Ile Ser Ala Lys Leu Thr Leu Ser
1               5                   10                  15

Ala Leu Val Asp Gly Lys
            20

<210> SEQ ID NO 100
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 100
```

```
Ile Gly Val Thr Val Leu Ser Arg
1               5
```

<210> SEQ ID NO 101
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 101

```
Ala Val Leu Asp Ala Leu Leu Glu Gly Lys
1               5                   10
```

<210> SEQ ID NO 102
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 102

```
Thr Ala Phe Asp Glu Ala Ile Ala Glu Leu Asp Thr Leu Ser Glu Glu
1               5                   10                  15

Ser Tyr Lys Asp Ser Thr Leu Ile Met Gln Leu Leu Arg
            20                  25
```

<210> SEQ ID NO 103
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 103

```
Ala Leu Pro Phe Trp Asn Glu Glu Ile Val Pro Gln Ile Lys
1               5                   10
```

<210> SEQ ID NO 104
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 104

```
Leu Ser Gly Pro Gly Gly Ser Gly Ser Phe Arg Ala Leu Glu Ala Glu
1               5                   10                  15

Leu Ala Ala Leu Arg
            20
```

<210> SEQ ID NO 105
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 105

```
Val Leu Glu Ala Glu Leu Leu Val Leu Arg Ile Asp Ser Leu Met Asp
1               5                   10                  15

Glu Ile Ala Phe Leu Lys
            20
```

<210> SEQ ID NO 106

```
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 106

Glu Ile Leu Gln Glu Glu Glu Asp Leu Ala Glu Ile Val Gln Leu Val
 1               5                  10                  15

Gly Lys

<210> SEQ ID NO 107
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 107

Ala Ala Val Pro Ser Gly Ala Ser Thr Gly Ile Tyr Glu Ala Leu Glu
 1               5                  10                  15

Leu Arg

<210> SEQ ID NO 108
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 108

Val Gln Ser Leu Gln Asp Glu Val Ala Phe Leu Arg
 1               5                  10

<210> SEQ ID NO 109
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 109

Leu Thr Leu Ser Ala Leu Val Asp Gly Lys
 1               5                  10

<210> SEQ ID NO 110
<211> LENGTH: 180
<212> TYPE: PRT
<213> ORGANISM: murine

<400> SEQUENCE: 110

Met Lys Met Leu Leu Leu Leu Cys Leu Gly Leu Thr Leu Val Cys Val
 1               5                  10                  15

His Ala Glu Glu Ala Ser Ser Thr Gly Arg Asn Phe Asn Val Glu Lys
             20                  25                  30

Ile Asn Gly Glu Trp His Thr Ile Ile Leu Ala Ser Asp Lys Arg Glu
         35                  40                  45

Lys Ile Glu Asp Asn Gly Asn Phe Arg Leu Phe Leu Glu Gln Ile His
     50                  55                  60

Val Leu Glu Asn Ser Leu Val Leu Lys Phe His Thr Val Arg Asp Glu
 65                  70                  75                  80

Glu Cys Ser Glu Leu Ser Met Val Ala Asp Lys Thr Glu Lys Ala Gly
                 85                  90                  95
```

```
Glu Tyr Ser Val Thr Tyr Asp Gly Phe Asn Thr Phe Thr Ile Pro Lys
            100             105             110

Thr Asp Tyr Asp Asn Phe Leu Met Ala His Leu Ile Asn Glu Lys Asp
            115             120             125

Gly Glu Thr Phe Gln Leu Met Gly Leu Tyr Gly Arg Glu Pro Asp Leu
        130             135             140

Ser Ser Asp Ile Lys Glu Arg Phe Ala Gln Leu Cys Glu Lys His Gly
145             150             155             160

Ile Leu Arg Glu Asn Ile Ile Asp Leu Ser Asn Ala Asn Arg Cys Leu
                165             170             175

Gln Ala Arg Glu
            180
```

METHODS AND COMPOSITIONS RELATING TO ALZHEIMER'S DISEASE

FIELD OF INVENTION

The present invention relates to methods and compositions relating to Alzheimer's disease. Specifically, the present invention identifies and describes proteins that are differentially expressed in Alzheimer's disease as compared to the normal state. Still further, the present invention provides methods, particularly experimental paradigms, for the identification of differential expressed proteins that are potential molecular targets for compounds to treat or prevent Alzheimer's disease. Still further, the present invention provides methods for the identification and therapeutic use of compounds for the prevention and treatment of Alzheimer's disease.

BACKGROUND OF INVENTION

Alzheimer's disease (AD), the most common cause of dementia in older individuals, is a debilitating neurodegenerative disease for which there is currently no cure. It destroys neurons in parts of the brain, chiefly the hippocampus, which is a region involved in coding memories. Alzheimer's disease gives rise to an irreversible progressive loss of cognitive functions and of functional autonomy. The earliest signs of AD may be mistaken for simple forgetfulness, but in those who are eventually diagnosed with the disease, these initial signs inexorably progress to more severe symptoms of mental deterioration. While the time it takes for AD to develop will vary from person to person, advanced signs include severe memory impairment, confusion, language disturbances, personality and behaviour changes, and impaired judgement. Persons with AD may become non-communicative and hostile. As the disease ends its course in profound dementia, patients are unable to care for themselves and often require institutionalisation or professional care in the home setting. While some patients may live for years after being diagnosed with AD, the average life expectancy after diagnosis is eight years.

In the past, AD could only be definitively diagnosed by brain biopsy or upon autopsy after a patient died. These methods, which demonstrate the presence of the characteristic plaque and tangle lesions in the brain, are still considered the gold standard for the pathological diagnoses of AD. However, in the clinical setting brain biopsy is rarely performed and diagnosis depends on a battery of neurological, psychometric and biochemical tests, including the measurement of biochemical markers such as the ApoE and tau proteins or the beta-amyloid peptide in cerebrospinal fluid and blood.

Although many drugs are commonly used to treat behavioural symptoms (aggression, paranoia, delusions, or depression) associated with AD, only four drugs (known as cholinesterase inhibitors) are available to help improve cognitive function in persons diagnosed with AD. These drugs Cognex (tacrine), Aricept (donepezil), Exelon (rivastigmine) and Reminyl (galantamine) provide symptomatic benefits only—they have not been shown to alter the course of the disease.

SUMMARY OF THE INVENTION

Broadly, the present invention relates to work to identify protein markers associated with Alzheimer's disease, and the use of these markers for the diagnosis or prognosis of AD. The present invention further relates to the use of these proteins as therapeutic targets and to methods of screening candidate compounds to determine whether they are likely to be useful in the treatment of AD or in the development of lead compounds for the treatment of AD. The experiments described herein looked at differential expression of proteins in normal mice as compared to a mouse model of Alzheimer's disease expressing an amyloid precursor protein gene (APP) and/or presenilin-1 (PS-1) double transgenic mouse.

Accordingly, in a first aspect, the present invention provides a method of diagnosing Alzheimer's disease in a patient, the method comprising determining the presence or amount of one or more of the proteins set out in FIGS. 3 to 6 or Table 7 or corresponding human proteins as set out in FIG. 9 in a sample from a patient.

In a further aspect, the present invention provides the use of the presence or amount of one or more of the proteins set out in FIGS. 3 to 6 or Table 7 or corresponding human proteins as set out in FIG. 9 for the diagnosis of Alzheimer's disease using a sample from a patient.

In a further aspect, the present invention provides the use of a protein as set out in FIGS. 3 to 6, Table 7 or corresponding human protein as set out in FIG. 9 for screening candidate compounds for their suitability as agents for to treat or prevent Alzheimer's disease.

In a further aspect, the present invention provides a method of screening for compounds potentially useful in the prevention or treatment of Alzheimer's disease, the method comprising:

determining whether one or more candidate compounds is capable of modulating the expression or level of one or more of the proteins set out in FIGS. 3 to 6 or Table 7 or corresponding human proteins as set out in FIG. 9.

In a further aspect, the present invention provides a method of screening an agent to determine its usefulness in treating Alzheimer's disease, the method comprising:

(a) establishing a paradigm in which at least one protein is differentially expressed in relevant tissue from, or representative of, subjects having or having a predisposition to Alzheimer's disease and normal subjects;

(b) obtaining a sample of relevant tissue taken from, or representative of, a subject having Alzheimer's disease, who or which has been treated with the agent being screened;

(c) determining the presence, absence or degree of expression of the differentially expressed protein or proteins in the tissue from, or representative of, the treated subject; and, (d) selecting or rejecting the agent according to the extent to which it changes the expression, activity or amount of the differentially expressed protein or proteins in the treated subject having Alzheimer's disease towards that of a normal subject.

The paradigm may involve establishing at least one protein which is differentially expressed. However, in some embodiments, the paradigm may employ at least 2, 3, 4, 5, 6, 7, 8, 9, 10 or 20 differentially expressed proteins.

Preferably, in this method, the agent is selected if it converts the expression of the protein or proteins to that of the normal subject. Examples of differentially expressed proteins that may be employed in the method of screening are provided in FIGS. 3 to 6 and FIG. 9 and Table 7 and include guanosine diphosphate dissociation inhibitor 1, dihydropyrimidinease related protein-2, proteasome subunit alpha type 6, apolipoprotein E, synapsin II, ubiquitin carboxyl-terminal hydrolase isozyme L1, aspartate aminotransferase, glutathione S-transferase mu 1, tubulin beta-4 chain, WW domain binding protein 2, eukaryotic translation initiation factor 4H, tubulin beta-3, neuronal protein Np25, fructose-bisphosphate aldolase A, fructose-bisphosphate aldolase C, nucleolysin TIA related protein, peptidylprolyl isomerase D, voltage-dependent anion-selective channel protein 1 and acetyl-COA acetyltransferase mitochondrial precursor.

Reference to proteins listed in the figures and tables herein includes processed forms (eg mature proteins generated by cleavage of precursor forms, for example by removal of a signal peptide). The amino acid residues corresponding to the processed forms are provided in the SWISS-PROT or other database entries given in the figure or table.

By way of example, the paradigm may be based on (a) samples from an amyloid precursor protein (APP) and presenilin-1 (PS-1) double transgenic mouse and a wild-type mouse, and/or (b) samples from a single transgenic APP mouse and/or a single transgenic PS-1 mouse. The paradigm may also employ samples from another animal model of AD. Preferred samples are tissue samples, for example serum samples, or most usefully brain tissue samples such as hippocampus, hemisphere or cingulate cortex tissue.

In some embodiments, in the paradigm, the subjects having differential levels of protein expression comprise:
(a) wild-type mice and transgenic mice as described above; and,
(b) transgenic mice as described above which have not been treated with the agent and transgenic mice as described above which have been treated with the agent.

Preferably the differential levels of protein expression are not observed in wild-type mice which have and have not been treated with the agent.

Additionally or alternatively, in the paradigm, the subjects having differential levels of protein expression comprise:
(a) wild-type mice who have and have not been treated with the agent; and,
(b) transgenic mice as described above who have and have not been treated with the agent.

In this case, the differential levels of protein expression are not observed in wild-type or transgenic mice which are not treated with the agent.

In all aspects of the invention the proteins present in a sample can be established using two-dimensional gel electrophoresis or SELDI analysis carried out on the relevant tissue or a protein-containing extract thereof. The proteins may be isolated as outlined below and further analysed for identification. Proteins can typically be identified using mass spectrometry to analyse said protein and a database search.

Differential expression may be confirmed using statistical analysis of, for example, intensities of spots on 2D gels or of SELDI peaks. Statistical analysis may include Statistical analysis may include univariate methods such as the Mann-Whitney test and multivariate methods such as Principal Component Analysis (PCA) and Partial Least Squares Data Analysis (PLS-DA).

In preferred embodiments, the fold change of expression of proteins between disease state and control is at least 1.2, 1.4, 1.5, 1.7, 2, 2.5 or 3.

For example, the following criteria may be applied. (a) The position of the peak of interest within the loadings plot indicates an obvious contribution to the separation of the groups in the data modelling process and this also survives a cross validation exercise. (b) A p value of <0.05 is achieved using a Mann-Whitney univariate test. (c) The magnitude of change in abundance of the marker between two groups is at least 1.5 fold either up or down regulated Where mass spectrometry analysis reveals a multiplicity of peptide fragments are present in a given SLDI peak or 2D gel spot, peptide fragment prediction software such as BioLynx (Micromass, UK) may be used to predict the likelihood of fragments of the protein under investigation being generated that match the masses of the SELDI peaks or 2D gel spots. The predicted fragments may then be compared with those identified by mass spectrometry.

In further preferred embodiments of the invention, the method may further comprise the step of isolating a differentially expressed protein identified in the method and/or characterising the isolated protein.

The differentially expressed protein may be isolated by, as appropriate, extraction from 2D gel spot; or by elution from SELDI chips followed by separating the eluted proteins by gel electrophoresis and extracting from the gel a protein band migrating at a molecular weight corresponding to that of the SELDI peak of interest, and identifying the protein or proteins in said extract.

Examples of proteins identified according to the present invention and applicable for use in all of the aspects of the invention disclosed herein include those given in FIGS. 3-6 and FIG. 9 and Table 7, in particular guanosine diphosphate dissociation inhibitor 1, dihydropyrimidinease related protein-2, proteasome subunit alpha type 6, apolipoprotein E, synapsin II, ubiquitin carboxyl-terminal hydrolase isozyme L1, aspartate aminotransferase, glutathione S-transferase mu 1, tubulin beta-4 chain, WW domain binding protein 2, eukaryotic translation initiation factor 4H, tubulin beta-3, neuronal protein Np25, fructose-bisphosphate aldolase A, fructose-bisphosphate aldolase C, nucleolysin TIA related protein, peptidylprolyl isomerase D, voltage-dependent anion-selective channel protein 1 and acetyl-COA acetyltransferase mitochondrial precursor.

In one embodiment, the protein may be used in an assay for specific binding partners of the protein. The protein may also be used in an assay to screen for agonists or antagonists of the protein. The agents or proteins may be screened using a high throughput screening method.

Agonists or antagonists may be, for example, small molecules, antibodies, antisense nucleic acids or siRNA.

In a further aspect, the present invention provides a method of making a pharmaceutical composition which comprises having identified an agent using the above method, the further step of manufacturing the agent and formulating it with an acceptable carrier to provide the pharmaceutical composition.

In a further aspect, the present invention provides a protein as set out in FIGS. 3 to 6 or Table 7 or corresponding human protein as set out in FIG. 9 for use in a method of medical treatment.

In a further aspect, the present invention provides the use of an agent identified by the above method for the preparation of a medicament for the treatment of Alzheimer's disease.

In a further aspect, the present invention provides a method of treating Alzheimer's disease in a patient, the method comprising administering a therapeutically or prophylactically effective amount of such an agent identified by the above method to the patient.

In a further aspect, the present invention provides a method of determining the nature or degree of Alzheimer's disease in a human or animal subject, the method comprising:
(a) establishing a paradigm in which at least one protein is differentially expressed in relevant tissue from, or representative of, subjects having Alzheimer's disease and normal subjects;
(b) obtaining a sample of the tissue from the subjects;
(c) determining the presence, absence or degree of expression of the differentially expressed protein or proteins in the samples; and (d) relating the determination to occurrence of Alzheimer's disease by reference to a previous correlation between such a determination and clinical information.

Where the presence, absence amount or degree of expression of a protein is determined in samples from a patient or subject, the amount of said proteins in the sample is preferably established with reference to a control sample taken from a non-Alzheimer's subject.

The tissue sample may be, for example, blood, plasma, cerebro-spinal fluid or serum.

In one embodiment, at least four proteins are differentially expressed in the paradigm, providing a multi-protein fingerprint of the nature or degree of the Alzheimer's disease.

The differentially expressed protein(s) may be detected using an antibody specific to that protein, for example in an ELISA assay or Western blotting. Alternatively, the differentially expressed protein may be detected by, amongst others, 2D gel electrophoresis or mass spectrometry techniques including LC/MS/MS, MALDI-TOF or SELDI-TOF. The sample may be immobilised on a solid support for analysis.

In another embodiment, the method further comprises determining an effective therapy for treating the Alzheimer's disease.

In a further aspect, the present invention provides a method of treatment by the use of an agent that will restore the expression of one or more differentially expressed proteins in the Alzheimer's disease state to that found in the normal state in order to prevent the development of Alzheimer's disease in a subject.

In a further aspect, the present invention provides a method whereby the pattern of differentially expressed proteins in a tissue sample or body fluid sample or urine of an individual with Alzheimer's disease is used to predict the most appropriate and effective therapy to alleviate the Alzheimer's disease and to monitor the success of that treatment.

In a further aspect, the present invention provides a protein which is differentially expressed in relevant tissue from, or representative of subjects having Alzheimer's disease and normal subjects and which is as obtainable by the method of two-dimensional gel electrophoresis carried out on said tissue or a protein-containing extract thereof, the method comprising:

(a) providing non-linear immobilized pH gradient (IPG) strips of acrylamide polymer 3 mm×180 mm;
(b) rehydrating the IPG strips in a cassette containing 25 ml. of an aqueous solution of urea (8M), 3-[(cholamidopropyl)dimethylammonio]-1-propanesulphonate (CHAPS, 2% w/v), dithioerythritol (DTE, 10 mM), mixture of acids and bases of pH 3.5 to 10 (2% w/v) and a trace of Bromophenol Blue;
(c) emptying the cassette of liquid, transferring the strips to an electrophoretic tray fitted with humid electrode wicks, electrodes and sample cups, covering the strips and cups with low viscosity paraffin oil;
(d) applying 200 micrograms of an aqueous solution of dried, powdered material of the relevant body tissue in urea (8M), CHAPS (4% w/v), Tris (40 mM), DTE (65 mM), SDS (0.05% w/v) and a trace of Bromophenol Blue to the sample cups, at the cathodic end of the IPG strips;
(e) carrying out isoelectric focusing on the gel at a voltage which increases linearly from 300 to 3500 V during 3 hours, followed by another 3 hours at 3500 V, and thereafter at 5000V for a time effective to enable the proteins to migrate in the strips to their pI-dependent final positions;
(f) equilibrating the strips within the tray with 100 ml of an aqueous solution containing Tris-HCl (50 mM) pH 6.8, urea (6M), glycerol (30% v/v), SDS (2% w/v) and DTE (2% w/v) for 12 minutes;
(g) replacing this solution by 100 ml. of an aqueous solution containing Tris-HCl (50 mM) pH 6.8, urea (6M), glycerol (30% v/v), SDS (2% w/v), iodoacetamide (2.5% w/v) and a trace of Bromophenol Blue for 5 minutes;
(h) providing a vertical gradient slab gel 160×200×1.5 mm of acrylamide/piperazine-diacrylyl cross-linker (9-16% T/2.6% C), polymerised in the presence of TEMED (0.5% w/v), ammonium persulphate (0.1% w/v) and sodium thiosulphate (5 mM), in Tris-HCl (0.375M) pH 8.8 as leading buffer;
(i) over-layering the gel with sec-butanol for about 2 hours, removing the overlay and replacing it with water;
(j) cutting the IPG gel strips to a size suitable for the second dimensional electrophoresis, removing 6 mm from the anode end and 14 mm from the cathode end;
(k) over-layering the slab gel with an aqueous solution of agarose (0.5% w/v) and Tris-glycine-SDS (25 mM-198 mM-0.1% w/v) as leading buffer, heated to 70° C. and loading the IPG gel strips onto the slab gel through this over-layered solution;
(l) running the second dimensional electrophoresis at a constant current of 40 mA at 8-12° C. for 5 hours; and
(m) washing the gel.

In another aspect, the invention provides a method of identifying a protein whose level of expression differs between patients with Alzheimer's disease and patients without Alzheimer's disease, comprising:

a) selecting at least one candidate protein from the proteins shown in FIGS. 3-6, Table 7 and FIG. 9,
b) selecting a pH range at which said candidate protein is resolvable from other proteins through 2-dimensional gel electrophoresis using a narrow range immobilised pH gradient (IPG),
c) separating said candidate protein from other proteins in a biological sample by 2-dimensional gel electrophoresis using IPG at said selected pH range, wherein said samples are obtained from an amyloid precursor protein (APP) and presenilin-1 (PS-1) double transgenic mouse and a wild-type mouse, respectively,
d) comparing the intensity of spots in the resulting gels from the transgenic mouse and the wild-type mouse,
e) selecting a spot whose intensity differs between the two gels, and
f) identifying the protein in said spot.

In another aspect, the invention provides a method of identifying a protein whose level of expression differs between patients with Alzheimer's disease and patients without Alzheimer's disease, comprising:

a) separating proteins in a biological sample by gel electrophoresis;
b) extracting from the gel a protein band migrating at a molecular weight corresponding to that of a peak shown in Table 3, 4 or 5;
c) identifying the protein or proteins in said extract.

In a preferred embodiment, identification of the protein in the extract is carried out by mass spectrometry.

Where an extract contains multiple protein fragments, further analysis of the peaks shown in Table 3, 4 or 5 may be carried out using software which predicts peptide fragment generation, such as BioLynx (Micromass, UK). The predicted peptide fragments may then be matched with the peptides identified by MS.

Verification of the identity of the differentially expressed protein may be carried out by Western blotting of cell samples and probing with antibodies specific for peptide epitopes found on the peptides identified by mass spectrometry.

In one embodiment, the differential expression of a protein listed is detected by probing with antibodies specific for the peptides shown in FIG. 10.

In some embodiments, a sample from a single transgenic APP mouse and/or a single transgenic PS-1 mouse is also used. The biological sample may be, for example, brain tissue such as hippocampal tissue, or serum. Step (f) may comprise using mass spectrometry to analyse said protein and searching a database to identify said protein.

Embodiments of the present invention will now be described by way of example and not limitation with reference to the accompanying figures.

BRIEF DESCRIPTION OF THE FIGURES

FIGS. 4A and 4B give details of the proteins identified in 28 spots identified in the hippocampus pH 4-7. Provided amino acid sequences are SEQ ID NOs: 3-59, from top to bottom.

FIGS. 5A and 5B give details of the proteins identified in 7 spots identified in the hippocampus pH 6-9. Provided amino acid sequences are SEQ ID NOs: 60-103, from top to bottom.

FIG. 6 gives details of the proteins identified in 5 spots identified in the in the ROH pH 4-7. Provided amino acid sequences are SEQ ID NOs: 104-109, from top to bottom.

FIG. 7 shows the 19 spots with statistically significant expression changes in more than one comparison. Arrows indicate 'direction' of expression with respect to fold-change against ww. Fold-changes are not generally ≥2-fold INC or DEC but are typically between 1.2 and 1.7

FIGS. 8A and 8B show key protein identifications and general functions.

FIGS. 9A-9J give the accession numbers, where available, for the human proteins corresponding to the mouse/rat proteins listed in FIGS. 3-6.

FIG. 10 shows the results of BioLynx analysis of six SELDI peaks of interest:

FIG. 10a: Proteins identified in 1-D gel bands corresponding to SELDI m/z Peak 1=3771

FIG. 10b: Proteins identified in 1-D gel bands corresponding to SELDI m/z Peak 2=3900

FIG. 10c: Proteins identified in 1-D gel bands corresponding to SELDI m/z Peak 3=4013

FIG. 10d: Proteins identified in 1-D gel bands corresponding to SELDI m/z Peak 4=8619.

FIGS. 10e-A and 10e-B: Proteins identified in 1-D gel bands corresponding to SELDI m/z Peak 5=8834.

FIGS. 10f-A and 10f-B: Proteins identified in 1-D gel bands corresponding to SELDI m/z Peak 6=9172.

FIGS. 10-g-A and 10-B: Proteins identified in 1-D gel bands corresponding to Peak 1=3770 and Peak 4=8618.

FIGS. 11a-A, 11a-B, 11b-A and 11b-B illustrate the rationale of analyzing observed peptide fragments using BioLynx, showing predicted and observed peptide fragments for mouse major urinary protein 1 relating to SELDI peaks P1 and P2 (11a-A and 11a-B) and peak P4 (11b-A and 11b-B). Shown underneath the spectral and gel images is the amino acid sequence of major urinary protein 1 (precursor, i.e., full-length; SEQ ID NO: 110). The peptide on which the identification was derived by Mascot is underlined. Highlighted is the peptide predicted by BioLynx that matches the m/z of the SELDI peak and also includes the Mascot (experimentally observed) peptide. The text indicates the equivalent Swiss-Prot amino acid residue numbers of the BioLynz predicted peptide. Also, the signal sequence of the protein (the first 19 amino acids) is indicated by black lines which is typically removed to create the mature protein.

DETAILED DESCRIPTION

Definitions

Figure 1:
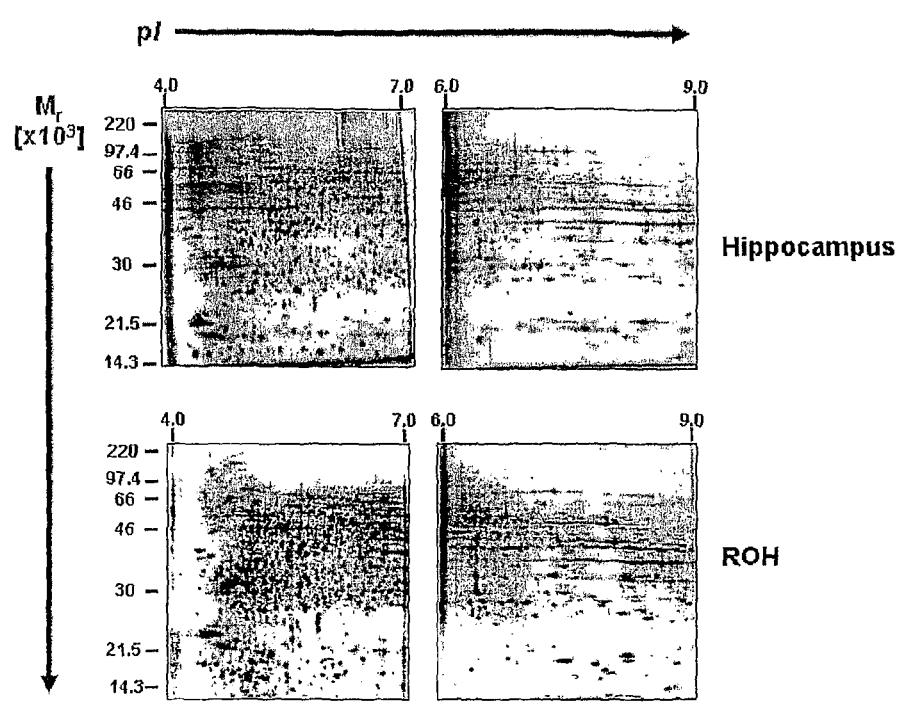
FIG. 1 shows a typical protein expression profile obtained using pH 4-7L and pH 6-9L from both the hippocampus and rest of hemisphere tissue.

"Differential expression", as used herein, refers to at least one recognisable difference in tissue protein expression. It may be a quantitatively measurable, semi-quantitatively estimatable or qualitatively detectable difference in tissue protein expression. Thus, a differentially expressed protein (herein DEP) may be strongly expressed in tissue in the normal state and less strongly expressed or not expressed at all in tissue in the Alzheimer's disease state. Conversely, it may be strongly expressed in tissue in the disorder state and less strongly expressed or not expressed at all in the normal state. Similarly, the differential expression can be either way around in the comparison between untreated and treated tissue. Further, expression may be regarded as differential if the protein undergoes any recognisable change between the two states under comparison.

The term "paradigm" means a prototype example, test model or standard.

Wherever a differentially expressible protein is used in the screening procedure, it follows that there must have been at some time in the past a preliminary step of establishing a paradigm by which the differential expressibility of the protein was pre-determined. Once the paradigm has been established, it need not be re-established on every occasion that a screening procedure is carried out. The term "establishing a paradigm" is to be construed accordingly.

"Relevant tissue" means any tissue which undergoes a biological change in response Alzheimer's disease.

"Tissue . . . representative of . . . subjects" means any tissue in which the above-mentioned biological change can be simulated for laboratory purposes and includes, for example, a primary cell culture or cell line derived ultimately from relevant tissue.

The term "subjects" includes human and animal subjects. The treatments referred to above can comprise the administration of one or more drugs or foodstuffs, and/or other factors such as diet or exercise.

The term "corresponding human protein" to a mouse or rat protein indicates the human protein having the same name as the mouse or rat protein in question. In most cases this will be the human protein with the highest amino acid sequence identity as the mouse or rat protein in question.

The differentially expressed proteins (DEPs) include "fingerprint proteins", "target proteins" or "pathway proteins".

The term "fingerprint protein", as used herein, means a DEP, the expression of which can be used, alone or together with other DEPs, to monitor or assess the condition of a patient suspected of suffering from Alzheimer's disease. Since these proteins will normally be used in combination, especially a combination of four or more, they are conveniently termed "fingerprint proteins", without prejudice to the possibility that on occasions they may be used singly or along with only one or two other proteins for this purpose. Such a fingerprint protein or proteins can be used, for example, to diagnose a particular type of Alzheimer's disease and thence to suggest a specific treatment for it.

The term "diagnosis", as used herein, includes the provision of any information concerning the existence, non-existence or probability of the disorder in a patient. It further includes the provision of information concerning the type or classification of the disorder or of symptoms which are or may be experienced in connection with it. It encompasses prognosis of the medical course of the disorder.

The term "target protein", as used herein, means a DEP, the level or activity of which can be modulated by treatment to alleviate Alzheimer's disease. Modulation of the level or activity of the target protein in a patient may be achieved, for example, by administering the target protein, another protein or gene which interacts with it or an agent which counteracts or reduces it, for example an antibody to the protein, competitive inhibitor of the protein or an agent which acts in the process of transcription or translation of the corresponding gene.

The term "alleviate", as used herein, in relation to Alzheimer's disease means any form of reducing one or more undesired symptoms or effects thereof. Any amelioration of the Alzheimer's disease of the patient falls within the term "alleviation".

Alternatively or additionally, the DEPs can interact with at least one other protein or with a gene involved in Alzheimer's disease. Such other proteins are termed herein "pathway proteins" (PPs). The term is applied to the protein with which the DEP interacts, not to the DEP itself, although a pathway protein can be another DEP.

Methods and Compositions for the Treatment of Alzheimer's Disease.

Proteins termed "target proteins" and/or fingerprint proteins are described which are differentially expressed in Alzheimer's disease states relative to their expression in normal states and/or which are differentially expressed in response to manipulations relevant to Alzheimer's disease. Additionally, proteins termed "pathway proteins" are described which interact with proteins involved in brain function. Methods for the identification of such fingerprint target and pathway proteins are also described.

Described below are methods for the identification of compounds, which modulate the expression of proteins, involved in Alzheimer's disease. Additionally described below are methods for the treatment of Alzheimer's disease.

Also discussed below are methods for prognostic and diagnostic evaluation of Alzheimer's disease and for the identification of subjects exhibiting a predisposition to this disorders.

1. Identification of Differentially Expressed and Pathway Proteins

In one embodiment, the present invention concerns methods for the identification of proteins which are involved in Alzheimer's disease. Such proteins may represent proteins, which are differentially expressed in Alzheimer's disease relative to their expression in normal states. Further, such proteins may represent proteins that are differentially expressed or regulated in response to manipulation relevant to treating Alzheimer's disease. Such differentially expressed proteins may represent "target" or "fingerprint" proteins. Methods for the identification of such proteins are described in Section 1.1. Methods for the further characterisation of such differentially expressed proteins and for their identification as target and/or fingerprint proteins are presented below in Section 1.3.

In addition, methods are described herein in Section 1.3, for the identification of proteins termed pathway proteins involved in Alzheimer's disease. Pathway proteins, as used herein, refer to a protein, which exhibits the ability to interact with other proteins relevant to Alzheimer's disease. A pathway protein may be differentially expressed and therefore may have the characteristics of a target or fingerprint protein.

"Differential expression", as used herein, refers to both qualitative as well as quantitative differences in protein expression. Thus a differentially expressed protein may qualitatively have its expression activated or completely inactivated in normal versus an Alzheimer's disease state or under control versus experimental conditions. Such a qualitatively regulated protein will exhibit an expression pattern within a given tissue or cell type, which is detectable in either control or Alzheimer's disease subject, but not detectable in both. Alternatively, such a qualitatively regulated protein will exhibit an expression pattern within one or more cell types, which is detectable in either control or experimental subjects but not detectable in both. "Detectable", as used herein, refers to a protein expression pattern, which are detectable using techniques such as differential display 2D electrophoresis.

Alternatively, a differentially expressed protein may have its expression modulated, i.e. quantitatively increased or decreased, in normal versus Alzheimer's disease or under control versus experimental conditions. The degree to which expression differs in normal versus Alzheimer's disease states or control versus experimental states need only be large enough to be visualised via standard characterisation techniques, such as silver staining of 2D-electrophoretic gels. Other such standard characterisation techniques by which expression differences may be visualised are well known to those skilled in the art. These include successive chromatographic separations of fractions and comparisons of the peaks, capillary electrophoresis and separations using microchannel networks, including on a micro-chip.

Chromatographic separations can be carried out by high performance liquid chromatography as described in Pharmacia literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on a applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electroosmotic flow (EOF) of the sample, the positive ions move fastest, followed by uncharged material and negatively charged ions. Thus, proteins are separated essentially according to charge on them.

Micro-channel networks function somewhat like capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form microchannels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20: pages 727-731.

Surface enhanced laser desorption ionisation time of flight mass spectrometry (SELDI-TOF-MS) combined with ProteinChip technology can also provide a rapid and sensitive means of profiling proteins and is used as an alternative to 2D gel electrophoresis in a complementary fashion. The ProteinChip system consists of aluminium chips to which protein samples can be selectively bound on the surface chemistry of the chip (eg. anionic, cationic, hydrophobic, hydrophilic etc). Bound proteins are then co-crystallised with a molar excess of small energy-absorbing molecules. The chip is then analysed by short intense pulses of N2 320 nm UV laser with protein separation and detection being by time of flight mass spectrometry. Spectral profiles of each group within an experiment are compared and any peaks of interest can be further analysed using techniques as described below to establish the identity of the protein.

Differentially expressed proteins may be further described as target proteins and/or fingerprint proteins. "Fingerprint proteins", as used herein, refer to a differentially expressed protein whose expression pattern may be utilised as part of a prognostic or diagnostic Alzheimer's disease or which, alternatively, may be used in methods for identifying compounds useful for the treatment of Alzheimer's disease. A fingerprint protein may also have characteristics of a target protein or a pathway protein.

"Target protein", as used herein, refers to a differentially expressed protein involved in Alzheimer's disease such that modulation of the level or activity of the protein may act to prevent the development of Alzheimer's disease. A target protein may also have the characteristics of a fingerprint protein or a pathway protein.

1.1 Method for the Identification of Differentially Expressed Proteins

A variety of methods may be used for the identification of proteins, which are involved in Alzheimer's disease. Described in Section 1.1.1 are several experimental paradigms, which may be utilised for the generation of subjects, and samples, which may be used for the identification of such proteins. Material from the paradigm control and experimental subjects may be characterised for the presence of differentially expressed protein sequences as discussed below in Section 1.1.2.

1.1.1 Paradigms for the Identification of Differentially Expressed Proteins Among the paradigms that may be utilised for the identification of differentially expressed proteins involved in Alzheimer's disease are paradigms designed to analyse those proteins that are differentially expressed between normal and Alzheimer's disease states.

In one embodiment of such a paradigm, brain tissue from normal and Alzheimer's disease model subjects would be compared. Appropriate tissues would include, but not be limited to, hippocampal tissue.

A further paradigm, which may be utilised for the identification of differentially expressed proteins involved in Alzheimer's disease is a paradigms designed to analyse those proteins which may be involved in genetic models of Alzheimer's disease. Accordingly, such paradigms are referred to as "genetic Alzheimer's disease paradigms".

In one embodiment of such a paradigm, test subjects may include transgenic or mutant rats or mice and brain tissue samples. The examples provided below demonstrate the use of such genetic paradigms in identifying proteins which are differentially expressed in Alzheimer's disease model animals versus normal animals.

1.1.2 Analysis of Paradigm Material

In order to identify differentially expressed proteins, brain tissues from subjects utilised in paradigms such as those described above in 1.1.1 are obtained. In addition, blood and body fluids may be analysed since the differentially expressed proteins in brain tissue might be released into the circulations.

1.2 Methods for the Identification of Pathway Proteins

Methods are described herein for the identification of pathway proteins. "Pathway protein", as used herein, refers to a protein which exhibits the ability to interact with differentially expressed proteins involved in Alzheimer's disease. A pathway protein may be differentially expressed and, therefore, may have the characteristics of a target and/or fingerprint protein.

Any method suitable for detecting protein-protein interactions may be employed for identifying pathway proteins by identifying interactions between candidate proteins and proteins known to be differentially expressed in Alzheimer's disease states. Such differentially expressed proteins may be cellular or extracellular proteins. Those proteins, which interact with such differentially expressed proteins, represent pathway gene products.

Among the traditional methods, which may be employed, are co-immunoprecipitation, crosslinking and co-purification through gradients or chromatographic columns.

Alternatively, the differentially expressed protein may be immobilised on a solid support and incubated with a cell extract to pull down interacting proteins. The protein which is immobilized on a solid support may be immobilized using an antibody against that protein bound to a solid support or via other technologies which are known. A preferred method uses a fusion protein including glutathione-S-transferase (GST). This may be immobilised on glutathione agarose beads. Following incubation of the immobilised protein with the cell extract, the beads and bound protein may be separated from the cell extract by centrifugation and subjected to further analysis, for example SDS-PAGE.

Utilising procedures such as these allows for the identification of pathway proteins. Once identified, a pathway protein may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g. Creighton (1983) "Proteins: Structures and Molecular Principles", W.H. Freeman & Co., N.Y., pp. 34-49). The amino acid sequence obtained may be used as a guide for the generation of oligonucleotide mixtures that can be used to screen for pathway gene sequences. Screening may be accomplished, for example, by standard hybridisation or PCR techniques. Techniques for the generation of oligonucleotide mixtures and the screening are well-known (see, e.g. Ausubel, supra. and PCR Protocols: A Guide to Methods and Applications (1990) Innis, M. et al., eds. Academic Press Inc., New York).

One method, which detects protein interactions in vivo, the yeast two-hybrid system, is described in detail for illustration only and not by way of limitation. One version of this system has been described (Chien et al (1991) Proc. Natl. Acad. Sci. USA, 88, 9578-9582) and is commercially available from Clontech (Palo Alto, Calif.)

The two-hybrid system or related methodology may be used to screen activation domain libraries for proteins that interact with a known differentially expressed >bait=protein.

Total genomic or cDNA sequences are translationally fused to the DNA encoding an activation domain, e.g. an activated domain of GAL-4. This library and a plasmid encoding a hybrid of the bait protein product fused to the DNA-binding domain are co-transformed into a yeast reporter strain, and the resulting transformants are screened for those that express the reporter gene. By way of example rather than limitation, the bait gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait proteins are to be detected can be made using methods routinely practised in the art.

Protein interactions can also be monitored and analysed using the Biacore™ system for monitoring biomolecular binding. Biacore™ technology enables direct detection and monitoring of biomolecular binding events for rapid assessment of method development and purification of these biomolecules. A target biomolecule, such as a differentially expressed protein, is attached to the surface of a sensor and aliquots of the sample passed over this surface. When a further protein binds to the primary protein on the sensor surface (a hit) there is a change is mass concentration close to the surface. This change in concentration is detected in real time, providing the opportunity to monitor the binding of native protein from complex mixtures to a target protein without prior introduction of labels or tags. The bound protein is then removed from the surface of the sensor chip, and purified by conventional methods (Nordhoff et al, 1999). Biacore™ technology can provide information about the kinetics, affinity and specificity of protein interactions. Thus the Biacore™ technology can allow the detection of pathway proteins.

Once a pathway protein has been identified and isolated, it may be further characterised as, for example, discussed below, in Section 1.3.

1.3 Characterisation of Differentially Expressed and Pathway Proteins

Differentially expressed proteins, such as those identified via the methods discussed above in Section 1.1, and pathway genes, such as those identified via the methods discussed above in Section 1.2, as well as genes identified by alternative means, may be further characterised by utilising, for example, methods such as those discussed herein. Such proteins will be referred to herein as "identified proteins".

Analyses such as those described herein, yield information regarding the biological function of the identified proteins. An assessment of the biological function of the differentially expressed proteins, in addition, will allow for their designation as target and/or fingerprint proteins.

Specifically, any of the differentially expressed proteins whose further characterisation indicates that a modulation of the proteins expressed or a modulation of the proteins activity may ameliorate Alzheimer's disease will be designated "target proteins", as defined above, in Section 1. Such target proteins, along with those discussed below, will constitute the focus of the compound discovery strategies discussed below in Section 3. Further, such target proteins and/or modulating compounds can be used as part of the treatment and/or prevention of Alzheimer's disease.

Any of the differentially expressed proteins whose further characterisation indicates that such modulations may not positively affect Alzheimer's disease, but whose expression pattern contributes to a protein "fingerprint" pattern correlative of, for example, Alzheimer's disease, will be designated a "fingerprint protein". "Fingerprint patterns" will be more fully discussed below, in Section 7.1. It should be noted that each of the target proteins may also function as fingerprint proteins, as well as may all or a portion of the pathway proteins.

It should further be noted that the pathway proteins may also be characterised according to techniques such as those described herein. Those pathway proteins which yield information indicating that they are differentially expressed and that modulation of the proteins expression or a modulation of the proteins expression or a modulation of the proteins activity may ameliorate any of Alzheimer's disease will also be designated "target proteins". Such target proteins, along with those discussed above, will constitute the focus of the compound discovery strategies discussed below, in Section 3 and can be used as part of the treatment methods described in Section 4 below.

It should be additionally noted that the characterisation of one or more of the pathway proteins may reveal a lack of differential expression, but evidence that modulation of the gene=s activity or expression may, nonetheless, ameliorate Alzheimer's disease symptoms. In such cases, these genes and gene products would also be considered a focus of the compound discovery strategies of Section 3 below.

In instances wherein a pathway protein's characterisation indicates that modulation of gene expression or gene product activity may not positively affect Alzheimer's disease, but whose expression is differentially expressed and contributes to a gene expression fingerprint pattern correlative of, for example, Alzheimer's disease, such pathway genes may additionally be designated as fingerprint genes.

A variety of techniques can be utilised to further characterise the identified proteins. First, the corresponding nucleotide sequence of the identified protein may be obtained by utilising standard techniques well known to those of skill in the art, may, for example, be used to reveal homologies to one or more known sequence motifs which may yield information regarding the biological function of the identified protein.

Secondly, the biological function of the identified proteins may be more directly assessed by utilising relevant in vivo and in vitro systems. In vivo systems may include, but are not limited to, animal systems which naturally exhibit Alzheimer's disease-like symptoms, or ones which have been engineered to exhibit such symptoms. Further, such systems may include systems for the further characterisation of Alzheimer's disease, and may include, but are not limited to, naturally occurring and transgenic animal systems such as those described above, in Section 1.1.1, and Section 2.2.1 below. In vitro systems may include, but are not limited to, cell-based systems comprising cell types known to produce and secrete insulin. Such cells may be wild type cells, or may be non-wild type cells containing modifications known to, or suspected of, contributing to Alzheimer's disease. Such systems are discussed in detail below, in Section 2.2.2.

In further characterising the biological function of the identified proteins, the expression of these proteins may be modulated within the in vivo and/or in vitro systems, i.e. either overexpressed or underexpressed in, for example, transgenic animals and/or cell lines, and its subsequent effect on the system then assayed. Alternatively, the activity of the identified protein may be modulated by either increasing or decreasing the level of activity in the in vivo and/or in vitro system of interest, and its subsequent effect then assayed.

The information obtained through such characterisations may suggest relevant methods for the treatment of Alzheimer's disease involving the protein of interest. Further, relevant methods for the control of Alzheimer's disease involving the protein of interest may be suggested by information obtained from such characterisations. For example, treatment may include a modulation of protein expression and/or protein activity. Characterisation procedures such as those described herein may indicate where such modulation should involve an increase or a decrease in the expression or activity of the protein of interest. Such methods of treatment are discussed below in Section 4.

2. Differentially Expressed and Pathway Proteins

Identified proteins, which include, but are not limited to, differentially expressed proteins such as those identified in Section 1.1 above, and pathway proteins, such as those identified in Section 1.2 above, are described herein. Specifically, the amino acid sequences of such identified proteins are described. Further, antibodies directed against the identified protein, and cell- and animal-based models by which the identified proteins may be further characterised and utilised are also discussed in this Section.

2.1 Antibodies Specific for Differentially Expressed or Pathway Proteins

The present invention also relates to methods for the production of antibodies capable of specifically recognising one or more differentially expressed or pathway protein epitopes. Such antibodies may include, but are not limited to, polyclonal antibodies, monoclonal antibodies (mAbs), humanised or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be utilised as part of Alzheimer's disease treatment methods, and/or may be used as part of diagnostic techniques whereby patients may be tested for abnormal levels of fingerprint, target, or pathway gene proteins, or for the presence of abnormal forms of such proteins.

For the production of antibodies to a differentially expressed or pathway protein, various host animals may be immunised by injection with a differentially expressed or pathway protein, or a portion thereof. Such host animals may include, but are not limited to, rabbits, mice and rats, to name but a few. Various adjuvants may be used to increase the immunological response, depending on the host species, including active substances such as lysolecithin, Pluronic polyols, polyanions, peptides, oil emulsions, keyhole limpet hemocyamin, dinitrophenol, and potentially useful human adjuvant such as BCG bacille Calmette-Fuerin) and *Corynebacterium parvum*.

Polyclonal antibodies are heterogeneous populations of antibody molecules derived from the sera of animals immunised with an antigen, such as target proteins, or an antigenic functional derivative thereof. For the production of polyclonal antibodies, host animals such as those described above, may be immunised by injection with differentially expressed or pathway protein supplemented with adjuvants as also described above.

Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975, Nature 256; 495-497; and U.S. Pat. No. 4,376,110), the human β-cell hybridoma technique (Kosbor, et al., 1983, Immunology Today 4: 72; Cole, et al., 1983, Proc. Natl. Acad. Sci. USA 80; 2026-2030), and the EBV-hybridoma technique (Cole, et al., 1985, Monoclonal Antibodies and Cancer Therapy, Alan R. Liss Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of chimeric antibodies (Morrison, et al., 1984, Proc. Natl. Acad. Sci. 81: 6851-6855; Neuberger, et al., 1984, Nature 312: 604-608; Takeda, et al., 1985, Nature 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242: 423-426; Huston, et al., 1988, Proc. Natl. Acad. Sci. USA 85: 5879-5883; and Ward, et al., 1989, Nature 334: 544-546) can be adapted to produce differentially expressed or pathway protein-single chain antibodies. Single chain antibodies are formed by linking the heavy and light chain fragments of the Fv region via an amino acid bridge, resulting in a single chain polypeptide.

Antibody fragments, which recognise specific epitopes, may be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternative, Fab expression libraries may be constructed (Huse, et al., 1989, Science 246: 1275-1281) to allow rapid and easy identification of monoclonal Fab fragments with the desired specificity.

2.2 Cell- and Animal-Based Model Systems

Described herein are cell- and animal-based systems, which act as models for Alzheimer's disease. These systems may be used in a variety of applications. For example, the animal-based model systems can be utilised to identify differentially expressed proteins via one of the paradigms described above, in Section 1.1.1. Cell- and animal-based model systems may be used to further characterise differentially expressed and pathway proteins, as described above in Section 1.3. Such further characterisation may, for example, indicate that a differentially expressed protein is a target protein. Second, such assays may be utilised as part of screening strategies designed to identify compounds which are capable of ameliorating Alzheimer's disease symptoms, as described below. Thus, the animal- and cell-based models may be used to identify drugs, pharmaceuticals, therapies and interventions which may be effective in treating Alzheimer's disease. In addition, as described in detail below, in Section 6, such animal models may be used to determine the LD$_{50}$ and the ED$_{50}$ in animal subjects, and such data can be used to determine the in vivo efficacy of potential Alzheimer's disease treatments.

2.2.1 Animal-Based Systems

Animal-based model systems of Alzheimer's disease may include, but are not limited to, non-recombinant and engineered transgenic animals.

Additionally, animal models exhibiting Alzheimer's disease may be engineered by utilising, for example, the gene sequences of target proteins such as those described above in Section 2, in conjunction with techniques for producing transgenic animals that are well known to those of skill in the art. For example, gene sequences of target proteins may be introduced into, and overexpressed in, the genome of the animal of interest, or, if endogenous gene sequences of target proteins are present, they may either be overexpressed or, alternatively, may be disrupted in order to underexpress or inactivate gene expression of target proteins.

In order to overexpress the target gene sequence of a target protein, the coding portion of the target gene sequence may be ligated to a regulatory sequence, which is capable of driving gene expression in the animal and cell type of interest. Such regulatory regions will be well known to those of skill in the art.

For underexpression of an endogenous gene sequence of a target protein, such a sequence may be isolated and engineered such that when reintroduced into the genome of the animal of interest, the endogenous gene alleles of the target protein will be inactivated. Preferably, the engineered gene sequence of the target protein is introduced via gene targeting such that the endogenous sequence is disrupted upon integration of the engineered target gene sequence into the animal=s genome.

Animals of any species, including, but not limited to, mice, rats, rabbits, guinea pigs, pigs, mini-pigs, goats and non-human primates, e.g. baboons, squirrels, monkeys and chimpanzees may be used to generate Alzheimer's disease animal models.

Any technique known in the art may be used to introduce a target gene transgene of a target protein into animals to produce the founder lines of transgenic animals. Such techniques include, but are not limited to, pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82: 6148-6152); gene targeting in embryonic stem cells (Thompson et al., 1989, Cell 56: 313-321); electroporation of embryos (Lo, 1983, Mol. Cell. Biol. 3: 1803-1814); and sperm-mediated gene transfer (Lavitrano et al., 1989, Cell 57: 717-723); etc. For a review of such techniques, see Gordon, 1989, Transgenic Animals, Intl. Rev. Cytol. 115: 171-229.

The present invention provides for transgenic animals that carry the transgene in all their cells, as well as animals which carry the transgene in some, but not all their cells, i.e. mosaic animals (see, for example, techniques described by Jakobovits, 1994, Curr. Biol. 4: 761-763). The transgene may be integrated as a single transgene or in concatamers, e.g. head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232-6236). The regulatory sequences required to such a cell-type specific activation will depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilised, vectors containing some nucleotide sequences homologous to the gene of the endogenous target protein of interest are designed for the purpose of integrating, via homologous recombination with chromosomal sequences, into and disrupting the function of, the nucleotide sequence of the endogenous target gene. The transgene may also be selectively introduced into a particular cell type, thus inactivating the endogenous gene of interest in only that cell type, by following, for example, the teaching of Gu et al. (Gu, H. et al., 1994, Science 265: 103-106). The regulatory sequences required for such a cell-type specific inactivation will depend upon the particular cell type of interest, and will be apparent to those of skill in the art.

Once transgenic animals have been generated, the expression of the recombinant target gene and protein may be assayed utilising standard techniques. Initial screening may be accomplished by Southern blot analysis or PCR techniques to analyse animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridisation analysis, and RT-PCR. Samples of target protein-expressing tissue may also be evaluated immunocytochemically using antibodies specific for the transgene protein of interest.

The target protein transgenic animals that express target gene mRNA or target protein transgene peptide (detected immunocytochemically, using antibodies directed against target protein epitopes) at easily detectable levels should then be further evaluated to identify those animals which display characteristic Alzheimer's disease-like symptoms. Additionally, specific cell types within the transgenic animals may be analysed and assayed for cellular phenotypes characteristic of Alzheimer's disease. Further, such cellular phenotypes may include an assessment of a particular cell types fingerprint pattern of expression and its comparison to known fingerprint expression profiles of the particular cell type in animals exhibiting Alzheimer's disease. Such transgenic animals serve as suitable model systems for Alzheimer's disease.

Once target protein transgenic founder animals are produced (i.e. those animals which express target proteins in cells or tissues of interest and which, preferably, exhibit symptoms of Alzheimer's disease), they may be bred, inbred, outbred or crossbred to produce colonies of the particular animal. Examples of such breeding strategies include, but are not limited to, outbreeding of founder animals with more than one integration site in order to establish separate lines; inbreeding of separate lines in order to produce compound target protein transgenics that transgenically express the target protein of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target protein and the development of Alzheimer's disease-like symptoms. One such approach is to cross the target protein transgenic founder animals with a wild type strain to produce an F1 generation that exhibits Alzheimer's disease-like symptoms. The F1 generation may then be inbred in order to develop a homozygous line, if it is found that homozygous target protein transgenic animals are viable.

Preferred transgenic animal models of Alzheimer's disease include mice over-expressing mutant alleles of APP or PS1 and double (APP/PS1) transgenic mouse models over-expressing mutant alleles of both APP and PS1. Mutation in the amyloid precursor protein (APP) gene, or failure to clear the Aβ peptide fragments, results in toxic elevations of this peptide which are deposited throughout the brain as insoluble fibrillar aggregates [4] known as plaques, which are particularly concentrated in the hippocampus. Mutations in presenilin (PS) 1, and PS2 gene, also alter the level of the Aβ peptide, consequently further supporting this peptide's critical role in the development of AD. The mutant APP(K670N, M671L) transgenic line, Tg2576, shows markedly elevated amyloid beta-protein (A beta) levels at an early age and, by 9-12 months, develops extracellular AD-type A beta deposits in the cortex and hippocampus. Mutant PS1 transgenic mice do not show abnormal pathology, but do display subtly elevated levels of the highly amyloidogenic 42- or 43-amino acid peptide A beta42(43). In the doubly transgenic progeny from a cross between line Tg2576 and a mutant PS1M146L transgenic line, the development of AD-like pathology is substantially enhanced (Holcomb et al., Nat. Med. 1998 January; 4 (1):97-100).

2.2.2 Cell-Based Assays

Cells that contain and express target gene sequences which encode target proteins and, further, exhibit cellular phenotypes associated with Alzheimer's disease, may be utilised to identify compounds that exhibit an ability to ameliorate Alzheimer's disease symptoms.

Further, the fingerprint pattern of protein expression of cells of interest may be analysed and compared to the normal fingerprint pattern. Those compounds which cause cells exhibiting Alzheimer's disease produce a fingerprint pattern more closely resembling a normal fingerprint pattern for the cell of interest may be considered candidates for further testing regarding an ability to ameliorate Alzheimer's disease symptoms.

Further, cell lines which may be used for such assays may also include recombinant, transgenic cell lines. For example, the Alzheimer's disease animal models of the invention discussed above, in Section 2.2.1, may be used to generate cell lines, containing one or more cell types involved in brain function, that can be used as cell culture models for this disorder. While primary cultures derived from the Alzheimer's disease model transgenic animals of the invention may be utilised, the generation of continuous cell lines is preferred. For examples of techniques which may be used to derive a continuous cell line from the transgenic animals, see Small, et al., 1985, Mol. Cell. Biol. 5: 642-648.

Alternatively, cells of a cell type known to be involved Alzheimer's disease may be transfected with sequences capable of increasing or decreasing the amount of target protein within the cell. For example, gene sequences of target proteins may be introduced into, and overexpressed in, the genome of the cell of interest, or, if endogenous gene sequences of the target protein are present, they may either be overexpressed or, alternatively, be disrupted in order to underexpress or inactivate target protein expression.

In order to overexpress a gene sequence of a target protein, the coding portion of the target gene sequence may be ligated to a regulatory sequence, which is capable of driving gene expression in the cell type of interest. Such regulatory regions will be well known to those of skill in the art, and may be utilised in the absence of undue experimentation.

For underexpression of an endogenous target protein the gene sequence may be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell=s genome. Gene targeting is discussed above, in Section 2.2.1.

Transfection of target protein gene sequence nucleic acid may be accomplished by utilising standard techniques. See, for example, Ausubel, 1989, supra. Transfected cells should be evaluated for the presence of the recombinant target gene sequences, for expression and accumulation of target gene mRNA, and for the presence of recombinant target protein production. In instances wherein a decrease in target protein expression is desired, standard techniques may be used to demonstrate whether a decrease in endogenous target gene expression and/or in target protein production is achieved.

3. Screening Assays for Compounds that Interact with the Target Proteins

The following assays are designed to identify compounds that bind to target proteins, bind to other cellular proteins that interact with target proteins, and to compounds that interfere with the interaction of the target proteins with other cellular proteins. Such compounds may include, but are not limited to, other cellular proteins. Methods for the identification of such cellular proteins are described below in Section 3.2.

Compounds may include, but are not limited to, peptides such as, for example, soluble peptides, including, but not limited to, Ig-tailed fusion peptides, comprising extracellular portions of target protein transmembrane receptors, and members of random peptide libraries (see, e.g. Lam, K. S. et al., 1991, Nature 354: 82-84; Houghten, R. et al., 1991, Nature 354: 84-86) made of D- and/or L-configuration amino acids, phosphopeptides (including, but not limited to, member of random or partially degenerate, directed phosphopeptide libraries: se, e.g., Songyang, Z. et al., 1993, Cell 72: 767-778), antibodies (including, but not limited to, polyclonal, monoclonal, humanised, anti-idiotypic, chimeric or single chain antibodies, and FAb, F(ab')$_2$ and FAb expression library fragments, and epitope-binding fragments thereof) and small organic or inorganic molecules.

Compounds identified via assays such as those described herein may be useful, for example, in elaborating the biological function of the target protein, and for ameliorating Alzheimer's disease. In instances, for example, whereby a Alzheimer's disease situation results from a lower overall level of target protein expression and/or target protein activity in a cell or tissue involved in such a Alzheimer's disease, compounds that interact with the target protein may include ones which accentuate or amplify the activity of the bound target protein. Such compounds would bring about an effective increase in the level of target protein activity, thus ameliorating symptoms. In instances whereby mutations within the target gene cause aberrant target proteins to be made which have a deleterious effect that leads to Alzheimer's disease, compounds that bind target protein may be identified that inhibit the activity of the bound target protein. Assays for testing the effectiveness of compounds, identified by, for example, techniques such as those described in Sections 3.1 to 3.3, are discussed below, in Section 3.4.

3.1 In Vitro Screening Assays for Compounds that Bind to the Target Proteins

In vitro systems may be designed to identify compounds capable of binding the target proteins of the invention. Compounds identified may be useful, for example, in modulating the activity of wild type and/or mutant target proteins, may be useful in elaborating the biological function of the target protein, may be utilised in screens for identifying compounds that disrupt normal target protein interactions, or may in themselves disrupt such interactions.

The principle of the assays used to identify compounds that bind to the target protein involves preparing a reaction mixture of the target protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring target protein or the test substance onto a solid phase and detecting target protein/test compounds complexes anchored on the solid phase at the end of the reaction. In one embodiment of such a method, the target protein may be anchored onto a solid surface, and the test compound, which is not anchored, may be labelled, either directly or indirectly.

In practice, microtiter plates may conveniently be utilised as the solid phase. The anchored component may be immobilised by non-covalent or covalent attachments. Non-covalent attachment may be accomplished by simply coating the solid surface with a solution of the protein and drying. Alternatively, an immobilised antibody, preferably a monoclonal antibody, specific for the protein to be immobilised may be used to anchor the protein to the solid surface. The surfaces may be prepared in advance and stored.

In order to conduct the assay, the non-immobilised component is added to the coated surface containing the anchored component. After the reaction is complete, unreacted components are removed (e.g. by washing) under conditions such that any complexes formed will remain immobilised on the solid surface. The detection of complexes anchored on the solid surface can be accomplished in a number of ways. Where the previously non-immobilised component is pre-labelled, the detection of label immobilised on the surface indicates that complexes were formed. Where the previously non-immobilised component is not pre-labelled, an indirect label can be used to detect complexes anchored on the surface, e.g. using a labelled antibody specific for the previously non-immobilised component (the antibody, in turn, may be directly labelled or indirectly labelled with a labelled anti-Ig antibody).

Alternatively, a reaction can be conducted in a liquid phase, the reaction products separated from unreacted components, and complexes detected, e.g. using an immobilised antibody specific for target protein or the test compound to anchor any complexes formed in solution, and a labelled antibody specific for the other component of the possible complex to detect anchored complexes.

3.2 Assays for Cellular Proteins that Interact with the Target Protein

Any method suitable for detecting protein-protein interactions may be employed for identifying novel target protein-cellular or extracellular protein interactions. These methods are outlined in Section 1.2 for the identification of pathway proteins, and may be utilised herein with respect to the identification of proteins which interact with identified target proteins.

3.3 Assays for Compounds that Interfere with Target Protein/Cellular Macromolecule Interaction The target proteins of the invention may, in vivo, interact with one or more cellular or extracellular macromolecules, such as proteins. Such macromolecules may include, but are not limited to, nucleic acid molecules and those proteins identified via methods such as those described above in Section 3.2. For purposes of this discussion, such cellular and extracellular macromolecules are referred to herein as >binding partners=. Compounds that disrupt such interactions may be useful in regulating the activity of the target protein, especially mutant target proteins. Such compounds may include, but are not limited to, molecules such as antibodies, peptides, and the like, as described, for example, in Section 3.1.

The basic principle of the assay systems used to identify compounds that interfere with the interaction between the target protein and its cellular or extracellular binding partner or partners involves preparing a reaction mixture containing the target protein, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of target protein and its cellular or extracellular binding partner. Control reaction mixtures are incubated without the test compound or with a placebo. The formation of any complexes between the target protein and the cellular or extracellular binding partner is then detected. The formation of a complex in the control reaction, but not in the reaction mixture containing the test compound, indicates that the compound interferes with the interaction of the target protein and the interactive binding partner. Additionally, complex formation within reaction mixtures contains the test compound and a mutant target protein. This comparison may be important in those cases wherein it is desirable to identify compounds that disrupt interactions of mutant but not normal target proteins.

The assay for compounds that interfere with the interaction of the target and binding partners can be conducted in a heterogeneous or homogeneous format. Heterogeneous assays involve anchoring either the target protein or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target protein and the binding partners, e.g. by competition, can be identified by conducting the reaction in the presence of the test substance, i.e. by adding the test substance to the reaction mixture prior to or simultaneously with the target protein and interactive cellular or extracellular binding partner. Alternatively, test compounds that disrupt pre-formed complexes, e.g. compounds with higher binding constants that displace one of the components from the complex, can be tested by adding the test compound to the reaction mixture after complexes have been formed. The various formats are described briefly below.

In a heterogeneous assay system, either the target protein or the interactive cellular or extracellular binding partner, is anchored onto a solid surface, while the non-anchored species is labelled, either directly or indirectly. In practice, microtiter plates are conveniently utilised. The anchored species may be immobilised by non-covalent or covalent attachments. Non-covalent attachment may be accomplished simply by coating the solid surface with a solution of the target gene product or binding partner and drying. Alternatively, an immobilised antibody specific for the species to be anchored may be used to anchor the species to the solid surface. The surfaces may be prepared in advance and stored.

In order to conduct the assay, the partner of the immobilised species is exposed to the coated surface with or without the test compound. After the reaction is complete, unreacted components are removed (e.g. by washing) and any complexes formed will remain immobilised on the solid surface. The detection of complexes anchored on the solid surface can be accomplished in a number of ways. Where the non-immobilised species is pre-labelled, the detection of label immobilised on the surface indicates that complexes were formed. Where the non-immobilised species is not pre-labelled, an indirect label can be used to detect complexes anchored on the surface, e.g. using a labelled antibody specific for the initially non-immobilised species (the antibody, in turn, may be directly labelled or indirectly labelled with a labelled anti-Ig antibody). Depending upon the order of addition of reaction components, test compounds which inhibit complex formation or which disrupt pre-formed complexes can be detected.

Alternatively, the reaction can be conducted in a liquid phase in the presence or absence of the test compound, the reaction products separated from unreacted components, and complexes detected, e.g. using an immobilised antibody specific for one of the binding components to anchor any complexes formed in solution, and a labelled antibody specific for the other partner to detect anchored complexes. Again, depending upon the order of addition of reactants to the liquid phase, test compounds which inhibit complex or which disrupt pre-formed complexes can be identified.

In an alternate embodiment of the invention, a homogeneous assay can be used. In this approach, a pre-formed complex of the target protein and the interactive cellular or extracellular binding partner is prepared in which either the target protein or its binding partners is labelled, but the signal generated by the label is quenched due to complex formation (see, e.g. U.S. Pat. No. 4,109,496 which utilises this approach for immunoassays). The addition of a test substance that competes with and displaces one of the species from the pre-formed complex will result in the generation of a signal above background. In this way, test substances, which disrupt target protein/cellular or extracellular binding partner interaction, can be identified.

In a particular embodiment, the target protein can be prepared for immobilisation using recombinant DNA techniques described in Section 2.1. For example, the target protein gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practised in the art and described above, in Section 2.1. This antibody can be labelled with the radioactive isotope $^{125}$I, for example, by methods routinely practised in the art. In a heterogeneous assay, e.g. the GST-target protein gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labelled monoclonal antibody can be added to the system and allowed to bind to the complexed components. The interaction between the target protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target protein gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the target protein/binding partner interaction can be detected by adding the labelled antibody and measuring the radioactivity associated with the beads.

In another embodiment of the invention, these same techniques can be employed using peptide fragments that correspond to the binding domains of the target protein and/or the interactive cellular or extracellular binding partner (in cases where the binding partner is a protein), in place of one or both of the full length proteins. Any number of methods routinely practised in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labelled binding partner, which has been treated with a proteolytic enzyme, such as trypsin. After washing, a short, labelled peptide comprising the binding domain may remain associated with the solid material, which can be isolated and identified by amino acid sequencing. Also, once the gene coding for the cellular or extracellular binding partner is obtained, short gene segments can be engineered to express peptide fragments of the protein, which can then be tested for binding activity and purified or synthesised.

For example, and not by way of limitation, a target protein can be anchored to a solid material as described above, in this Section by making a GST-target protein gene fusion protein and allowing it to bind to glutathione agarose beads. The interactive cellular or extracellular binding partner can be labelled with a radioactive isotope, such as $^{35}$S, and cleaved with a proteolytic enzyme such as trypsin. Cleavage products can then be added to the anchored GST-target protein gene fusion protein and allowed to bind. After washing away unbound peptides, labelled bound material, representing the cellular or extracellular binding partner binding domain, can be eluted, purified and analysed for amino acid sequence by well-known methods. Peptides so identified can be produced synthetically or fused to appropriate facilitative proteins using recombinant DNA technology.

3.4 Assays for Amelioration of Alzheimer's Disease Symptoms

Any of the binding compounds, including but not limited to, compounds such as those identified in the foregoing assay systems, may be tested for the ability to prevent or ameliorate Alzheimer's disease symptoms. Cell-based and animal model-based assays for the identification of compounds exhibiting such an ability to ameliorate Alzheimer's disease are described below.

First, cell-based systems such as those described above, in Section 2.2.2, may be used to identify compounds, which may act to prevent or ameliorate Alzheimer's disease symptoms. For example, such cell systems may be exposed to a compound, suspected of exhibiting an ability to ameliorate Alzheimer's disease, at a sufficient concentration and for a time sufficient to elicit such an amelioration of Alzheimer's disease symptoms in the exposed cells. After exposure, the cells are examined to determine whether one or more of the Alzheimer's disease-like cellular phenotypes has been altered to resemble a more normal or more wild type phenotype, or a phenotype more likely to produce a lower incidence or severity of disorder symptoms.

In addition, animals-based Alzheimer's disease systems, such as those described above, In Section 2.2.1, may be used to identify compounds capable of ameliorating Alzheimer's disease symptoms. Such animal models may be used as test substrates for the identification of drugs, pharmaceuticals, therapies and interventions which may be effective in treating such disorders. For example, animal models may be exposed to a compound, suspected of exhibiting an ability to prevent or ameliorate Alzheimer's disease symptoms, at a sufficient concentration and for a time sufficient to elicit such a prevention or amelioration of the Alzheimer's disease in the exposed animals. The response of the animals to the exposure may be monitored by assessing the reversal of disorders associated with Alzheimer's disease.

With regard to intervention, any treatments that reverse any aspect of Alzheimer's disease-like symptoms should be considered as candidates for human Alzheimer's disease therapeutic intervention. Dosages of test agents may be determined by deriving dose-response curves, as discussed in Section 6.1 below.

Similarly, any treatments that can prevent the development of Alzheimer's disease should be considered as candidates for the prevention of Alzheimer's disease therapeutic intervention.

Protein expression patterns may be utilised in conjunction with either cell-based or animal-based systems to assess the ability of a compound to ameliorate Alzheimer's disease-like symptoms. For example, the expression pattern of one or more fingerprint proteins may form part of a fingerprint profile, which may then be used in such as assessment. Fingerprint profiles are described below, in Section 7.1. Fingerprint profiles may be characterised for known states, either Alzheimer's disease or normal states, within the cell- and/or animal-based model systems. Subsequently, these known fingerprint profiles may be compared to ascertain the effect a test compound has to modify such fingerprint profiles, and to cause the profile to more closely resemble that of a more desirable fingerprint. For example, administration of a compound may cause the fingerprint profile of an Alzheimer's disease model system to more closely resemble the control system. Administration of a compound may, alternatively, cause the fingerprint profile of a control system to begin to mimic an Alzheimer's disease state, which may, for example, be used in further characterising the compound of interest, or may be used in the generation of additional animal models.

4. Compounds and Methods for Treatment of Alzheimer's Disease

Described below are methods and compositions whereby Alzheimer's disease symptoms may be ameliorated. It is possible that Alzheimer's disease may be brought about, at least in part, by an abnormal level of target protein, or by the presence of a target protein exhibiting an abnormal activity. As such, the reduction in the level and/or activity of such target protein would bring about the amelioration of Alzheimer's disease-like symptoms. Techniques for the reduction of target protein gene expression levels or target protein activity levels are discussed in Section 4.1.

Alternatively, it is possible that Alzheimer's disease may be brought about, at least in part, by the absence or reduction of the level of target protein expression, or a reduction in the level of a target protein=s activity. As such, an increase in the level of target protein gene expression and/or the activity of such proteins would bring about the amelioration of Alzheimer's disease-like symptoms. Techniques for increasing target protein gene expression levels or target protein activity levels are discussed in Section 4.2.

4.1 Compounds that Inhibit Expression, Synthesis or Activity of Mutant Target Proteins As discussed above, target proteins involved in Alzheimer's disease may cause such disorders via an increased level of target protein activity. A variety of techniques may be utilised to inhibit the expression, synthesis, or activity of such target genes and/or proteins.

For example, compounds such as those identified through assays described above, in Section 3, which exhibit inhibitory activity, may be used in accordance with the invention to prevent or ameliorate Alzheimer's disease symptoms. As discussed in Section 3 above, such molecules may include, but are not limited to, peptides (such as, for example, peptides representing soluble extracellular portions of target protein transmembrane receptors), phosphopeptides, small organic or inorganic molecules, or antibodies (including, for example, polyclonal, monoclonal, humanised, anti-idiotypic, chimeric or single chain antibodies, and FAb, $F(ab')_2$ and FAb expression library fragments, and epitope-binding fragments thereof). Techniques for determination of effective doses and administration of such compounds are described below, in Section 6.1. Inhibitory antibody techniques are further described below, in Section 4.1.2.

Further, antisense, siRNA and ribozyme molecules, which inhibit expression of the target protein gene, may also be used in accordance with the invention to inhibit the aberrant target protein gene activity. Such techniques are described below, in Section 4.1.1; triple helix molecules may be utilised in inhibiting the aberrant target protein gene activity.

4.1.1 Inhibitory Antisense, Ribozyme and Triple Helix Approaches

Among the compounds, which may exhibit the ability to prevent or ameliorate Alzheimer's disease symptoms are antisense, ribozyme and triple helix molecules. Such molecules may be designed to reduce or inhibit either wild type, or if appropriate, mutant target protein gene activity. Techniques for the production and use of such molecules are well known to those of skill in the art.

Antisense RNA and DNA molecules act to directly block the translation of mRNA by hybridising to targeted mRNA and preventing protein translation. With respect to antisense DNA, oligodeoxy-ribonucleotides derived from the translation initiation site, e.g. between the $-10$ and $+10$ regions of the target gene nucleotide sequence of interest, are preferred.

Ribozymes are enzymatic RNA molecules capable of catalysing the specific cleavage of RNA. (For a review, see Rossi, J., 1994, Current Biology 4: 469-471). The mechanism of ribozyme action involves sequence specific hybridisation of the ribozyme molecule to complementary target RNA, followed by a endonucleolytic cleavage. The composition of ribozyme molecules must include one or more sequences complementary to the target protein mRNA, and must include the well known catalytic sequence responsible for mRNA cleavage. For this sequence, see U.S. Pat. No. 5,093,246. As such, within the scope of the invention are engineered hammerhead motif ribozyme molecules that specifically and efficiently catalyse endonucleolytic cleavage of RNA sequences encoding target proteins.

Specific ribozyme cleavage sites within any potential RNA target are initially identified by scanning the molecule of interest for ribozyme cleavage sites which include the following sequences, GUA, GUU and GUC. Once identified, short TNA sequences of between 15 and 20 ribonucleotides corresponding to the region of the target protein gene, containing the cleavage site may be evaluated for predicted structural features, such as secondary structure, that may render the oligonucleotide sequence unsuitable. The suitability of candidate sequences may also be evaluated by testing their accessibility to hybridise with complementary oligonucleotides, using ribonuclease protection assays.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementary to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesised in an alternating 5'-3', 3'-5' manner, such that they base pair with first one strand of a duplex and then the other, eliminating the necessity for a sizeable stretch of either purines or pyrimidines to be present on one strand of a duplex.

Anti-sense RNA and DNA, ribozyme and triple helix molecules of the invention may be prepared by any method known in the art for the synthesis of DNA and RNA molecules. They include techniques for chemically synthesising oligodeoxyribonucleotides and oligo-ribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesise antisense RNA constitutively inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences or ribo- or deoxy-nucleotides to the 5' and/or 3' ends of the molecule or the use of phosphorothioate or 2' O-methyl rather than phosphodiesterase linkages within the oligodeoxy-ribonucleotide backbone.

4.1.2 Antibodies for the Inhibition of Target Protein

Antibodies that are both specific for target protein and interfere with its activity may be used to inhibit target protein function. Where desirable, antibodies specific for mutant target protein, which interferes with the activity of such mutant target product, may also be used.

Such antibodies may be generated using standard techniques described in Section 2.3, supra, against the proteins themselves or against peptides corresponding to portions of the proteins. The antibodies include, but are not limited to, polyclonal, monoclonal, Fab fragments, single chain antibodies, chimeric antibodies, etc.

In instances where the target gene protein is intracellular and whole antibodies are used, internalising antibodies may be preferred. However, lipofectin or liposomes may be used to deliver the antibody or a fragment of the Fab region, which binds to the target protein epitope into cells. Where fragments of the antibody are used, the smallest inhibitory fragment, which binds to the target protein=s binding domain, is preferred. For example, peptides having an amino acid sequence corresponding to the domain of the variable region of the antibody that binds to the target protein may be used. Such peptides may be synthesised chemically or produced via recombinant DNA technology using methods well known in the art (e.g. see Creighton, 1983, supra; and Sambrook et al, 1989, supra).

Alternatively, single chain neutralising antibodies, which bind to intracellular target protein epitopes, may also be administered. Such single chain antibodies may be administered, for example, by expressing nucleotide sequences encoding single-chain antibodies within the target cell populating by utilising, for example, techniques such as those described in Marasco et al (Marasco, W. et al, 1993, Proc. Natl. Acad. Sci. USA, 90: 7889-7893).

In instances where the target protein is extracellular, or is a transmembrane protein, any of the administration techniques described below, in Section 6, which are appropriate for peptide administration may be utilised to effectively administer inhibitory target protein antibodies to their site of action.

4.2 Methods for Restoring Target Protein Activity

Target proteins that cause Alzheimer's disease may be underexpressed. Alternatively, the activity of target protein may be diminished, leading to the development of Alzheimer's disease symptoms. Described in this Section are methods whereby the level of target protein may be increased to levels wherein Alzheimer's disease symptoms are prevented or ameliorated. The level of target protein activity may be increased, for example, by either increasing the level of target protein present or by increasing the level of active target protein, which is present.

For example, a target protein, at a level sufficient to ameliorate Alzheimer's disease symptoms may be administered to a patient exhibiting such symptoms. Any of the techniques discussed below, in Section 6, may be utilised for such administration. One of skill in the art will readily know how to determine the concentration of effective, non-toxic doses of the normal target protein, utilising techniques such as those described below, in Section 4.6.1.

Further, patients may be treated by gene replacement therapy. One or more copies of a normal target protein gene or a portion of the gene that directs the production of a normal target protein with target protein gene function, may be inserted into cells, using vectors which include, but are not limited to, adenovirus, adeno-associated virus, and retrovirus vectors, in addition to other particles that introduce DNA into cells, such as liposomes. Additionally, techniques such as those described above may be utilised for the introduction of normal target protein gene sequences into human cells.

Cells, preferably autologous cells, containing normal target protein gene sequences may then be introduced or reintroduced into the patient at positions which allow for the prevention or amelioration of Alzheimer's disease symptoms. Such cell replacement techniques may be preferred, for example, when the target protein is a secreted, extracellular protein.

Additionally, antibodies may be administered which specifically bind to a target protein and by binding, serve to, either directly or indirectly, activate the target protein function. Such antibodies can include, but are not limited to, polyclonal, monoclonal, FAb fragments, single chain antibodies, chimeric antibodies and the like. The antibodies may be generated using standard techniques such as those described above, in Section 2.3, and may be generated against the protein themselves or against proteins corresponding to portions of the proteins. The antibodies may be administered, for example, according to the techniques described above, in Section 4.1.2.

5. Pharmaceutical Preparations and Methods of Administration

The identified compounds, nucleic acid molecules and cells that affect target protein expression, synthesis and/or activity can be administered to a patient at therapeutically effective doses to prevent or to treat or to ameliorate Alzheimer's disease. A therapeutically effective dose refers to that amount of the compound sufficient to result in amelioration of symptoms of Alzheimer's disease, or alternatively, to that amount of a nucleic acid molecule sufficient to express a concentration of protein which results in the amelioration of such symptoms.

5.1 Effective Dose

Toxicity and therapeutic efficacy of such compounds can be determined by standard pharmaceutical procedures in cell cultures or experimental animals, e.g. for determining by $ED_{50}$ (the dose therapeutically effective in 50% of the population) and by determining the $ED_{50}$ of any side-effects (toxicity B TD50). The dose ratio between toxic and therapeutic effects is the therapeutic index and it can be expressed as the ratio $TD_{50}/ED_{50}$. Compounds, which exhibit large therapeutic indices, are preferred. While compounds that exhibit toxic side effects may be used, care should be taken to design a delivery system that targets such compounds to the site of affected tissue in order to minimise potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilised.

5.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral and rectal administration.

For oral administration, the pharmaceutical compositions may take the form of, for example, tablets or capsules prepared by conventional means with pharmaceutically acceptable excipients such as binding agents (e.g. pre-gelatinised maize starch, polyvinylpyrrolidone or hydroxypropyl methyl-cellulose); fillers (e.g. lactose, microcrystaklline cellulose or calcium hydrogen phosphate); lubricants (e.g. magnesium, stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of, e.g. gelatin, for use in an inhaler or insufflator may be formulated containing a powder mix of the compound and a suitable powder base such as lactose or starch.

The compounds may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation, for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

The compositions may, if desired, be presented in a pack or dispenser device, which may contain one or more unit dosage forms containing the active ingredient. The pack may, for example, comprise metal or plastic foil, such as blister pack. The pack or dispenser device may be accompanied by instructions for administration.

7. Diagnosis of Alzheimer's Disease

A variety of methods may be employed for the diagnosis of Alzheimer's disease, the predisposition to Alzheimer's disease, and for monitoring the efficacy of any Alzheimer's disease compounds during, for example, clinical trials and for monitoring patients undergoing clinical evaluation for the treatment of Alzheimer's disease. The fingerprint proteins can also be used to define the nature of Alzheimer's disease to aid in the identification and/or selection of treatments for the disorder.

Methods may, for example, utilise reagents such as the fingerprint protein described in Section 1, and antibodies directed against differentially expressed and pathway proteins, as described above, in Sections 1.3 (peptides) and 2.3 (antibodies). Specifically, such reagents may be used for (1) the detection of the presence of target protein mutations, or (2) the detection of either an over- or an under-abundance of target protein relative to the normal state.

The methods described herein may be performed, for example, by utilising pre-packaged diagnostic kits comprising at least one specific finger print protein or anti-fingerprint protein antibody reagent described herein, which may be conveniently used, e.g. in clinical settings, to diagnose patients exhibiting Alzheimer's disease abnormalities or symptoms.

Any cell type or tissue in which the fingerprint protein is expressed may be utilised in the diagnostics described below.

Examples of suitable samples types include cell samples, tissue samples, and fluid samples such as blood, urine or plasma.

Among the methods, which can be utilised herein, are methods for monitoring the efficacy of compounds in clinical trials for the treatment of Alzheimer's disease. Such compounds can, for example, be compounds such as those described above, in Section 4. Such a method comprises detecting, in a patient sample, a protein, which is differentially expressed in the Alzheimer's disease state relative to its expression in a normal state.

During clinical trials, for example, the expression of a single fingerprint protein, or alternatively, a fingerprint pattern of a cell involved in Alzheimer's disease can be determined in the presence or absence of the compound being tested. The efficacy of the compound can be followed by comparing the expression data obtained to the corresponding known expression patterns in a normal state. Compounds exhibiting efficacy are those which alter the single fingerprint protein expression and/or the fingerprint pattern to more closely resemble that of the normal state.

The detection of the protein differentially expressed in Alzheimer's disease relative to their expression in a normal state can also be used for monitoring the efficacy of potential Alzheimer's disease compounds and compounds for the treatment of Alzheimer's disease during clinical trials. During clinical trials, for example, the level and/or activity of the differentially expressed protein can be determined in relevant cells and/or tissues in the presence or absence of the compound being tested. The efficacy of the compound can be followed by comparing the protein level and/or activity data obtained to the corresponding known levels/activities for the cells and/or tissues in a normal state. Compounds exhibiting efficacy are those which alter the pattern of the cell and/or tissue involved in the Alzheimer's disease to more closely resemble that of the normal state.

Experimental

The expression of brain proteins in single (mutant APP or PS-1 transgenic) and double (mutant APP and PS1 transgenice) transgenic mice was compared with that of wild-type.
Identification of Differentially Expressed Proteins Using 2D Gel Electrophoresis
Samples A collection of frozen mouse samples were grouped according to genotype: [1] Double transgenic for the PS-1 and APP genes (denoted 'TT'), [2] Single transgenic for PS-1 gene (denoted 'WT'), [3] Single transgenic for APP gene (denoted 'TW'), and [4] wild-type control (no genetic modification, denoted 'WW'). Four to 10 mice were provided as replicates in each genotype group as shown in Table 1 and various brain regions (hippocampus, and the remainder of the hemisphere after dissection of hippocampus) were analysed.

TABLE 1 number of mice used for each genotype, IPG and tissue type.

| Genotype | Hippocampus | | ROH | |
|---|---|---|---|---|
| | IPG 4-7L n | IPG 6-9L n | IPG 4-7L n | IPG 6-9L n |
| APP (tw) | 3 | 4 | 8 | 8 |
| PS1 (wt) | 5 | 5 | 9 | 9 |
| APP/PS1 (tt) | 4 | 4 | 10 | 10 |
| Wildtype (ww) | 5 | 5 | 10 | 10 |

Brain sections were analysed from animals sacrificed at 14 weeks old, focusing on the material from the hippocampus. 2-DE was performed according to Weekes, J. et al (*Electrophoresis*, 20 (4-5):898-906, 1999) and Heinke, M. Y. et al (*Electrophoresis*, 20 (10):2086-2093, 1999). using pH 4-7L and pH 6-9L immobolised pH gradient (IPG) for both the hippocampus and ROH tissues. All pH 6-9 gradients strips were rehydrated in DeStreak rehydration solution (Amersham Biosciences) (Pennington, K et al., *Proteomics*, 4 (1): 27-30, 2004) and samples cuploaded at the anode. The second dimension was performed using 12% T SDS polyacrylamide gel electrophoresis.

Two-Dimensional Gel Electrophoresis
Protein Samples

Brain tissue samples solubilised in a volume of lysis buffer (9.5 M urea, 1% DTT, 2% CHAPS, 0.8% Pharmalyte pH3-10, containing "complete" protease inhibitor cocktail [Roche] at a 1:10 concentration) proportional to the mass of the tissue according to the ratio 1 mL lysis buffer per 100 mg tissue. 400 μg total protein was used for micro-preparative gel loadings from which protein spots of potential interest were cut for subsequent mass spectrometry analysis.
First-Dimension Isoelectric Focusing (IEF)

DeStreak rehydration solution (Amersham Biosciences) was used to rehydrate immobilised pH gradient (IPG) strips and samples cuploaded at the anode. Two different pH ranges were used. 18 cm IPG (linear) strips, covering the pH range 4-7 and 6-9, were used.
Second-Dimension SDS-PAGE Before the focused IPGs were run in the second dimension, the strips were equilibrated in buffer (1.5 M, pH 8.8, Tris [Genomic Solutions], 6 M urea [Gibco], 30% glycerol [BDH], 2% SDS [Genomic Solutions], 0.01% bromophenol blue [Sigma] containing 1% IAA [Sigma] for 15 minutes, followed by another 15 minutes in buffer containing 4.8% IAA [Sigma]. SDS-PAGE was performed overnight (20 mA/gel, 10° C.) using 12% T/2.6% C separating gels in a DALT system [Amersham Biosciences]. Acrylogel was supplied from BDH and SDS-PAGE running buffer chemicals (Tris, SDS, Glycine) were supplied from Genomic Solutions. All water used was of 18.2 MΩcm$^{-1}$ quality supplied from an Elga Maxima Life Sciences water purification unit.
Visualisation of 2-DE Protein Profiles Once the second dimension had been run, gels were fixed overnight (50% methanol, 10% acetic acid). Analytical gels were stained using a commercially available silver staining kit ('OWL', Insight Biotechnology Ltd.). Micro-preparative gels were stained using a mass spectrometry compatible silver stain ('Plus-One', Amersham Biosciences) following a modified protocol [1]. All water used was of 18.2 MΩcm$^{-1}$ quality supplied from an Elga Maxima Life Sciences water purification unit. After silver staining, all gels were scanned at 100 μm resolution using a Molecular Dynamics Personal Densitometer SI. The stained analytical gels were then used for comparative quantitative analysis and, following analysis, proteins of potential interest were localised to the relevant micro-preparative gel(s) from which the spots were cut and subjected to analysis by mass spectrometric analysis to allow the identity of the protein(s) present to be established.

Gel Image Analysis

Analysis of gel images was performed in several stages using Progenesis software, version 2003.2 (NonLinear Dynamics). Automatic image preparation (gel spot detection, gel image matching and warping, background subtraction and quantitative normalisation were performed overnight automatically by the software, followed by brief manual editing of gel images to generate matching accuracies of up to 75%. This was followed by detailed manual image editing as necessary to improve matching accuracies greater than 85% to enable comparative analysis to be undertaken, then detailed visual verification of all protein spots of potential interest found from the previous analysis. Following background subtraction and normalisation to total spot volume, protein spot data was exported to Excel for quantitative statistical analysis and comparisons of qualitative changes.

Quantitative Statistical Analysis

Student T-Test

Individual two-group comparisons, using Student's t-test, were performed at the 95% confidence interval. Each transgenic group was compared against the wildtype. For a spot to be included the statistical analysis, it was required to be present in at least 60% of the gels. To validate significant results, five groups containing a mixture of the genetypes included in the above comparisons were constructed randomly for each of the comparisons. A two-group comparison Student's t-test was then carried out on these mixed groups using the same criteria as above.

Principal Component Analysis (PCA)

PCA was applied to all the datasets. Analyses were performed initially on all the groups and subsequently on just the ww and tt groups. Spots included as variables were those present in at least 60% of gels from any one of the groups Common Spots Spots that were found to exhibit similar changes in expression in more than one transgenic group when compared with wild type were excised from silver stained micro-preparative gels and identified using LC/MS/MS.

Qualitative Spots

Spots that were present or absent in any one of the transgenic models when compared to wild type. The criteria used was each spot had to be present in at least 60% of the gels.

Enzymatic Digestion

In-gel reduction, alkylation and digestion (with trypsin) were performed prior to subsequent analysis by mass spectrometry. Cysteine residues were reduced with DTT and derivatized by treatment with iodoacetamide to form stable carbamidomethyl (CAM) derivatives. Trypsin digestion was carried out overnight at room temperature after an initial 1 hr incubation at 37° C.

MALDI-TOF MS

Where necessary the digested protein samples (4 µl) were desalted using ZipTip C18 microtips (Millipore). Peptides were eluted in 4 µl 50% acetonitrile/0.1% trifluoracetic acid. 0.5 µl was then loaded onto a target plate with 0.5 µl matrix (a-Cyano-4-hydroxy-cinnamic acid). Peptide mass fingerprints were acquired using a Voyager DE-PRO MALDI-TOF mass spectrometer (Applied Biosystems). The mass spectra were acquired in reflection mode with delayed extraction. An autolytic tryptic peptide of mass 2163.0569 Da was then used as an internal lock mass calibrant to achieve a mass accuracy of better than 50 ppm.

LC/MS/MS

Peptides were extracted from the gel pieces by a series of acetonitrile and aqueous washes. The extract was pooled with the initial supernatant and lyophilised. Each sample was then resuspended in 7 µl of 50 mM ammonium bicarbonate and analysed by LC/MS/MS. Chromatographic separations were performed using an Ultimate LC system (Dionex, UK). Peptides were resolved by reversed phase chromatography on a 75 µm C18 PepMap column. A gradient of acetonitrile in 0.05% formic acid was delivered to elute the peptides at a flow rate of 200 nl/min. Peptides were ionised by electrospray ionisation using a Z-spray source fitted to a Qtof-micro (Walters Corp, USA). The instrument was set to run in automated switching mode, selecting precursor ions based on their intensity, for sequencing by collision-induced fragmentation. The MS/MS analyses were conducted using collision energy profiles that were chosen based on the m/z and the charge state of the peptide.

Database Searching

The mass spectral data was processed into peptide mass lists (MALDI data) and peak lists (MS/MS data) and searched against the Swiss Prot Database version 43 (current as of March 2004) using Mascot software (Matrix Science, UK). Carbamidomethyl© and oxidation (M) were set as variable modifications within the searching parameters. A high level of confidence can be assigned to these protein identities because the results are based on exact matching of MS/MS data for multiple peptides from each protein.

Results

Gel Image Analysis

Gel images were matched to each other, at the replicate image level, with 87% accuracy (see table 1). The so-called averaged gel images (from each of the replicate groups) were then matched to each other with 90% accuracy (see table 2).

Quantitative Statistical Analysis

Student T Test

Only the hippocampus pH 6-9 (ww vs. tw) and pH 4-7 (ww vs. tt) produced a greater number of significant differences than would be expected by chance alone (highlighted in dark grey, Table 2). The numbers highlighted in pale grey (Table 2) indicate the number of apparent genuine significant spots.

TABLE 2

For the hippocampus pH 4-7 (ww vs tt), 62 spots were visually verified and of these, 25 were considered for analysis by LC MS/MS. For the hippocampus pH 6-9 (ww vs tw), 22 spots were visually verified and 7 of these were considered for analysis by LC MS/MS.

| IPG | Hippocampus | total spots | $P \leq 0.05$ 5% |
|---|---|---|---|
| 4-7 | ww (3/5 gels) vs tt (3/4 gels) | 609 | |
| | Spots changing by chance | | 30 |
| | Number of significant spots | | 62 |
| | Number of apparent genuine significant spots | | 32 |
| | FGA (n = 5) | | 32 |
| 6-9 | ww (3/5 gels) vs tw (3/4 gels) | 292 | |
| | Spots changing by chance | | 15 |
| | Number of significant spots | | 44 |
| | Number of apparent genuine significant spots | | 7 |
| | FGA (n = 5) | | 13 |

Principal Component Analysis

Figure 2:
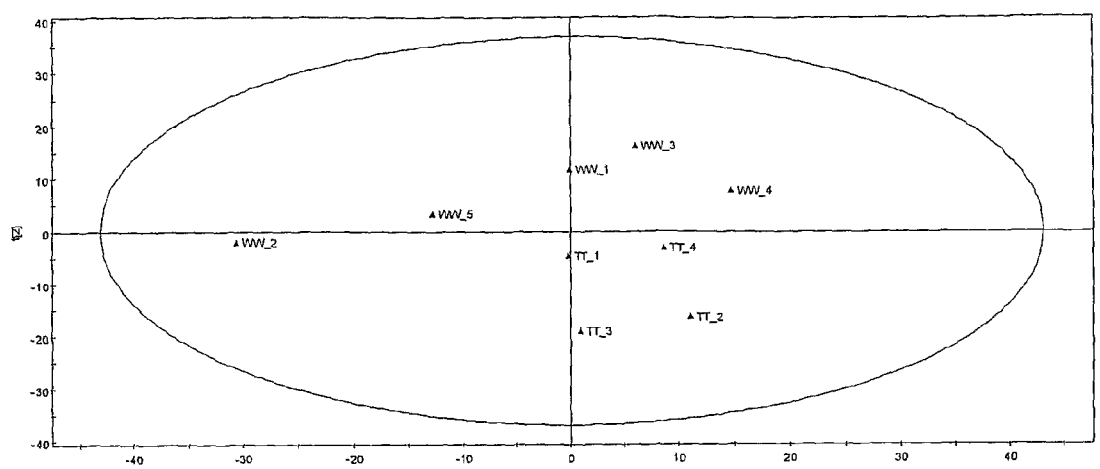
FIG. 2 shows a PCA scores plot showing the first two principal components in the analysis of the ww and tt groups (hippocampus tissue of a 4-7 gels). Horizontal axis: within group variation. Vertical axis: between group variation FIG. 3 gives details of the proteins identified in the 3 spots showing qualitative changes. Provided amino acid sequences are SEQ ID NOs: 1 and 2, from top to bottom.

Inspection of the majority of the PCA scores plots did not reveal clear clusters correlating with the group membership. An exception to this was the comparison of ww and tt in the hippocampus 4-7 gels. (FIG. 2)

Common Spots

A total of 19 spots, present in more than one transgenic group when compared to wild type were found to be statistically significant (p≤0.05) and displayed similar fold-change in their expression (FIG. 7).

Qualitative Changes

Three spots showed qualitative changes (i.e. were present in only one group). For the hippocamupus 4-7 gels, there were 2 qualitative changes. One of these spots was present only in the wild type (ww) and absent from the other three genotypes. The other was absent in the double transgenic group (tt) but present in the other three genotypes. For the hippocampus 6-9 gels, one spot was present only in the wild type (ww) group Conclusions In Alzheimer's Disease the main changes in protein expression are thought to occur in regions of the brain involved with learning and memory. For this reason analysis of protein changes has been focused within the hippocampus tissue. Protein separation by 2D gel electrophoresis using pH 44-7 and 6-9 IPG first dimension conditions has enabled a display of over one thousand protein spots being expressed by this tissue. Comprehensive image analysis to compare the protein expression between wild type and double transgenic animals has indicated that for hippocampus and ROH, a total of 47 protein spots showed significant changes in their expression across the two different gradients, pH 4-7 and pH 6-9:—

3 qualitative changes were found (FIG. 3).

Figure 4A:
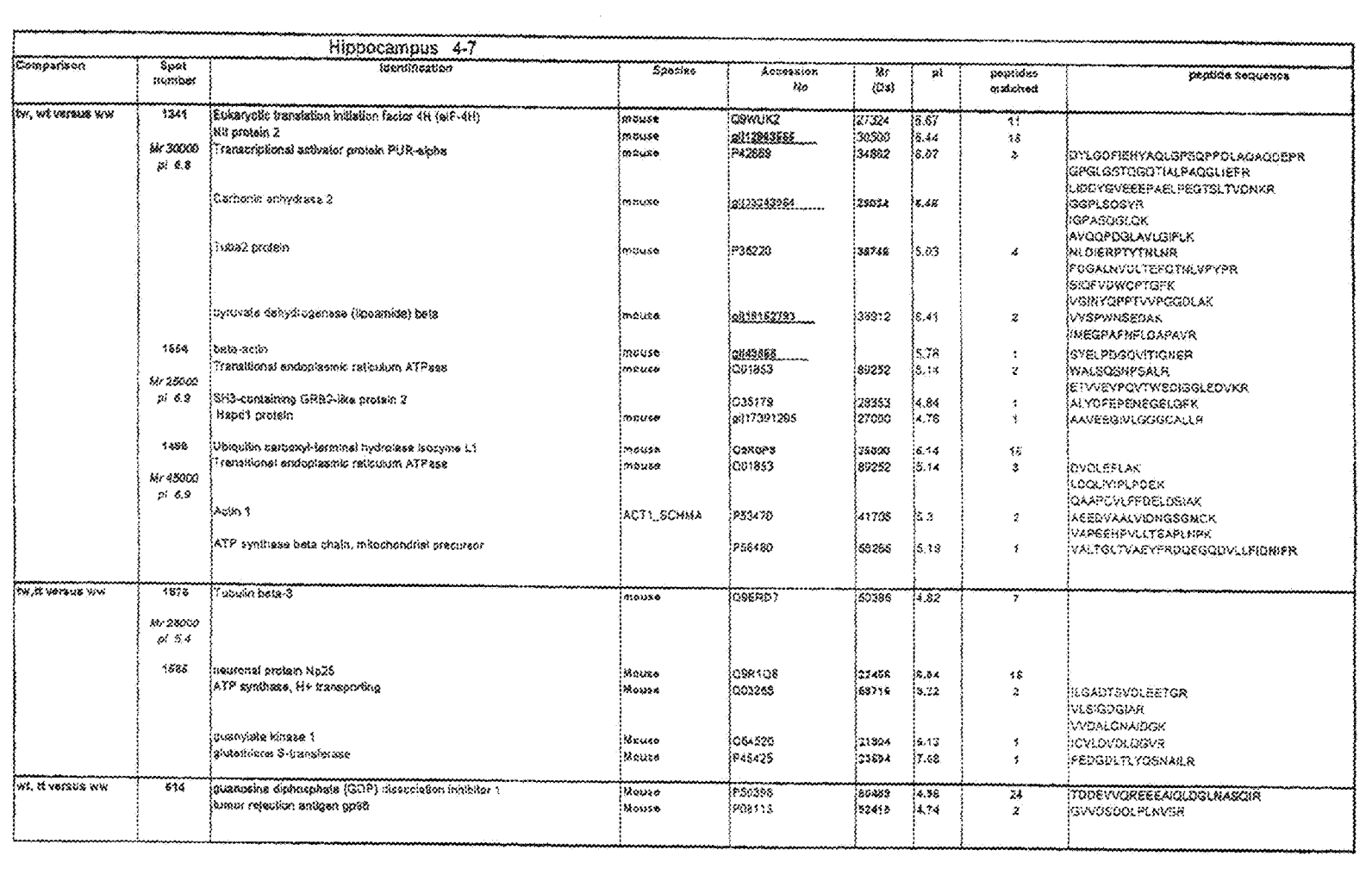

28 spots have been identified in the hippocampus pH 4-7 (FIGS. 4A and 4B).

Figure 5A:
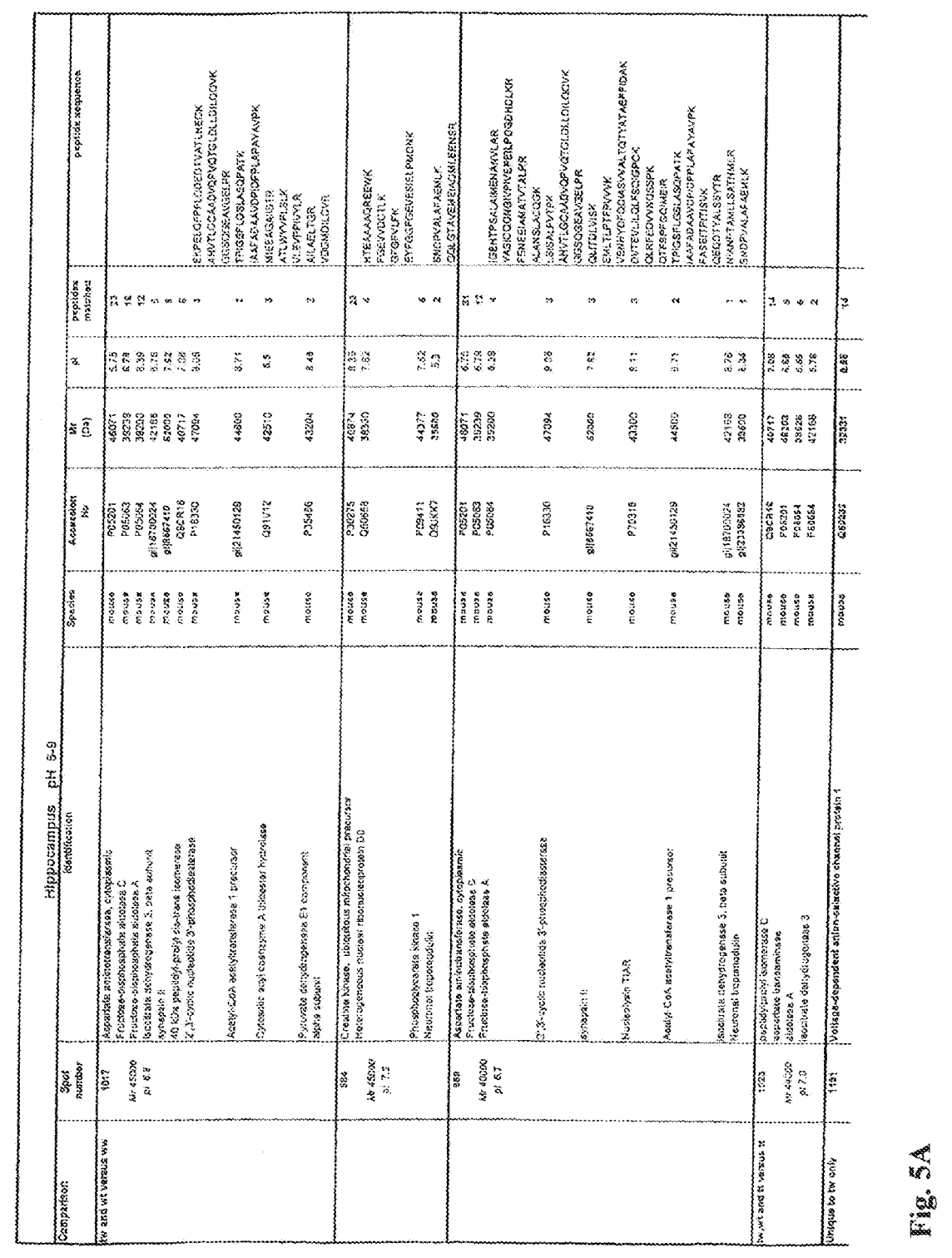

7 spots have been identified in the hippocampus pH 6-9 (FIGS. 5A and 5B)

5 spots have been identified in the ROH pH 4-7 (FIG. 6).

19 of the above protein spots appear in more than one transgenic group compared to the wild type, 22 spots are unique to tt (4-7L IPG hippocampus) and 3 spots are unique to tw (6-9L IPG hippocampus)

Subsequent analysis of these spots by mass spectrometry and database searching has revealed the identity of multiple protein components present in each of the samples. FIGS. 8A and 8B highlight some of the key proteins which may be involved in the pathogenesis of AD.

Identification of Differentially Expressed Proteins Using SELDI Mass Spectrometry Sample Preparation.

Blood was taken from transgenic mice and wild-type mice (n=18) at 14 weeks and plasma samples were diluted in 9.5 M urea, 2% CHAPS, 1% DTT.

Surface Enhanced Laser Desorption Ionisation (SELDI) Mass Spectrometry.

Profiling of the plasma samples was performed using an eight spot strong anion exchange (Q10) protein chip array. All samples were run in duplicate and in a randomised manner. Q10 chips were equilibrated four times in 100 mM Tris HCl pH 9.0. Five microliters of the diluted samples were applied to each spot and the chips were incubated in a humidity chamber for 45 minutes. Samples were carefully removed and the chips were washed four times in 100 mM Tris HCl pH 9.0, followed by one wash with 18.2 MΩ water. Matrix solution (Sinnapinic acid-20 mg/mL) was prepared in 50% acetonitrile and 0.5% trifluoroacetic acid and applied to each spot as two 0.6 µL aliquots. Data acquisition was performed using a PBS-IIc reader (Ciphergen Biosystems). Spectra were acquired using a summation of 155 shots with a laser intensity of 200, detector sensitivity of 8 and a focus mass of 25000. Baseline subtraction and normalisation to total ion count were performed on all the spectra. Internal calibration of the spectra was undertaken using a minimum of two peaks in each spectrum.

Multivariate Data Analysis

Data Export and Pre-Processing.

For the multivariate analysis the raw spectra were exported in comma separated value (csv) format and an in-house program (SMSS_0_3) was run on the each of the raw spectra to align intensity values for corresponding masses in each spectrum. The individual processed spectral data were compiled into a single Excel (Microsoft) spreadsheet for import into SIMCA-P (Umetrics). The variables corresponding to masses between m/z 0 and m/z 100,000 were centred to the mean value and Pareto scaled.

Principal Component Analysis (PCA).

PCA models were fitted to the data sets with as many components (A) as would fit following the internal rules SIMCA-P uses to determine the significance of the components (Eriksson et al. 2001). The goodness of fit ($R^2$) and goodness of prediction ($Q^2$) parameters were used to assess the usefulness of each of the subsequent components fitted in the model. The automatically fitted components were inspected and kept as long as the $Q^2$ parameter was increasing. The cumulative $R^2$ parameter for the final accepted component gave the total proportion of variance in the data explained by the model. Plots were produced displaying the observation scores (t) and variable loadings (p) for pairs of principal components (a). The scores plots were inspected to look for patterns of systematic variation and outlying observations that could hamper later classification efforts. In particular, the positions of observations analysed on each chip were scrutinised to check for unusual chips. The reproducibility of duplicated sample analyses were also checked using the scores plots. The Ellipse on the scores plots corresponds to Hotelling's $T^2$ at 95%, a multivariate adaptation of a confidence region. For a data set with a multivariate normal distribution, 95% of the observations would be expected to lie within the region encompassed by the Ellipse, thus observations that are a long way outside the ellipse may represent problems to be investigated and addressed. Trends found through inspection of the scores plots were interpreted through inspection of the variables found on the corresponding loadings plots. Individual m/z values plotted at the extremes of the plot were considered to be most influential on the separation of the groups. Interestingly, such plots tend to show several consecutive m/z data points, which effectively describe the original peak observed in the SELDI profiles themselves.

Partial Least Squares-Discriminant Analysis (PLS-DA) and Modelling.

Components (A) of PLS-DA models were fitted to the data sets as long as they met the criteria used by SIMCA-P to determine the significance of components (Eriksson et al. 2001). As for the PCA modelling, the $R^2$ and $Q^2$ parameters were inspected to determine which components should be included in the model. Unlike the PCA modelling, PLS-DA models posses $R^2$ values describing the fit of the model to both the X (measurement) variables and the Y (class) variables. Plots were produced displaying the observation scores (t) and the variable weights (w*c) for pairs of PLS components (a). Because each PLS component is fitted so as to both approximate the X and Y data well and maximize the correlation between the X and Y data, in practice the first one or two components usually separate the observations well when there are few groups present in the data set. The interpretation of the PLS scores and weights plots is similar to that used to interpret a PCA model, with the PLS weights being analogous to the PCA loadings. Hotelling's $T^2$ was computed and displayed on all PLS scores plots to help identify deviating observations.

Cross-Validation.

The ability of the PLS-DA models generated to correctly predict the class of (new) samples was determined by 2-fold cross-validation. Cross-validation was performed by dividing the data set into a training and a test set (odd numbers were used for the training set and even numbers were used for the test set). A PLS-DA model was fitted to the training portion of the data set and subsequently used to predict the classes of the test portion of the data set. The training and test data sets were then switched and the process repeated. The number of correct and incorrect classifications from both rounds of testing were recorded and used to calculate sensitivities and specificities of the predictions.

Variable Selection.

The two parameters referred to as variable influence on projection (VIP) and PLS-coefficients (COEFF) were used to determine which m/z values were most important in defining the model and explaining the groups. Specific thresholds were determined empirically and used to exclude those variables with VIP and COEFF values lower than the threshold. The above cross-validation methods were applied to PLS-DA models fitted to data sets containing selected variables.

Uni-Variate Data Analysis

Automatic peak detection and matching was performed on all spectra and this data was then submitted to the Biomarker Wizard module for statistical significance testing using the Mann-Whitney test. Peaks with p≤0.05 were visually inspected to check that they corresponded to signal peaks and not to baseline noise. The accepted peaks were manually marked and the substance mass and intensity data for these peaks were exported to Excel to calculate the fold change for each peak. Because of the skewed distributions observed for the areas or intensities of each set of matched peaks, the data were $\log_{10}$ transformed prior to calculation of the mean and median values of the distributions as well as the standard deviations. The parameters of the distributions were then transformed back onto the original scales in order to calculate fold-changes and effect sizes (Cohen's D). Effect size was calculated as the difference between the mean values of two groups divided by the pooled standard deviation.

Primary Potential Biomarkers

To be considered as a primary potential marker of interest, each biomarker (peak) had to satisfy the following three criteria. The peaks were selected according to their VIP and COEFF parameters, following PLS-DA. The differences between the mean peak intensities of each group were statistically significant (p≤0.05) by a Mann-Whitney test. The difference between the mean and median peak intensities of the groups were ≥1.5 fold increased or decreased.

Table 3 shows the primary potential biomarkers observed in each of the comparisons. The table describes the mean and median fold change and the direction of change in each of the comparisons, in relation to wild type.

TABLE 3

| Candidate Identifier | Peak Apex (m/z) | P value | Mean fold change | Median fold change | direction |
|---|---|---|---|---|---|
| P1 | 3772 | 0.01 | 2.3 | 3.1 | Increase |
| P2 | 3897 | 0.02 | 5.5 | 36 | in |
| P3 | 4013 | 0.01 | 2.2 | 3.4 | double |
| P4 | 8618 | 0.004 | 1.6 | 1.5 | transgenic |
| P5 | 8832 | 0.01 | 1.6 | 1.9 | (APP/PS1) |
| P6 | 9172 | 0.027 | 2.1 | 2.2 | Decrease in double transgenic (APP/PS1) |
| P7 | 15122 | 0.035 | 1.5 | 1.5 | Increase |

TABLE 3-continued

| Candidate Identifier | Peak Apex (m/z) | P value | Mean fold change | Median fold change | direction |
|---|---|---|---|---|---|
| | | | | | in single transgenic (PS1) |
| P6 | 9172 | 0.038 | 3.8 | 8.2 | Decrease in single transgenic (PS1) |
| P8 | 9321 | 0.023 | 1.7 | 1.5 | Decrease in single transgenic (PS1) |
| P1 | 3772 | 0.01 | 1.7 | 1.9 | Increase in single transgenic (APP) |
| P9 | 4700 | 0.02 | 1.7 | 2.4 | Decrease in single transgenic (APP) |

Secondary Potential Biomarkers

Two types of secondary potential biomarker lists were created based on either the multivariate or univariate analysis.

The first list is based on the multivariate analysis (Table 4). The peaks of interest were selected by variable selection for each of the comparisons, however these peaks were not coupled with a p-value of ≤0.05.

TABLE 4

| Candidate Identifier | Peak Apex (m/z) | P values | Mean fold change | Median fold change | direction |
|---|---|---|---|---|---|
| P10 | 4050 | 0.8 | 1.3 | 1.1 | Decrease in |
| P11 | 4335 | 0.08 | 1.8 | 1.5 | double |
| P12 | 4610 | 0.35 | 1.4 | 1.2 | transgenic |
| P13 | 4775 | 0.20 | 1.4 | 1.1 | (APP/PS1) |
| P14 | 6616 | 0.92 | 1.1 | 1.0 | |
| P15 | 8051 | 0.07 | 1.3 | 1.2 | |
| P16 | 11279 | 0.049 | 1.4 | 1.4 | |
| P17 | 11775 | 0.33 | 1.2 | 1.2 | |
| P18 | 18090 | 0.13 | 1.4 | 1.5 | |
| P19 | 3408 | 0.49 | 1.4 | 1.3 | Increase in single transgenic (PS1) |
| P2 | 3897 | 0.13 | 2.8 | 6.9 | Increase in single transgenic (PS1) |
| P3 | 4013 | 0.19 | 1.6 | 1.6 | Increase in single transgenic (PS1) |
| P14 | 6616 | 1 | 1.3 | 1.2 | Increase in single transgenic (PS1) |
| P20 | 7264 | 0.60 | 1.4 | 1.1 | Increase in single transgenic (PS1) |
| P17 | 11755 | 0.19 | 1.3 | 2.7 | Increase in single transgenic (PS1) |
| P21 | 11925 | 0.18 | 1.5 | 2.9 | Increase in single transgenic (PS1) |
| P22 | 14510 | 0.227 | 1.5 | 1.0 | Increase in single |

TABLE 4-continued

| Candidate Identifier | Peak Apex (m/z) | P values | Mean fold change | Median fold change | direction |
|---|---|---|---|---|---|
| P23 | 4244 | 0.76 | 1.3 | 1.1 | Decrease in single transgenic (PS1) |
| P24 | 4432 | 0.53 | 1.3 | 1.1 | Decrease in single transgenic (PS1) |
| P25 | 4500 | 0.73 | 1.2 | 1.1 | Decrease in single transgenic (PS1) |
| P12 | 4610 | 0.37 | 1.3 | 1.2 | Decrease in single transgenic (PS1) |
| P13 | 4775 | 0.58 | 1.4 | 1.1 | Decrease in single transgenic (PS1) |
| P26 | 8560 | 0.43 | 1.0 | 1.1 | Decrease in single transgenic (PS1) |
| P27 | 9063 | 0.28 | 1.3 | 1.5 | Decrease in single transgenic (PS1) |
| P28 | 9372 | 0.01 | 4.7 | 8.1 | Decrease in single transgenic (PS1) |
| P18 | 18090 | 0.34 | 1.2 | 1.4 | Decrease in single transgenic (PS1) |
| P19 | 3408 | 0.49 | 1.4 | 1.3 | Decrease in single transgenic (PS1) |
| P2 | 3897 | 0.13 | 2.8 | 6.9 | Decrease in single transgenic (PS1) |
| P3 | 4013 | 0.19 | 1.6 | 1.6 | Decrease in single transgenic (PS1) |
| P14 | 6616 | 1 | 1.3 | 1.2 | Decrease in single transgenic (PS1) |
| P20 | 7264 | 0.60 | 1.4 | 1.1 | Decrease in single transgenic (PS1) |
| P30 | 3758 | 0.31 | 1.4 | 1.4 | Increase in single transgenic mouse (APP) |
| P31 | 4097 | 0.40 | 1.1 | 1.2 | Increase in single transgenic mouse (APP) |
| P32 | 4224 | 0.79 | 1.1 | 1.5 | Increase in single transgenic mouse (APP) |
| P4 | 8618 | 0.16 | 2.2 | 1.9 | Increase in single transgenic mouse (APP) |
| P33 | 8642 | 0.73 | 1.1 | 1.0 | Increase in single transgenic mouse (APP) |
| P34 | 8658 | 0.70 | 1.1 | 1.1 | Increase in single transgenic mouse (APP) |
| P35 | 14474 | 0.97 | 1.1 | 1.4 | Increase in single transgenic mouse (APP) |
| P7 | 15122 | 0.62 | 1.1 | 1.0 | Increase in single transgenic mouse (APP) |
| P29 | 3741 | 0.99 | 1.2 | 1.6 | Decrease in single transgenic mouse (APP |
| P36 | 3530 | 0.34 | 1.1 | 1.0 | Decrease in single transgenic mouse (APP |
| P37 | 3817 | 0.38 | 1.3 | 1.3 | Decrease in single transgenic mouse (APP |
| P38 | 4000 | 0.22 | 1.3 | 1.1 | Decrease in single transgenic mouse (APP |
| P39 | 4082 | 0.01 | 1.0 | 1.3 | Decrease in single transgenic mouse (APP |
| P25 | 4500 | 0.62 | 1.2 | 1.2 | Decrease in single transgenic mouse (APP |
| P13 | 4775 | 0.70 | 1.3 | 1.2 | Decrease in single transgenic mouse (APP |
| P17 | 11775 | 0.16 | 1.6 | 1.6 | Decrease in single transgenic mouse (APP |
| P21 | 11925 | 0.49 | 1.4 | 1.1 | Decrease in single transgenic mouse (APP |

The second list (Table 5) is based on the univariate analysis whereby the potential biomarker satisfied the following criteria:

The differences between the mean peak intensities of each group were statistically significant ($p \leq 0.05$) by a Mann-Whitney test.

The difference between the mean and median peak intensities of the groups were $\geq 1.5$ fold increased or decreased.

TABLE 5

| Candidate Identifier | Peak Apex (m/z) | P values | Mean fold change | Median fold change | direction |
|---|---|---|---|---|---|
| P40 | 3531 | 0.03 | 1.6 | 1.8 | Increase in double transgenic (APP/PS1) |
| P41 | 4155 | 0.01 | 2.7 | 3.4 | |
| P42 | 4217 | 0.04 | 1.6 | 2.1 | |
| P43 | 4254 | 0.04 | 1.5 | 1.8 | |
| P44 | 4513 | 0.04 | 2.0 | 1.8 | |
| P45 | 15723 | 0.05 | 1.4 | 1.5 | |

TABLE 5-continued

| Candidate Identifier | Peak Apex (m/z) | P values | Mean fold change | Median fold change | direction |
|---|---|---|---|---|---|
| P46 | 3624 | 0.01 | 1.5 | 1.5 | Decrease in double transgenic (APP/PS1) |
| P26 | 8560 | 0.03 | 1.5 | 1.8 | |
| P47 | 36069 | 0.04 | 2.0 | 2.17 | |
| P48 | 7571 | 0.049 | 1.5 | 1.3 | Increase in Single transgenic (PS1) |
| P49 | 14372 | 0.038 | 1.7 | 1.3 | Increase in Single transgenic (PS1) |
| P45 | 15723 | 0.05 | 1.7 | 1.7 | Increase in Single transgenic (PS1) |
| P46 | 5658 | 0.01 | 1.5 | 1.4 | Decrease in Single transgenic PS1 |
| P47 | 11339 | 0.038 | 1.5 | 1.6 | Decrease in Single transgenic PS1 |
| P48 | 3326 | 0.01 | 1.6 | 1.5 | Increase in Single transgenic APP |
| P3 | 4013 | 0.01 | 2.1 | 3.6 | Increase in Single transgenic APP |
| P41 | 4155 | 0.004 | 3.7 | 5.4 | Increase in Single transgenic APP |
| P42 | 4217 | 0.02 | 1.7 | 1.5 | Increase in Single transgenic APP |
| P43 | 4254 | 0.06 | 1.9 | 2.8 | Increase in Single transgenic APP |
| P44 | 4513 | 0.01 | 2.1 | 3.5 | Increase in Single transgenic APP |
| P12 | 4610 | 0.012 | 2.3 | 3.1 | Increase in Single transgenic APP |
| P49 | 8065 | 0.02 | 1.5 | 1.4 | Increase in Single transgenic APP |
| P50 | 10380 | 0.01 | 1.6 | 1.5 | Increase in Single transgenic APP |
| P51 | 2960 | 0.03 | 1.4 | 1.5 | Decrease in Single transgenic APP |
| P52 | 4660 | 0.012 | 1.2 | 1.3 | Decrease in Single transgenic APP |
| P53 | 8155 | 0.0005 | 1.5 | 1.4 | Decrease in Single transgenic APP |

Peaks which appear in two or more of the transgenic groups are peaks 6, 2, 3, 4, 6, 7, 12, 13, 14, 16, 18, 21, 25, 26, 41, 42, 45.

Identification of the components that correspond to the peaks of interest classified as primary potential biomarkers is described below.

Further Analysis of SELDI Peaks

The peaks identified as primary potential biomarkers in the double transgenic mice were subjected to further analysis to identify the proteins therein. This was carried out by extracting plasma material from the SELDI protein chips and separating the component proteins on a 1-D gel. Proteins were visualised using an MS-compatible silver stain and gel bands of molecular weights equivalent to the m/z values for several SELDI peaks of interest were excised. Proteins were identified using an in-gel digestion technique and LC/MS/MS. Following identification of proteins, an attempt was made to rationalise the identities using the BioLynx analysis tool within the MassLynx software suite. In this analysis, it was possible to confirm the presence of identified fragments of proteins in SELDI peaks of interest.

Extraction of Plasma Sample Material from SELDI Protein-Chips

Plasma material was extracted from Q10 proteinchips (strong anion exchange chromatography) by up/down pipetting of 5 µL hot Laemmli buffer for 1 min. (Samples were pooled to their relevant genotype groupings). This method of extraction was found to be very effective in removing material bound to the proteinchip since no peaks were observed when the post-extracted spots were re-read in the SELDI machine.

SDS-PAGE

Wild-type (WW) and double transgenic (TT) proteinchip extracts were resolved by SDS-PAGE using a 1.5 mm thick 16% tris-glycine 1-D gel (Invitrogen) in a NOVEX protein electrophoresis apparatus (Invitrogen). The 16% gel was used to achieve adequate physical separation and resolution of bands in the sub-27 kDa region which corresponds to the molecular weight of the majority of SELDI peaks of interest. The gel was run for 1 hour at 80 V and then 120 V for 1½ hours until the bromophenol blue dye-front reached the bottom of the gel. Following electrophoresis the gel was stained using a mass spectrometry compatible silver stain (modified Plus One kit [GE Healthcare]) and scanned using a 'Personal Densitometer SI' (Molecular Dynamics) in order to acquire a digital image.

Identification of Proteins

Enzymatic Digestion

Gel bands of molecular weights corresponding to the m/z values of SELDI peaks of interest were manually excised. In-gel reduction, alkylation, and digestion (with trypsin) were performed prior to subsequent analysis by mass spectrometry. Cysteine residues were reduced with DTT and derivatized by treatment with iodoacetamide to form stable carbamidomethyl (CAM) derivatives. Trypsin digestion was carried out overnight at room temperature after an initial 1 hr incubation at 37° C.

LC/MS/MS

Peptides were extracted from the gel pieces by a series of acetonitrile and aqueous washes. The extract was pooled with the initial supernatant and lyophilised. Each sample was then resuspended in 23 µL of 50 mM ammonium bicarbonate and analysed by LC/MS/MS. Chromatographic separations were performed using an Ultimate LC system (Dionex, UK). Peptides were resolved by reversed phase chromatography on a 75 µm C18 PepMap column. A gradient of acetonitrile in 0.05% formic acid was delivered to elute the peptides at a flow rate of 200 nL/min. Peptides were ionised by electrospray ionisation using a Z-spray source fitted to a QT of-micro (Micromass, UK). The instrument was set to run in automated switching mode, selecting precursor ions based on their intensity, for sequencing by collision-induced fragmentation. The MS/MS analyses were conducted using collision energy profiles that were chosen based on the m/z and the charge state of the peptide.

Database Searching

The mass spectral data peak lists (MS/MS data) were searched against the Swiss Prot or NCBI non-redundant databases using Mascot software (Matrix Science, UK). The data was searched using specific amino acid modification parameters, i.e. variable cysteine caramidomethylation modification (resulting from reduction and alkylation reaction) and variable methionine oxidation modification.

Analysis of Protein Fragments (BioLynx)

Seven SELDI peaks of prime interest were analysed using the BioLynx module of the MassLynx software suite. The amino acid sequence for each identified protein was analysed using BioLynx so as to predict the likelihood of fragments of the protein under investigation being generated that match the masses of the SELDI peaks of interest. Furthermore, the amino acid sequence for each predicted fragment was checked with the observed LC/MS/MS fragment in Mascot. Essentially, using BioLynx in this manner enables the confirmation of the likely existence of a fragment of a given protein the mass of which matches the SELDI peak mass of interest. Proteins of which fragments appear in multiple peaks are potentially of greatest interest as biomarkers.

Results

Several well resolved faint bands particularly in the sub-14 kDa region were visible on SDS-page. Twenty two gel bands were manually excised from the TT gel lanes covering the 3-11 kDa region for MS analysis. Each pair of bands, e.g. TT11 and TT27, were collected to one Eppendorf tube and cut into ~1 mm cubes. Following such poolings eight samples were analysed by LC-MS/MS. Taking the complete dataset, which encompasses the analysis of the eight samples, it was possible to identify 65 proteins in total (Table 6); however, many of these are present in multiple gel bands and so just 24 unique proteins are shown to be present (Table 7). This suggested that presence of multiple fragmented forms of the proteins were present.

TABLE 6

| Sample | Approx. gel MWs (Da) | Protein ID | Species | SWISS-PROT A/C No. | Theo. MWs (Da) |
|---|---|---|---|---|---|
| TT27 | 11000 | Haptoglobin precursor | Mouse | Q61646 | 38727 |
| | | Transthyretin precursor | Mouse | P07309 | 15766 |
| | | Hemoglobin alpha chain | Mouse | P01942 | 14945 |
| | | Hemoglobin beta-1 chain (B1) | Mouse | P02088 | 15699 |
| TT28 | 10000 | Hemoglobin alpha chain | Mouse | P01942 | 14945 |
| | | Hemoglobin beta-1 chain (B1) | Mouse | P02088 | 15699 |
| | | Haptoglobin precursor | Mouse | Q61646 | 38727 |
| | | Proline-rich protein 4 precursor | HUMAN | Q16378 | 15088 |
| | | Major urinary protein 1 precursor* | Mouse | P11588 | 20635 |
| | | Major urinary protein 6 precursor* | Mouse | P02762 | 20636 |
| | | Major urinary proteins 11 and 8* | Mouse | P04938 | 17549 |
| | | Mitochondrial inner membrane | Mouse | Q8CAQ8 | 83848 |
| | | Serum albumin precursor | Mouse | P07724 | 68648 |
| | | Heat shock protein HSP 90-beta | Mouse | P11499 | 83142 |
| TT29 | 7000 | Apolipoprotein C-III precursor | Mouse | P33622 | 10975 |
| | | Serum albumin precursor | Mouse | P07724 | 68648 |
| | | Alpha-1-antitrypsin 1-1 precursor* | Mouse | P07758 | 45974 |
| | | Alpha-1-antitrypsin 1-2 precursor* | Mouse | P22599 | 45946 |
| | | Alpha-1-antitrypsin 1-3 precursor* | Mouse | Q00896 | 45825 |
| | | Alpha-1-antitrypsin 1-4 precursor* | Mouse | Q00897 | 45969 |
| | | Alpha-1-antitrypsin 1-6 precursor* | Mouse | P81105 | 45794 |
| TT30 | 6000 | Apolipoprotein C-III precursor | Mouse | P33622 | 10975 |
| | | Serum albumin precursor | Mouse | P07724 | 68648 |
| | | Dermcidin precursor | HUMAN | P81605 | 11277 |
| | | Ras-related protein Rab-3C | Mouse | P62823 | 25856 |
| | | Alpha-1-antitrypsin 1-3 precursor | Mouse | Q00896 | 45825 |
| | | Apolipoprotein A-II precursor | Mouse | P09813 | 11312 |
| | | Major urinary protein | Mouse | P11588 | 20635 |

TABLE 6-continued

| Sample | Approx. gel MWs (Da) | Protein ID | Species | SWISS-PROT A/C No. | Theo. MWs (Da) |
|---|---|---|---|---|---|
| | | 1 precursor* | | | |
| | | Major urinary protein 6 precursor* | Mouse | P02762 | 20636 |
| | | Major urinary proteins 11 and 8* | Mouse | P04938 | 17549 |
| | | Hemoglobin alpha chain | Mouse | P01942 | 14945 |
| TT31 | 5500 | Apolipoprotein C-III precursor | Mouse | P33622 | 10975 |
| | | Apolipoprotein A-II precursor | Mouse | P09813 | 11312 |
| | | Serum albumin precursor | Mouse | P07724 | 68648 |
| TT32 | 3000 | Serum albumin precursor | Mouse | P07724 | 68648 |
| | | Beta-lactoglobulin precursor | BOVINE | P02754 | 19870 |
| | | Alpha-1-antitrypsin 1-2 precursor* | Mouse | P22599 | 45946 |
| | | Alpha-1-antitrypsin 1-4 precursor* | Mouse | Q00897 | 45969 |
| | | Alpha-1-antitrypsin 1-3 precursor* | Mouse | Q00896 | 45825 |
| | | Alpha-1-antitrypsin 1-6 precursor* | Mouse | P81105 | 45794 |
| TT41 | 8000-9000 | Apolipoprotein C-III precursor | Mouse | P33622 | 10975 |
| | | Alpha-1-antitrypsin 1-3 precursor* | Mouse | Q00896 | 45825 |
| | | Alpha-1-antitrypsin 1-6 precursor* | Mouse | P81105 | 45794 |
| | | Alpha-1-antitrypsin 1-2 precursor* | Mouse | P22599 | 45946 |
| | | Alpha-1-antitrypsin 1-4 precursor* | Mouse | Q00897 | 45969 |
| | | Serum albumin precursor | Mouse | P07724 | 68648 |
| | | Major urinary protein 1 precursor* | Mouse | P11588 | 20635 |
| | | Major urinary protein 2 precursor* | Mouse | P11589 | 20650 |
| | | Major urinary protein 5 precursor* | Mouse | P11591 | 20993 |
| | | Major urinary protein 6 precursor* | Mouse | P02762 | 20636 |
| | | Major urinary proteins 11 and 8* | Mouse | P04938 | 17549 |
| TT43 | 3500-5000 | Serum albumin precursor | Mouse | P07724 | 68648 |
| | | Apolipoprotein C-II precursor | Mouse | Q05020 | 10734 |
| | | Hemoglobin alpha chain | Mouse | P01942 | 14945 |
| | | Apolipoprotein A-II precursor | Mouse | P09813 | 11312 |
| | | Major urinary protein 1 precursor* | Mouse | P11588 | 20635 |
| | | Major urinary protein 2 precursor* | Mouse | P11589 | 20650 |
| | | Major urinary protein 5 precursor* | Mouse | P11591 | 20993 |
| | | Major urinary protein 6 precursor* | Mouse | P02762 | 20636 |
| | | Major urinary proteins 11 and 8* | Mouse | P04938 | 17549 |
| | | Alpha-1-antitrypsin 1-2 precursor* | Mouse | P22599 | 45946 |
| | | Alpha-1-antitrypsin 1-4 precursor* | Mouse | Q00897 | 45969 |
| | | Alpha-1-antitrypsin 1-3 precursor* | Mouse | Q00896 | 45825 |
| | | Alpha-1-antitrypsin 1-6 precursor* | Mouse | P81105 | 45794 |

TABLE 7

| Protein | SWISS-PROT Accession No. Mouse | SWISS-PROT Accession No. Human |
|---|---|---|
| Hemoglobin alpha chain | P01942 | P69905 |
| Hemoglobin beta-1 chain (B1) | P02088 | P68871 |
| Beta-lactoglobulin precursor (bovine) | P02754 | — |
| Major urinary protein 6 precursor | P02762 | — |
| Major urinary proteins 11 and 8 | P04938 | — |
| Transthyretin precursor | P07309 | P02766 |
| Serum albumin precursor | P07724 | P02768 |
| Alpha1-1-antitrypsin 1-1 precursor | P07758 | P01009 |
| Apolipoprotein A-II precursor | P09813 | P02652 |
| Heat shock protein HSP 90-beta | P11499 | P08238 |
| Major urinary protein 1 precursor | P11588 | — |
| Major urinary protein 2 precursor | P11589 | — |
| Major urinary protein 5 precursor | P11591 | — |
| Alpha-1-antitrypsin 1-2 precursor | P22599 | — |
| Apolipoprotein C-III precursor | P33622 | P02656 |
| Ras-related protein Rab-3C | P62823 | Q96E17 |
| Alpha-1-antitrypsin 1-6 precursor | P81105 | — |
| Dermcidin precursor (human) | P81605 | P81605 |
| Alpha-1-antitrypsin 1-3 precursor | Q00896 | — |
| Alpha-1-antitrypsin 1-4 precursor | Q00897 | — |
| Apolipoprotein C-II precursor | Q05020 | P02655 |
| Proline-rich protein 4 precursor (human) | Q16378 | Q16378 |
| Haptoglobin precursor | Q61646 | P00738 |
| Mitochondrial inner membrane | Q8CAQ8 | Q16891 |

SELDI peaks 1-6 (see table 3) were investigated using BioLynx software. In the BioLynx analysis, the average mass (i.e. zero charge state) of the peak of interest was used ±2 or 3 daltons when searching for predicted fragments.

FIG. 10 shows the proteins identified in the gel bands corresponding to the SELDI m/z values of peaks 1-6. The tables show the peptides observed in LC/MS/MS (Mascot residue numbers) that were used to determine the identity of the protein in question along with their BioLynx equivalent residue numbers (where necessary), and the peptide residue numbers of the BioLynx predicted peptide that 'covers' or matches the Mascot peptide residue numbers.

It is possible that each SELDI peak observed contains a mixture of molecules, each giving rise to some proportion of the intensity observed for the peak. Furthermore, since the majority of the proteins identified have expected molecular weights higher than 11 kDa the SELDI peaks are very likely to contain fragments of these proteins. The BioLynx correlation exercise has generated a set of possible fragment sequences which originate from any of the 24 proteins listed in Table 7.

FIG. 11 illustrates the rationale of analyzing observed peptide fragments using BioLynx. As shown in FIG. 11a, for example, peak 1 (av. mass 3770 Da) is represented by the gel bands TK and TV of LC/MS/MS sample TT43. Shown underneath the spectral and gel images is the amino acid sequence of major urinary protein 1 (precursor, i.e. full-length). The peptide on which the identification was derived by Mascot is underlined. Highlighted is the peptide predicted by BioLynx that matches the m/z of the SELDI peak and also includes the Mascot (experimentally observed) peptide. The text indicates the equivalent Swiss-Prot amino acid residue numbers of the BioLynx predicted peptide. Also, the signal sequence of the protein (the first 19 amino acids) is indicated by black lines which is typically removed to create the mature protein.

Peptides observed in the LC/MS/MS experiment must then map onto the predicted fragment of the protein and this must also have the molecular weight consistent with the observed SELDI value.

Proteins observed in multiple peaks are potentially better biomarker candidates.

Preliminary experiments to validate these biomarkers would involve Western blotting using carefully chosen (custom-made) antibodies which selectively recognise unique epitopes on the fragment sequences themselves and not the whole protein.

The invention claimed is:

1. A method of screening an agent to determine its usefulness in treating Alzheimer's disease, the method comprising:

(a) providing an animal model of Alzheimer's disease, said animal model comprising an animal subject in which tubulin beta-3 and at least one of the proteins selected from the group consisting of Glutathione S-transferase Mu 1; DNA segment, Chr 10, Johns Hopkins University 81 expressed; Tubulin beta-4 chain; Tubulin beta-2 chain (gi 13542680; p gi 7106439); tubulin beta chain 15; drebrin-like; WW domain binding protein 2 (WBP-2); Tubulin alpha-1 chain; Eukaryotic translation initiation factor 4H (eIF-4H); Nit protein 2; Transcriptional activator protein PUR-alpha; Carbonic anhydrase 2; Tuba2 protein; pyruvate dehydrogenase (lipoamide) beta; beta-actin; Transitional endoplasmic reticulum ATPase; SH3-containing GRB2-like protein 2; Hspd1 protein; Ubiquitin carboxyl-terminal hydrolase isozyme L1; Actin 1; ATP synthase beta chain, mitochondrial precursor; neuronal protein Np25; ATP synthase, H+ transporting; guanylate kinase 1; glutathione S-transferase; guanosine diphosphate (GDP) dissociation inhibitor 1; tumor rejection antigen gp96; ubiquitin-activating enzyme E1; dnaK-type molecular chaperone precursor; dnaK-type molecular charperone hsp72-ps1; ATPase, H+ transporting, liposomal (rat); ATPase H+ transporting, liposomal (mouse); heat shock 27 kpa protein 1; Junction plakoglobin (Desmoplakin III); dihydropyrimidinase-like 2; NADH dehydrogenase (ubiquinone) Fe—S protein 1; annexin VII; N-myc downstream regulated 2; enolase 2; gamma-actin; Tubulin alpha-1 chain; ATP synthase beta chain; Ubiquitin carboxyl-terminal hydrolase similar to interferon-inducible protein 10 (IP-10) receptor; tropomyosin beta; Protein kinase C inhibitor; tubulin, beta polypeptide; ATP synthase alpha chain; Superoxide dismutase; protein phosphatase-1 regulatory subunit 7; CGI-121 protein; Ubiquitin carboxyl-terminal hydrolase isozyme L1; ferritin heavy chain; Gamma-soluble NSF attachment protein; Prefoldin subunit 5; cAMP-dependent protein kinase type I-alpha regulatory chain; guanylate kinase 1; Aspartate aminotransferase, cytoplasmic; Fructose-bisphosphate aldolase C; Fructose-bisphosphate aldolase A; isocitrate dehydrogenase 3, beta subunit; synapsin II; 40 kpa peptidyl-prolyl cis-trans isomerase; 2',3'-cyclic nucleotide 3'-phosphodiesterase; Acetyl-CoA acetyltransferase 1 precursor; Cytosolic acyl coenzyme A thioester hydrolase; Pyruvate dehydrogenase E1 component, alpha subunit; Creatine kinase, ubiquitous mitochondrial precursor; Heterogeneous nuclear ribonucleoprotein D0; Phosphoglycerate kinase 1; Neuronal tropomodulin (Swiss-PROT No. Q9JKK7; gi 23396882); Nucleolysin TIAR; peptidyl-prolyl isomerase D; aspartate transaminase; aldolase A; isocitrate dehydrogenase 3; Voltage-dependent anion-selective channel protein 1; Short chain 3-hydroxyacyl-CoA dehydrogenase, mitochondrial precursor; ATP synthase alpha chain, mitochondrial precursor; Voltage-dependent anion-selective channel protein 2; Carbonyl reductase [NADPH] 1 (EC 1.1.1.184) (NADPH-dependent carbonyl reductase 1); microtubule-associated protein 1 B; 14-3-3 protein zeta/delta; Phosphoglycerate mutase 1; COP9 (constitutive photomorphogenic) homolog, subunit 7a; Acetyl-CoA acetyltransferase, mitochondrial precursor; Ubiquinol-cytochrome C reductase complex core protein 2; Proteasome subunit alpha type 6; Alpha-internexin (Alpha-Inx); hosphoglycerate mutase 1; HSCO protein; Ubiquinol-cytochrome C reductase complex core protein I, mitochondrial precursor; Neurofilament triplet M protein; Mu-crystallin homolog; Dihydropyrimidinase related protein-2 (DRP-2); Apolipoprotein E precursor (Apo-E); Neurofilament triplet L protein; Alpha enolase; Creatine kinase, B chain; Neurofilament triplet M protein; Voltage-dependent anion-selective channel protein 2; RIKEN cDNA 4732495G21 gene; Glycerol-3-phosphate dehydrogenase; Lamin B2; Dihydropyrimidinase related protein-2 (DRP-2); Lamin B3; Hemoglobin alpha chain; Hemoglobin beta-1 chain (B1); Beta-lactoglobulin precursor (bovine); Major urinary protein 6 precursor; Major urinary proteins 11 and 8; Transthyretin precursor; Serum albumin precursor; Alpha-1-antitrypsin 1-1 precursor; Apolipoprotein A-II precursor; Heat shock protein HSP 90-beta; Major urinary protein 1 precursor; Major urinary protein 2 precursor; Major urinary protein 5 precursor; Alpha-1-antitrypsin 1-2 precursor; Apolipoprotein C-III precursor; Ras-related protein Rab-3C; Alpha-1-antitrypsin 1-6 precursor; Dermcidin precursor (human); Alpha-1-antitrypsin 1-3 precursor; Alpha-1-antitrypsin 1-4 precursor; Apolipoprotein C-II precursor; Proline-rich protein 4 precursor (human); and Haptoglobin precursor Mitochondrial inner membrane are differentially expressed in relevant tissue of said animal subject, or in cells derived from said tissue, as compared to a normal subject, and said animal subject has been treated with the agent undergoing screening;

(b) obtaining from said animal subject, after being treated with the agent undergoing screening, a sample of relevant tissue, or cells derived from said tissue;

(c) determining the presence, absence or degree of expression of the differentially expressed proteins in said tissue from the treated animal subject or in said cells; and (d) selecting or rejecting the agent according to the extent to which it changes the expression, activity or amount of the differentially expressed proteins in the treated animal subject towards that of a normal subject.

2. The method of claim 1, wherein the agent is selected if it converts the expression of the proteins to that of the normal subject.

3. The method of claim 1, wherein said animal model is selected from the group consisting of an amyloid precursor protein (APP) and presenilin-1 (PS-1) double transgenic mouse; a single transgenic APP mouse; and a single transgenic PS-1 mouse said transgenic mice differentially expressing said at least one protein as compared to a wild-type mouse.

4. The method of claim 1, wherein the tissue samples are brain tissue samples.

5. The method of claim 1, wherein the tissue samples are blood, serum or cerebro-spinal fluid samples.

6. The method of claim 1, wherein the at least one protein is selected from the group consisting of guanosine diphosphate dissociation inhibitor 1, dihydropyrimidinease related protein-2, proteasome subunit alpha type 6, apolipoprotein E, synapsin II, ubiquitin carboxyl-terminal hydrolase isozyme L1, aspartate aminotransferase, glutathione S-transferase mu 1, tubulin beta-4 chain, WW domain binding protein 2, eukaryotic translation initiation factor 4H, neuronal protein Np25, fructose-bisphosphate aldolase A, fructose-bisphosphate aldolase C, nucleolysin TIA related protein, peptidyl-prolyl isomerase D, voltage-dependent anion-selective channel protein 1 and acetyl-COA acetyltransferase mitochondrial precursor.

7. The method of claim 1, wherein the agents or proteins are screened using a high throughput screening method.

8. The method of claim 1 wherein said animal subject is a transgenic mouse selected from the group consisting of an amyloid precursor protein (APP) and presenilin-1 (PS-1) double transgenic mouse, a single transgenic APP mouse and a single transgenic PS-1 mouse; and wherein said animal model further comprises wild-type mice in a paradigm comprising:

(a) said wild-type mice and said transgenic mice; and (b) said transgenic mice which have not been treated with the agent and said transgenic mice which have been treated with the agent.

9. The method of claim 1 wherein said animal subject is a transgenic mouse selected from the group consisting of an amyloid precursor protein (APP) and presenilin-1 (PS-1) double transgenic mouse, a single transgenic APP mouse and a single transgenic PS-1 mouse; and wherein said animal model further comprises wild type mice in a paradigm comprising:

(a) said wild-type mice who have and have not been treated with the agent; and (b) said transgenic mice who have and have not been treated with the agent.

10. The method of claim 1 wherein the proteins present in a sample are established using two-dimensional gel electrophoresis or SELDI analysis carried out on the relevant tissue or a protein-containing extract thereof.

11. The method of claim 10, wherein the proteins are subsequently identified using mass spectrometry to analyse said proteins and a database search.

12. The method of claim 1, further comprising the step of isolating a differentially expressed protein identified in the method.

13. The method of claim 12, further comprising the step of characterising the isolated protein.

14. The method of claim 12, further comprising the step of screening for specific binding partners of the protein.

15. The method of claim 12, further comprising the step of screening for agonists or antagonists of the protein.

16. A method of screening for compounds potentially useful in the prevention or treatment of Alzheimer's disease, the method comprising:

contacting at least one candidate compound with at least one of a cell-based system of Alzheimer's disease and an animal model-based system of Alzheimer's disease in which tubulin beta-3 and at least one further protein are differentially expressed, said at least one further protein being selected from the group consisting of Glutathione S-transferase Mu 1; DNA segment, Chr 10, Johns Hopkins University 81 expressed; Tubulin beta-4 chain; Tubulin beta-2 chain (gi 13542680; p gi 7106439); tubulin beta chain 15; drebrin-like; WW domain binding protein 2 (WBP-2); Tubulin alpha-1 chain; Eukaryotic translation initiation factor 4H (eIF-4H); Nit protein 2; Transcriptional activator protein PUR-alpha; Carbonic anhydrase 2; Tuba2 protein; pyruvate dehydrogenase (lipoamide) beta; beta-actin; Transitional endoplasmic reticulum ATPase; SH3-containing GRB2-like protein 2; Hspd1 protein; Ubiquitin carboxyl-terminal hydrolase isozyme L1; Actin 1; ATP synthase beta chain, mitochondrial precursor; neuronal protein Np25; ATP synthase, H+ transporting; guanylate kinase 1; glutathione S-transferase; guanosine diphosphate (GDP) dissociation inhibitor 1; tumor rejection antigen gp96; ubiquitin-activating enzyme E1; dnaK-type molecular chaperone precursor; dnaK-type molecular charperone hsp72-ps1; ATPase, H+ transporting, liposomal (rat); ATPase H+ transporting, liposomal (mouse); heat shock 27 kpa protein 1; Junction plakoglobin (Desmoplakin III); dihydropyrimidinase-like 2; NADH dehydrogenase (ubiquinone) Fe—S protein 1; annexin VII; N-myc downstream regulated 2; enolase 2; gamma-actin; Tubulin alpha-1 chain; ATP synthase beta chain; Ubiquitin carboxyl-terminal hydrolase similar to interferon-inducible protein 10 (IP-10) receptor; tropomyosin beta; Protein kinase C inhibitor; tubulin, beta polypeptide; ATP synthase alpha chain; Superoxide dismutase; protein phosphatase-1 regulatory subunit 7; CGI-121 protein; Ubiquitin carboxyl-terminal hydrolase isozyme L1; ferritin heavy chain; Gamma-soluble NSF attachment protein; Prefoldin subunit 5; cAMP-dependent protein kinase type I-alpha regulatory chain; guanylate kinase 1; Aspartate aminotransferase, cytoplasmic; Fructose-bisphosphate aldolase C; Fructose-bisphosphate aldolase A; isocitrate dehydrogenase 3, beta subunit; synapsin II; 40 kpa peptidyl-prolyl cis-trans isomerase; 2',3'-cyclic nucleotide 3'-phosphodiesterase; Acetyl-CoA acetyltransferase 1 precursor; Cytosolic acyl coenzyme A thioester hydrolase; Pyruvate dehydrogenase E1 component, alpha subunit; Creatine kinase, ubiquitous mitochondrial precursor; Heterogeneous nuclear ribonucleoprotein D0; Phosphoglycerate kinase 1; Neuronal tropomodulin (Swiss-PROT No. Q9JKK7; gi 23396882); Nucleolysin TIAR; peptidylprolyl isomerase D; aspartate transaminase; aldolase A; isocitrate dehydrogenase 3; Voltage-dependent anion-selective channel protein 1; Short chain 3-hydroxyacyl-CoA dehydrogenase, mitochondrial precursor; ATP synthase alpha chain, mitochondrial precursor; Voltage-dependent anion-selective channel protein 2; Carbonyl reductase [NADPH] 1 (EC 1.1.1.184) (NADPH-dependent carbonyl reductase 1); microtubule-associated protein 1 B; 14-3-3 protein zeta/delta; Phosphoglycerate mutase 1; COP9 (constitutive photomorphogenic) homolog, subunit 7a; Acetyl-CoA acetyltransferase, mitochondrial precursor; Ubiquinol-cytochrome C reductase complex core protein 2; Proteasome subunit alpha type 6; Alpha-internexin (Alpha-Inx); hosphoglycerate mutase 1; HSCO protein; Ubiquinol-cytochrome C reductase complex core protein I, mitochondrial precursor; Neurofilament triplet M protein; Mu-crystallin homolog; Dihydropyrimidinase related protein-2 (DRP-2); Apolipoprotein E precursor (Apo-E); Neurofilament triplet L protein; Alpha enolase; Creatine kinase, B chain; Neurofilament triplet M protein; Voltage-dependent anion-selective channel protein 2; RIKEN cDNA 4732495G21 gene; Glycerol-3-phosphate dehydrogenase; Lamin B2; Dihydropyrimidinase related protein-2 (DRP-2); Lamin B3; Hemoglobin alpha chain; Hemoglobin beta-1 chain (B1); Beta-lactoglobulin precursor (bovine); Major urinary protein 6 precursor; Major urinary proteins 11 and 8; Transthyretin precursor; Serum albumin precursor; Alpha-1-antitrypsin 1-1 precursor; Apolipoprotein A-II precursor; Heat shock protein HSP 90-beta; Major urinary protein 1 precursor; Major urinary protein 2 precursor; Major urinary protein 5 precursor; Alpha-1-antitrypsin 1-2 precursor; Apolipoprotein C-III precursor; Ras-related protein Rab-3C; Alpha-1-antitrypsin 1-6 precursor; Dermcidin precursor (human); Alpha-1-antitrypsin 1-3 precursor; Alpha-1-antitrypsin 1-4 precursor; Apolipoprotein C-II precursor; Proline-rich protein 4 precursor (human); and Haptoglobin precursor Mitochondrial inner membrane, or human proteins corresponding to any of said proteins; and determining whether said at least one candidate compound is capable of modulating the expression or level of said proteins.

17. A method according to claim 16 which is an in vitro method.

\* \* \* \* \*

UNITED STATES PATENT AND TRADEMARK OFFICE
CERTIFICATE OF CORRECTION

PATENT NO. : 8,658,133 B2  Page 1 of 1
APPLICATION NO. : 11/574367
DATED : February 25, 2014
INVENTOR(S) : Ward et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1727 days.

Signed and Sealed this

Twenty-ninth Day of September, 2015

Michelle K. Lee
*Director of the United States Patent and Trademark Office*